US011707519B2

(12) United States Patent
Cox et al.

(10) Patent No.: US 11,707,519 B2
(45) Date of Patent: Jul. 25, 2023

(54) PHOSPHORYLATED HEPTOSE COMPOUNDS: PROCESS FOR THEIR PREPARATION AND USE

(71) Applicants: NATIONAL RESEARCH COUNCIL OF CANADA, Ottawa (CA); UNIVERSITY COLLEGE DUBLIN, Dublin (IE)

(72) Inventors: Andrew Cox, Ottawa (CA); Janelle Sauvageau, Ottawa (CA); Stefan Oscarson, Dublin (IE); Lorenzo Guazzelli, Dublin (IE)

(73) Assignees: UNIVERSITY COLLEGE DUBLIN, NATIONAL UNIVERSITY OF IRELAND, Dublin (IE); NATIONAL RESEARCH COUNCIL OF CANADA, Ottawa (CA)

(*) Notice: Subject to any disclaimer, the term of this patent is extended or adjusted under 35 U.S.C. 154(b) by 724 days.

(21) Appl. No.: 16/612,289

(22) PCT Filed: May 11, 2018

(86) PCT No.: PCT/CA2018/000090
§ 371 (c)(1),
(2) Date: Mar. 30, 2020

(87) PCT Pub. No.: WO2018/205009
PCT Pub. Date: Nov. 15, 2018

(65) Prior Publication Data
US 2020/0215186 A1 Jul. 9, 2020

Related U.S. Application Data

(60) Provisional application No. 62/504,748, filed on May 11, 2017.

(51) Int. Cl.
*C07H 13/00* (2006.01)
*A61K 39/39* (2006.01)
*A61P 37/04* (2006.01)
*A61K 39/00* (2006.01)

(52) U.S. Cl.
CPC ............. *A61K 39/39* (2013.01); *A61K 39/00* (2013.01); *A61P 37/04* (2018.01); *C07H 13/00* (2013.01)

(58) Field of Classification Search
None
See application file for complete search history.

(56) References Cited

FOREIGN PATENT DOCUMENTS

EP 2669288 A1 12/2013
WO 2016054745 A1 4/2016

OTHER PUBLICATIONS

D'Souza et al., Bioorganic and Medicinal Chemistry Letters, vol. 7, No. 19, pp. 2457-2462, 1997. (Year: 1997).*
J. Robinson and K, Moehle, "Structural aspects of molecular recognition in the immune system Part II: Pattern recognition receptors," Pure and Applied Chemistry, 2014, vol. 86: Issue 10, pp. 1483-1538; Zurich, Switzerland.
P. Singh, et al., "Use of Ferric Chloride in Carbohydrate Chemistry. I. A Quick Method For the Preparation of O-Isopropylidene Derivatives of Carbohydrates," Tetrahedron Letters, 1977, No. 5, pp. 439-440, Great Britain.
L. Wang et al., "Divergence of Biochemical Function in the HAD Superfamily: D-glycero-D-manno-heptose-1,7-bisphosphate Phosphatase (GmhB)," Biochemistry, 2010, vol. 49: No. 6, pp. 1072-1081; Department of Chemistry and Chemical Biology, University of New Mexico, Albuquerque, New Mexico 87131, USA.
A. Zamyatina et al., "Efficient chemical synthesis of both anomers of ADP L-glycero- and D-glycero-D-manno-heptopyranose," Carbohydrate Research, 2003, vol. 338; pp. 2571-2589; Institute of Chemistry, University of Agricultural Sciences, Muthgasse 18, A-1190 Vienna, Austria.
J. Brimacombe and A. Kabir, "The Synthesis of Some Seven-Carbon Sugars via The Osmylation of Olefinic Sugars," Carbohydrate Research, 1986, vol. 150; pp. 35-51; Chemistry Department, Dundee University, Dundee DD1 4HN Great Britain.
J. Brimacombe and A. Kabir "Convenient Syntheses of L-Glycero-D-Manno-Heptose and D-glycero-D-Manno-Heptose," Carbohydrate Research,1986, vol. 152; pp. 329-334; Chemistry Department, Dundee University, Dundee DD1 4HN Great Britain.
R. Gaudet, et al., "Cytosolic detection of the bacterial metabolite HBP activates TIFA-dependent innate immunity," Science, sciencemag.org, 2015, vol. 348: Issue 6240; pp. 1251-1255. American Association for the Advancement of Science, 1200 New York Avenue NW, Washington, DC 20005.
H. Guzlek, et al., "A short synthesis of D-glycero-D-manno-heptose 7-phosphate," Carbohydrate Research, 2005, vol. 340; pp. 2808-2811; Department of Chemistry, University of Natural Resources and Applied Life Sciences, Muthgasse 18, A-1190 Vienna, Austria.
J. Malott, et al., "Neisseria gonorrhoeae-derived heptose elicits an innate immune response and drives HIV-1 expression," Proceedings of the National Academy of Sciences of the United States of America, 2013; vol. 110: No. 25 pp. 10234-10239.
R. Medzhitov, et al., "Recognition of microorganisms and activation of the immune response," Nature, 2007, vol. 449: No. 18; p. 819-826; Nature Publishing Group.
R. Medzhitov, et al., "Approaching the Asymptote: 20 Years Later," Immunity Perspective, 2009, vol. 30: Issue 6; pp. 766-775.
Extended European Search Report for European Patent Application No. 18797916.6, dated Dec. 21, 2020, 11 pages.
Butty et al., "Article Elucidating the Formation of 6-Deoxyheptose: Biochemical Characterization of the GDP-d-glycero-d-manno-heptose C6 Dehydratase, DmhA, and its Associated C4 Reductase, DmhB", BioChemistry, Aug. 18, 2009, 7764-7775 pages, vol. 48, No. 32.

(Continued)

*Primary Examiner* — Traviss C McIntosh, III
(74) *Attorney, Agent, or Firm* — Jordan IP Law, LLC

(57) ABSTRACT

Processes for the preparation of phosphorylated heptose compounds are provided. Embodiments of the invention relate to the chemical synthesis of heptopyranose phosphate compounds. Also, embodiments of the invention relate to the use of compounds according to the invention in modulating an immune response in a subject.

19 Claims, 43 Drawing Sheets

(56) References Cited

OTHER PUBLICATIONS

Souza et al., "Catalytic mechanism of KD08P synthase: synthesis and evaluation of a putative reaction intermediate", Biorganic & Medicinal Chemistry Letters, Elsevier, Oct. 7, 1997, pp. 2457-2462, vol. 7, No. 19, Amsterdam, NL.
International Search Report and Written Opinion for International Patent Application No. PCT/CA2018/00090, dated Aug. 1, 2018, 11 pages.
Borio et al., "Chemical synthesis of the innate immune modulator—bacterial d-glycero-β- d-manno-heptose-1,7-bisphosphate (HBP)", Tetrahedron Letters, Jun. 13, 2017, vol. 58, Issue 29, pp. 2826-2829.
European Office Action for European Patent Application No. 18797916.6, dated Oct. 4, 2022, 6 pages.

\* cited by examiner

A) Belongs to compound 2

B) Belongs to compound 2

A) Belongs to compound 3

B) Belongs to compound 3

A) Belongs to compound 4

B) Belongs to compound 4

A) Belongs to compound 5

B) Belongs to compound 5

A) Belongs to compound 6

B) Belongs to compound 6

A) Belongs to compound 7

B) Belongs to compound 7

A) Belongs to compound 8

B) Belongs to compound 8

C) Belongs to compound 8

A) Belongs to compound 9

B) Belongs to compound 9

C) Belongs to compound 9

A) Belongs to compound 10

B) Belongs to compound 10

A) Belongs to compound 11

B) Belongs to compound 11

C) Belongs to compound 11

A) Belongs to compound 12β

B) Belongs to compound 12β

C) Belongs to compound 12β

A) Belongs to compound 12α

B) Belongs to compound 12α

C) Belongs to compound 12α

A) Belongs to compound JS6

B) Belongs to compound JS6

C) Belongs to compound JS6

A) Belongs to compound JS5

B) Belongs to compound JS5

PHOSPHORYLATED HEPTOSE COMPOUNDS: PROCESS FOR THEIR PREPARATION AND USE

This application claims the benefit of U.S. Provisional Patent Application Ser. No. 62/504,748 filed on May 11, 2017. The content of the U.S. Provisional Patent Application is incorporated herein in its entirety by reference.

FIELD OF THE INVENTION

The present invention relates generally to phosphorylated heptose compounds. More specifically, the present invention relates to the chemical synthesis of heptopyranose phosphates and their use in modulating an immune response in a subject.

BACKGROUND OF THE INVENTION

An ability to modulate the immune system is becoming more and more critical as we strive to improve the immune response of individuals in order to generate a protective response, e.g. in immunocompromised individuals including cancer patients. This is outlined for example in WO 2016/054745 entitled "Methods of modulating immune system responses."

Pathogen-associated molecular patterns (PAMPs) are molecules produced by pathogens that are specifically recognised by the human immune system in order to generate innate and adaptive immune responses to keep foreign pathogens at bay. The ability to synthesise PAMP's will enable the specific modulation of the immune system to improve the immune response and generate protection.

Only a limited number of PAMPs have been identified, e.g. lipopolysaccharide (LPS), DNA and flagellin. This limits the opportunity to investigate the immunomodulatory properties of these molecules. In most cases PAMPs are difficult to synthesise or isolate and thus precludes an opportunity to specifically address how these PAMP's interact with the immune system in order to exploit this relationship as a pure, fully characterised supply of the PAMPs is unavailable. PAMP fragments are known in the art [1,2]. Also, chemical syntheses of PAMP molecule are known [9].

The inventors are also aware of the following documents: Gaudet et al. [10] and Malott et al. [11].

There is a need to identify novel PAMP molecules. Also, there is a need to develop chemical syntheses for the preparation of PAMP molecules. In particular, there is a need to develop efficient chemical syntheses that allow for the preparation of PAMP molecules in amounts suitable for the study of interactions of these molecules with the immune system of a subject.

SUMMARY OF THE INVENTION

The inventors have designed chemical syntheses for the preparation of phosphorylated heptose compounds. Embodiments of the invention relate to the chemical synthesis of heptopyranose phosphate compounds. Also, embodiments of the invention relate to the use of compounds according to the invention in modulating an immune response in a subject.

More specifically, in accordance with aspects of the invention, there is provided the following:

(1) A process for preparing a phosphorylated heptose compound, comprising the steps of:
   (a) providing a compound having first and second hydroxyl (OH) groups to be phosphorylated and one or more other OH groups;
   (b) selectively protecting the first OH group to be phosphorylated with a first protecting group;
   (c) selectively protecting the second OH group to be phosphorylated with a second protecting group;
   (d) selectively deprotecting the first OH group;
   (e) phosphorylating the first OH group;
   (f) selectively deprotecting the second OH group;
   (g) phosphorylating the second OH group to obtain the phosphorylated heptose compound,
   wherein during steps (c)-(g), the one or more other OH groups of the compound are protected with a protecting group.

(2) A process according to (1) above, further comprising a step of (h) deprotecting the one or more OH groups.

(3) A process according to (1) or (2) above, wherein, at step (c), the one or more other OH groups are also protected by the second protecting group; and at step (f) only the second OH group is deprotected.

(4) A process according to any one of (1) to (3) above, wherein the compound at step (a) is obtained from a starting compound having three or more OH groups wherein all the OH groups are protected by protecting groups which are the same and are different from the first and second protecting groups, and the protecting groups of the starting compound are removed prior to conducting step (b).

(5) A process according to (4) above, wherein removal of the protecting groups of the starting compound and steps (b) and (c) are performed sequentially without product isolation.

(6) A process according to any one of (1) to (5) above, wherein all the OH groups of the starting compound are each protected by acetyl (Ac), benzoyl (Bz), benzyl (Bn), p-methoxybenzyl (PMB) or a sillyl-based protecting group including tert-methyl silly (TMS), tert-butyl-dimethyl sillyl (TBDMS) and tert-butyl diphenyl sillyl (TBDPS).

(7) A process according to any one of (1) to (5) above, wherein all the OH groups of the starting compound are each protected by acetyl (Ac).

(8) A process according to any one of (1) to (7) above, wherein the first protecting group is triphenyl methyl (Tr), benzene or 1-(chlorodiphenylmethyl)-4-methoxy.

(9) A process according to any one of (1) to (8) above, wherein the second protecting group is benzoyl (Bz) or acetyl.

(10) A process according to any one of (1) to (5) above, wherein the first protecting group is Tr and the second protecting group is Bz.

(11) A process according to any one of (1) to (5) above, wherein: all the OH groups of the starting compound are each protected by acetyl (Ac), the first protecting group is Tr, and the second protecting group is Bz.

(12) A process according to any one of (1) to (11) above, wherein the compound at step (a) is a heptopyranose.

(13) A process according to any one of (1) to (11) above, wherein the compound at step (a) is a heptopyranose, and the first OH group is at position 7 and the second OH group is at position 1.

(14) A process according to (13) above, wherein: the heptopyranose is a mixture of α and β, at step (d) a is the major reaction product, separation of the α and β products is performed, and step (e) is performed on the α product.

(15) A process according to (14) above, wherein: at step (f) a mixture of α and β is obtained, β is the major reaction product, separation of the α and β products is performed, and step (g) is performed on the β product.

(16) A process according to (14) or (15) above, wherein separation of the α and β products is performed by a technique which is flash chromatography.

(17) A process for preparing D-glycero-D-manno-heptopyranose 1β,7-bisphosphate (JS6 or HBP-β), comprising the steps of:
(a) providing an α,β mixture of hydroxyl (OH)-protected D-glycero-D-manno-heptopyranose;
(b-c) preparing, from the α,β mixture of OH-protected D-glycero-D-manno-heptopyranose, a compound wherein the hydroxy group at position 7 is protected with a first protecting group and the other five OH groups are protected with a second protecting group;
(d) selectively deprotecting the OH at position 7 to obtain an α product;
(e) phosphorylating the OH at position 7 of the α product;
(f) selectively deprotecting the OH at position 1 to obtain an α,β mixture;
(g) phosphorylating the OH at position 1 of the α,β mixture of step (d) to obtain a β product;

(h) deprotecting the other four OH groups of the β product of step (e) to obtain D-glycero-D-manno-heptopyranose 1β,7-bisphosphate (JS6 or HBP-β).

(18) A process according to (17) above, wherein the α,β mixture of OH-protected D-glycero-D-manno-heptopyranose is α,β mixture of OH-Ac D-glycero-D-manno-heptopyranose or OH-Bz D-glycero-D-manno-heptopyranose.

(19) A process according to (17) or (18) above, wherein the first protecting group is Tr, benzene or 1-(chlorodiphenylmethyl)-4-methoxy.
(20) A process according to any one of (17) to (19) above, wherein the second protecting group is Bz or acetyl.
(21) A process according to any one of (17) to (20) above, wherein step (d) comprises separating the α and β products, and step (e) is performed on the α product.
(22) A process according to (21) above, wherein step (f) comprises separating the α and β products, and step (g) is performed on the β product.
(23) A process according to any one of (1) to (22) above, wherein the phosphorylation at steps (e) and (g) is performed independently using $iPr_2NP(OBn)_2$ or $P(O)(OPh)_2Cl$.
(24) A process for preparing D-glycero-D-manno-heptopyranose 1β,7-bisphosphate (7 or HBP-β), comprising a reaction sequence as outlined below

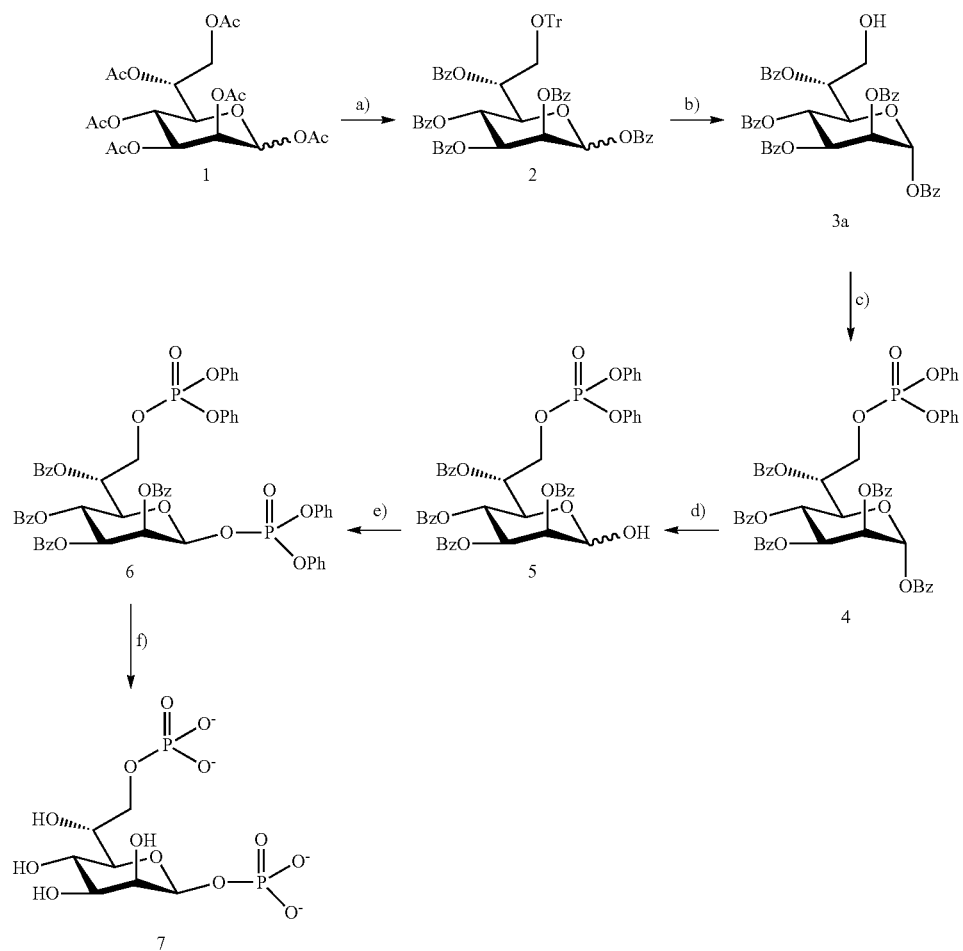

wherein: a) 1. MeONa, MeOH 2. TrCl, py, then BzCl; b) 1. $H_2$, Pd/C, TrCl, $CH_2Cl_2$ 2. separation of α and β; c) $P(O)(OPh)_2Cl$, DMAP, $CH_2Cl_2$; d) 1. HBr 33% in AcOH 2. AgOTf, $Ag_2CO_3$, $H_2O$, $CH_2Cl_2$; e) 1. $P(O)(OPh)_2Cl$, DMAP, $CH_2Cl_2$ 2. separation of α and β; f) 1. $PtO_2$, $H_2$, MeOH 2. NaOH (1M), $H_2O$, MeOH.
(25) A reaction product obtained by the process as defined in any one of (1) to (24) above and having the $^1H$ NMR spectra outlined herein in FIG. 15.

(26) A reaction product obtained by the process as defined in any one of (1) to (24) above and having the $^1$H-$^{13}$C NMR spectra outlined herein in FIG. 16.

(27) A pharmaceutical composition comprising the reaction product as defined in (25) or (26) above and a pharmaceutically acceptable carrier.

(28) A process for preparing D-glycero-D-manno-heptopyranose 1β,7-bisphosphate (JS6 or HBP-β), comprising a reaction step as outlined below

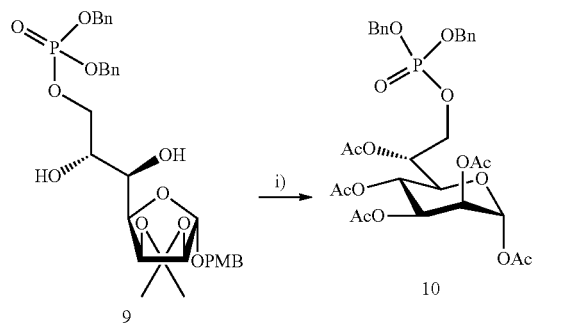

wherein: i) 1. TFA/water/DMC 2. acetic anhydride/pyridine (1/1) 3. separation of α and β.

(29) A process for preparing D-glycero-D-manno-heptopyranose 1β,7-bisphosphate (JS6 or HBP-β), comprising a reaction step as outlined below

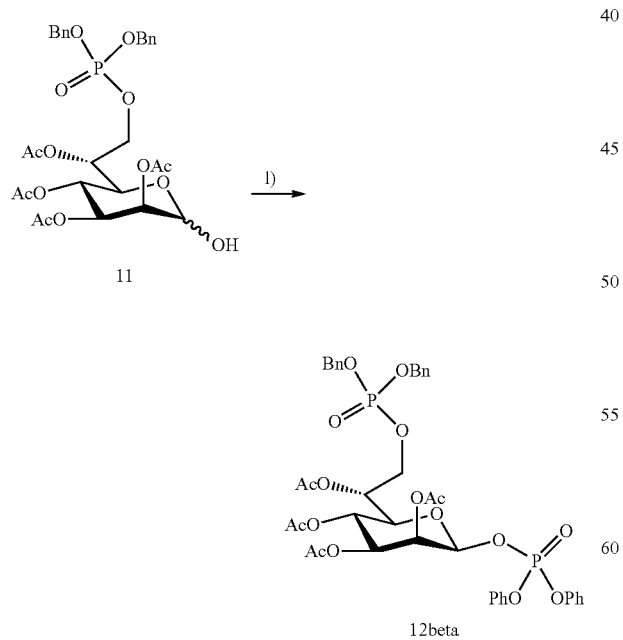

wherein: l) 1. P(O)(OPh)$_2$Cl, DCM diluted, DMAP 2. separation of α and β.

(30) A process for preparing D-glycero-D-manno-heptopyranose 1β,7-bisphosphate (JS6 or HBP-β), comprising a reaction sequence as outlined below

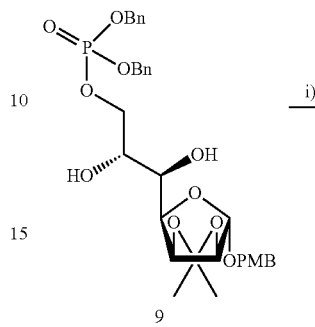

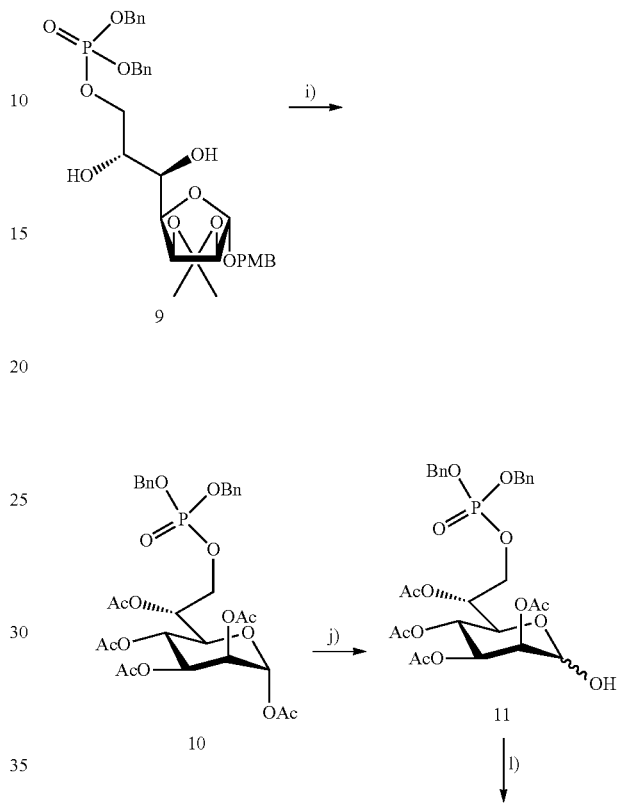

wherein: i) 1. TFA/water/DMC 2. acetic anhydride/pyridine (1/1) 3. separation of α and β; and j) DIPEA, ammonium acetate, DMF; and l) 1. P(O)(OPh)$_2$Cl, DCM diluted, DMAP 2. separation of α and β.

(31) A process for preparing D-glycero-D-manno-heptopyranose 1β,7-bisphosphate (JS6 or HBP-β), comprising a reaction sequence as outlined below

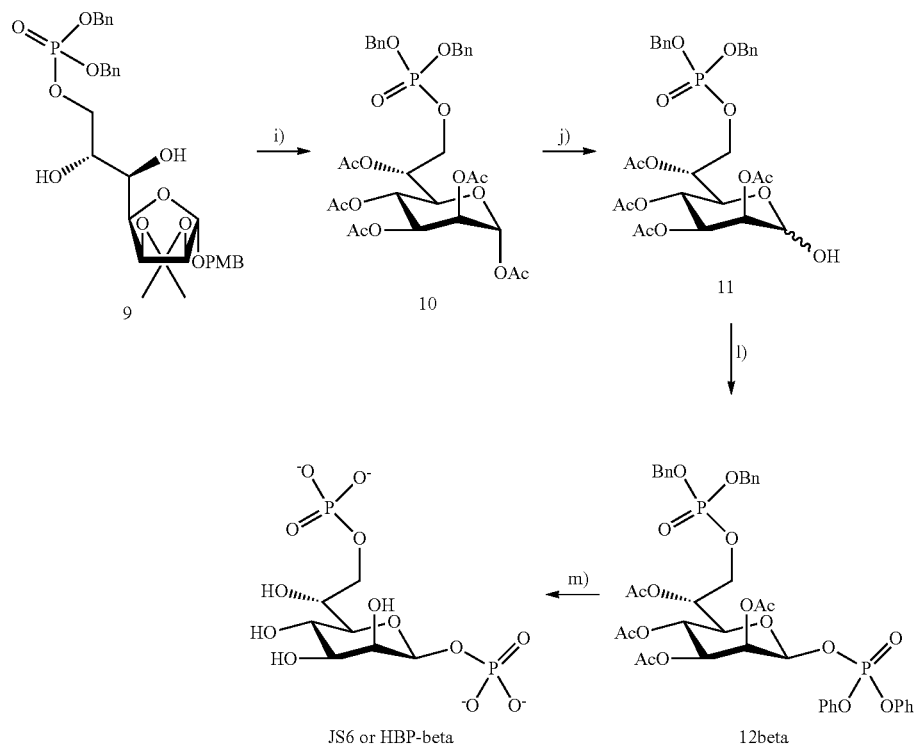
wherein: i) 1. TFA/water/DMC 2. acetic anhydride/pyridine (1/1) 3. separation of α and β; and j) DIPEA, ammonium acetate, DMF; l) 1. P(O)(OPh)₂Cl, DCM diluted, DMAP 2. separation of α and β; and m) 1. H₂, PtO₂ 2. H₂, Pd/C 3. Et₃N, water, MeOH.
(32) A process according to any one of (28) to (31) above, wherein compound 9 is obtained by the following reaction sequence:
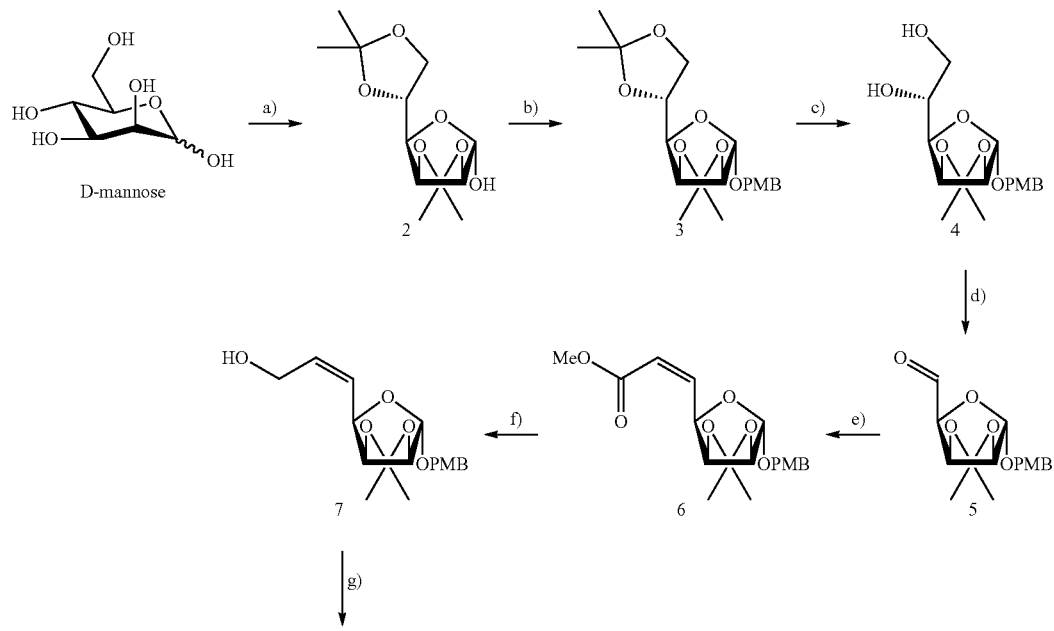

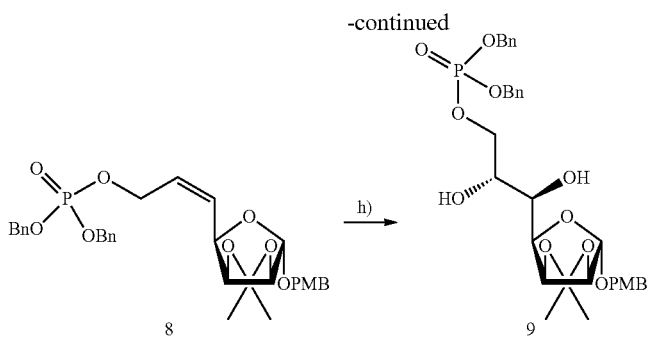
wherein: a) acetone/FeCl$_3$; b) NaH, PMBCl; c) acetic acid/water (4/1); d) NaIO$_4$; e) Ph$_3$PCHCOOMe; f) DIBAL; g) iPr$_2$NP(OBn)$_2$, tetrazole and then tBuOOH; and h) OsO$_4$, NMMO.
(33) A process for preparing D-glycero-D-manno-heptopyranose 1β,7-bisphosphate (JS6 or HBP-β), comprising the following reaction sequence:
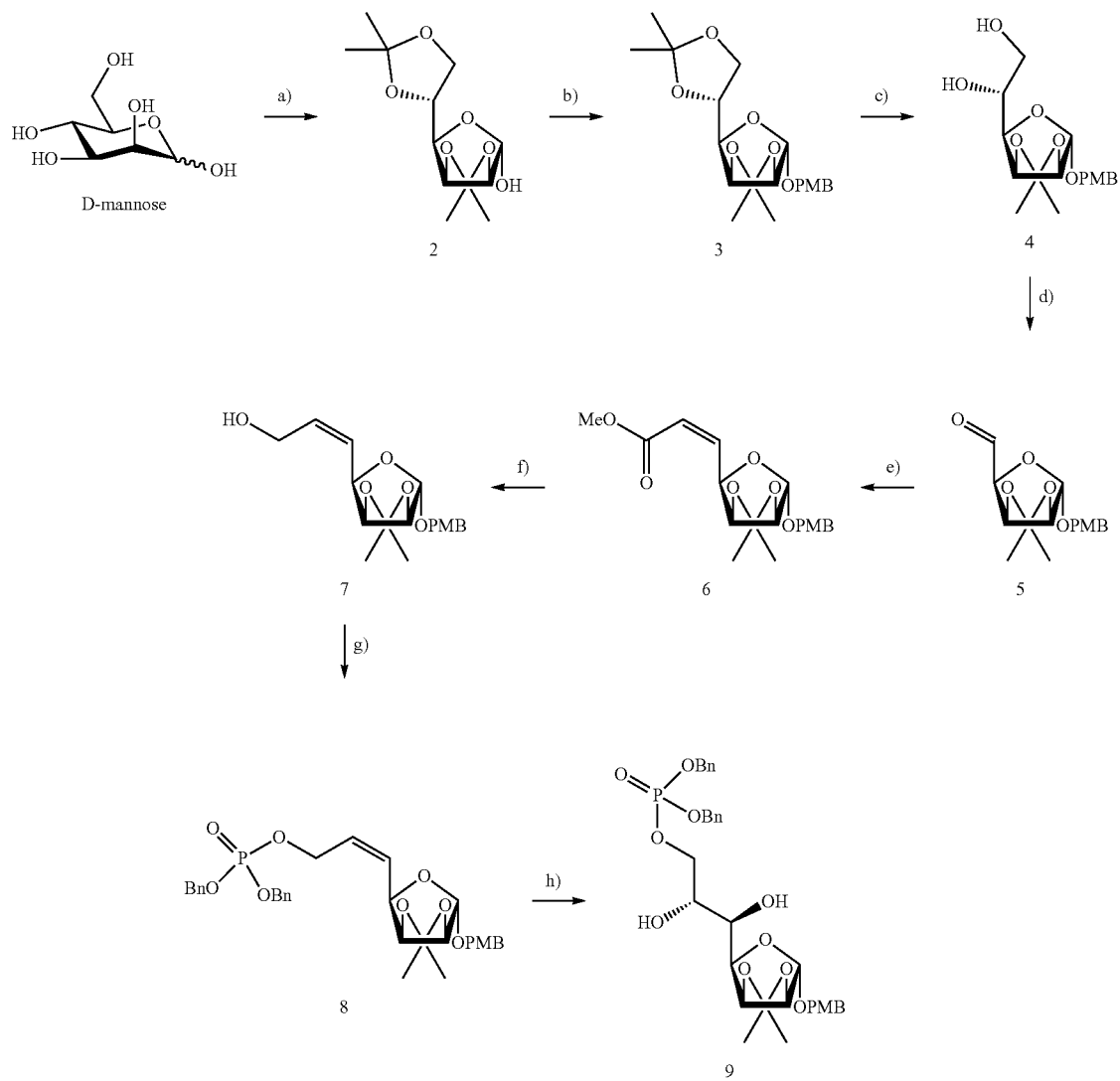

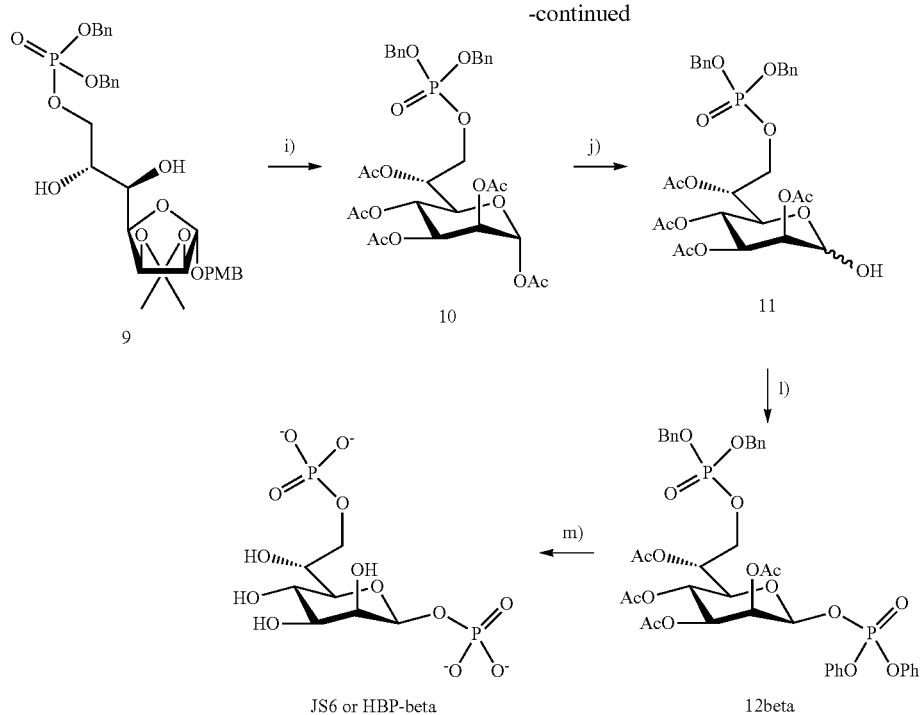

wherein: a) acetone/FeCl$_3$; b) NaH, PMBCl; c) acetic acid/water (4/1); d) NaIO$_4$; e) Ph$_3$PCHCOOMe; f) DIBAL; g) iPr$_2$NP(OBn)$_2$, tetrazole and then tBuOOH; and h) OSO$_4$ NMMO; i) 1. TFA/water/DMC 2. acetic anhydride/pyridine (1/1) 3. separation of α and β; and j) DIPEA, ammonium acetate, DMF; l) 1. P(O)(OPh)$_2$Cl, DCM diluted, DMAP 2. separation of α and β; and m) 1. H$_2$, PtO$_2$ 2. H$_2$, Pd/C 3. Et$_3$N, water, MeOH.

(34) A process for preparing D-glycero-D-manno-heptopyranose 1α,7-bisphosphate (JS5 or HBP-α), comprising a reaction step as outlined below

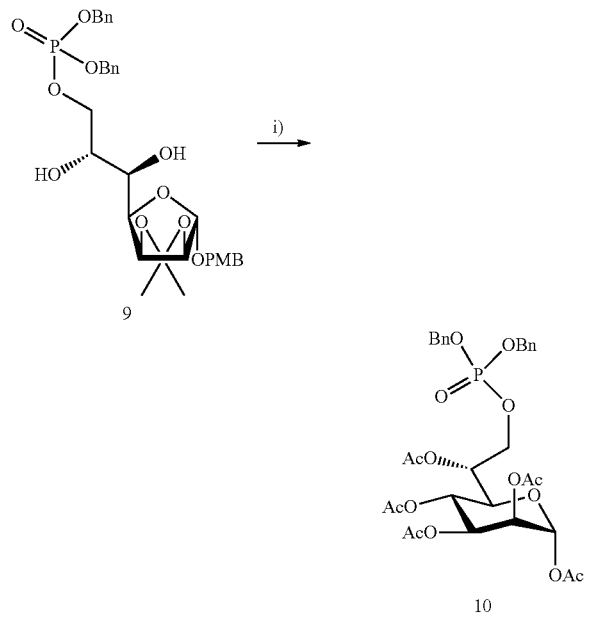

wherein: i) 1. TFA/water/DMC 2. acetic anhydride/pyridine (1/1) 3. separation of α and β.

(35) A process for preparing D-glycero-D-manno-heptopyranose 1α,7-bisphosphate (JS5 or HBP-α), comprising a reaction step as outlined below

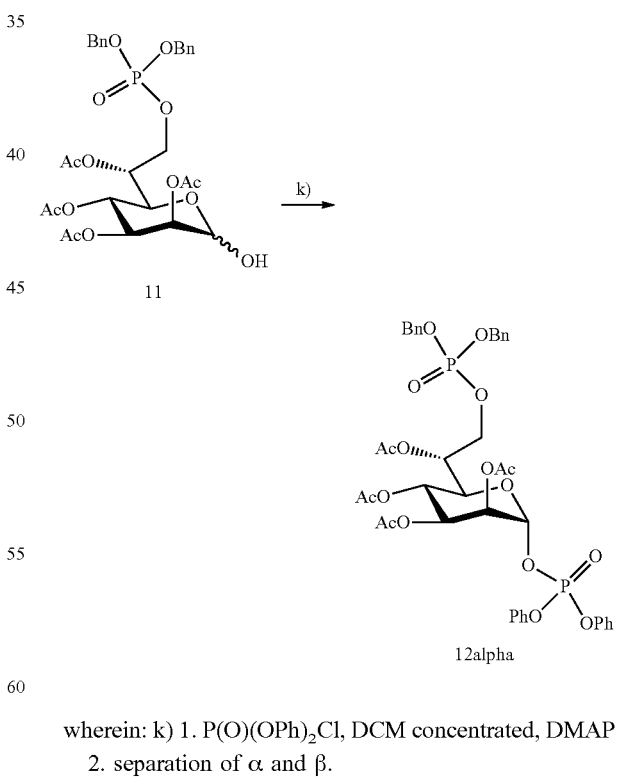

wherein: k) 1. P(O)(OPh)$_2$Cl, DCM concentrated, DMAP 2. separation of α and β.

(36) A process for preparing D-glycero-D-manno-heptopyranose 1α,7-bisphosphate (JS5 or HBP-α), comprising a reaction sequence as outlined below

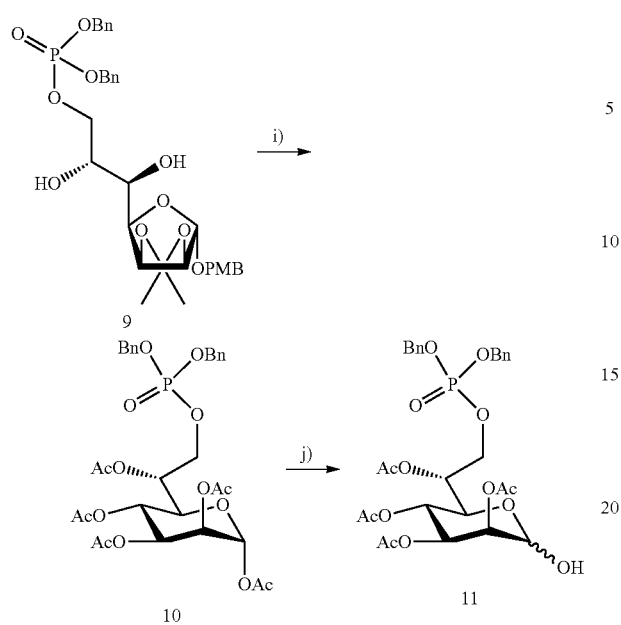
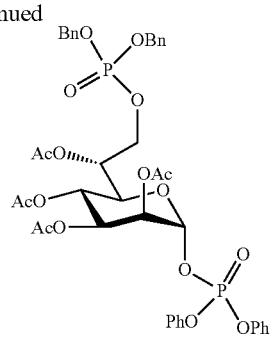
wherein: i) 1. TFA/water/DMC 2. acetic anhydride/pyridine (1/1) 3. separation of α and β; and k) 1. P(O)(OPh)₂Cl, DCM concentrated, DMAP 2. separation of α and β.
(37) A process for preparing D-glycero-D-manno-heptopyranose 1α,7-bisphosphate (JS5 or HBP-α), comprising a reaction sequence as outlined below
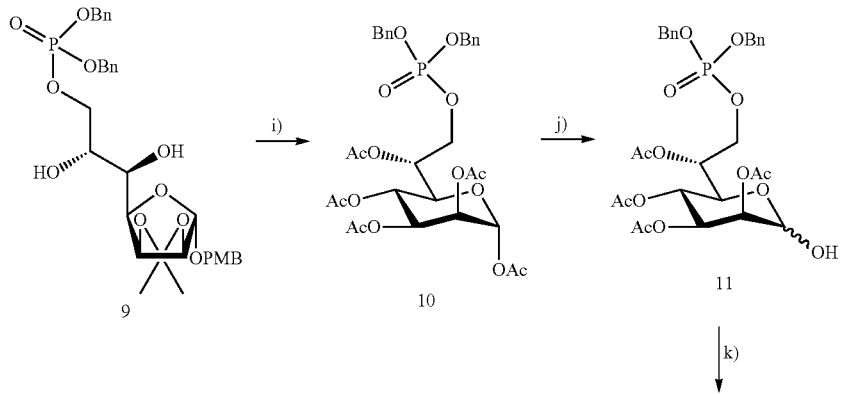
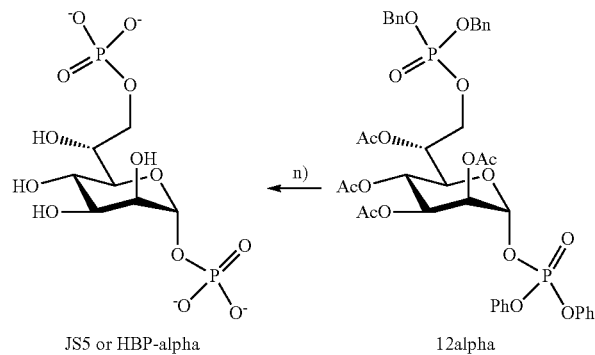

wherein: i) 1. TFA/water/DMC 2. acetic anhydride/pyridine (1/1) 3. separation of α and β; k) 1. P(O)(OPh)₂Cl, DCM concentrated, DMAP 2. separation of α and β; and n) 1. H₂, PtO₂ 2. H₂, Pd/C 3. Et₃N, water, MeOH.

(38) A process according to any one of (34) to (37) above, wherein compound 9 is obtained by the following reaction sequence

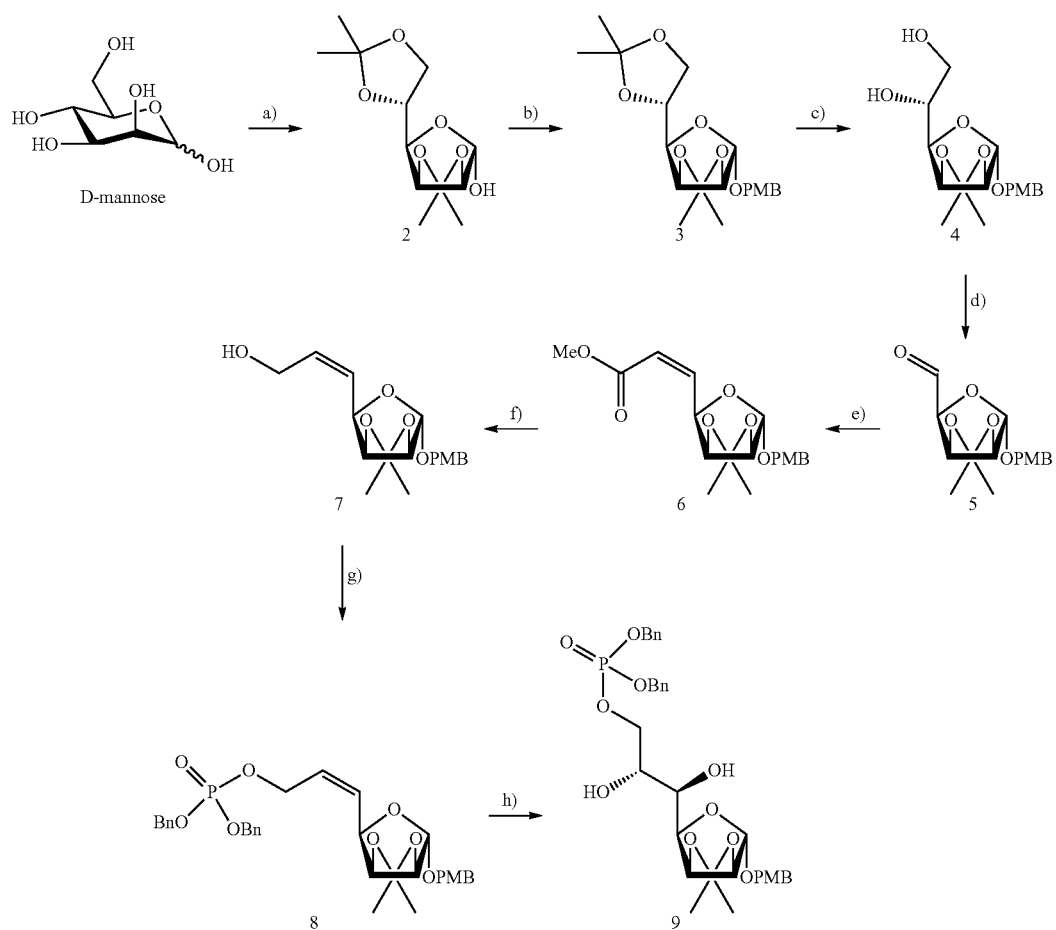

wherein: a) acetone/FeCl₃; b) NaH, PMBCl; c) acetic acid/water (4/1); d) NaIO₄; e) Ph₃PCHCOOMe; f) DIBAL; g) iPr₂NP(OBn)₂, tetrazole and then tBuOOH; and h) OSO₄, NMMO.

(39) A process for preparing D-glycero-D-manno-heptopyranose 1α,7-bisphosphate (JS5 or HBP-α), comprising the following reaction sequence:

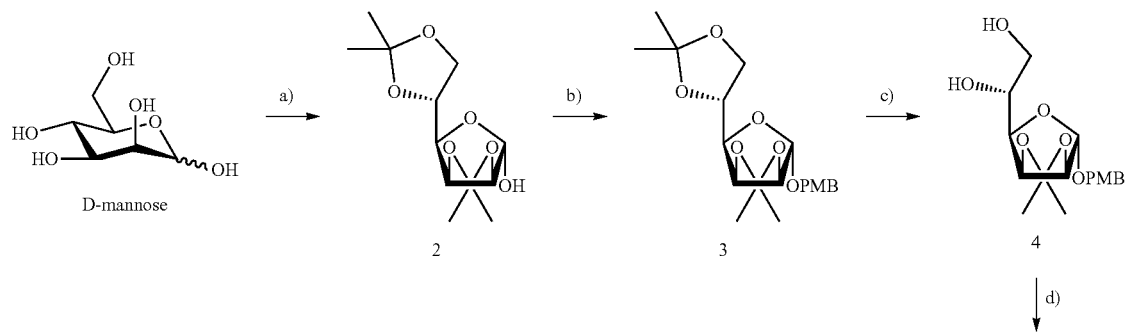

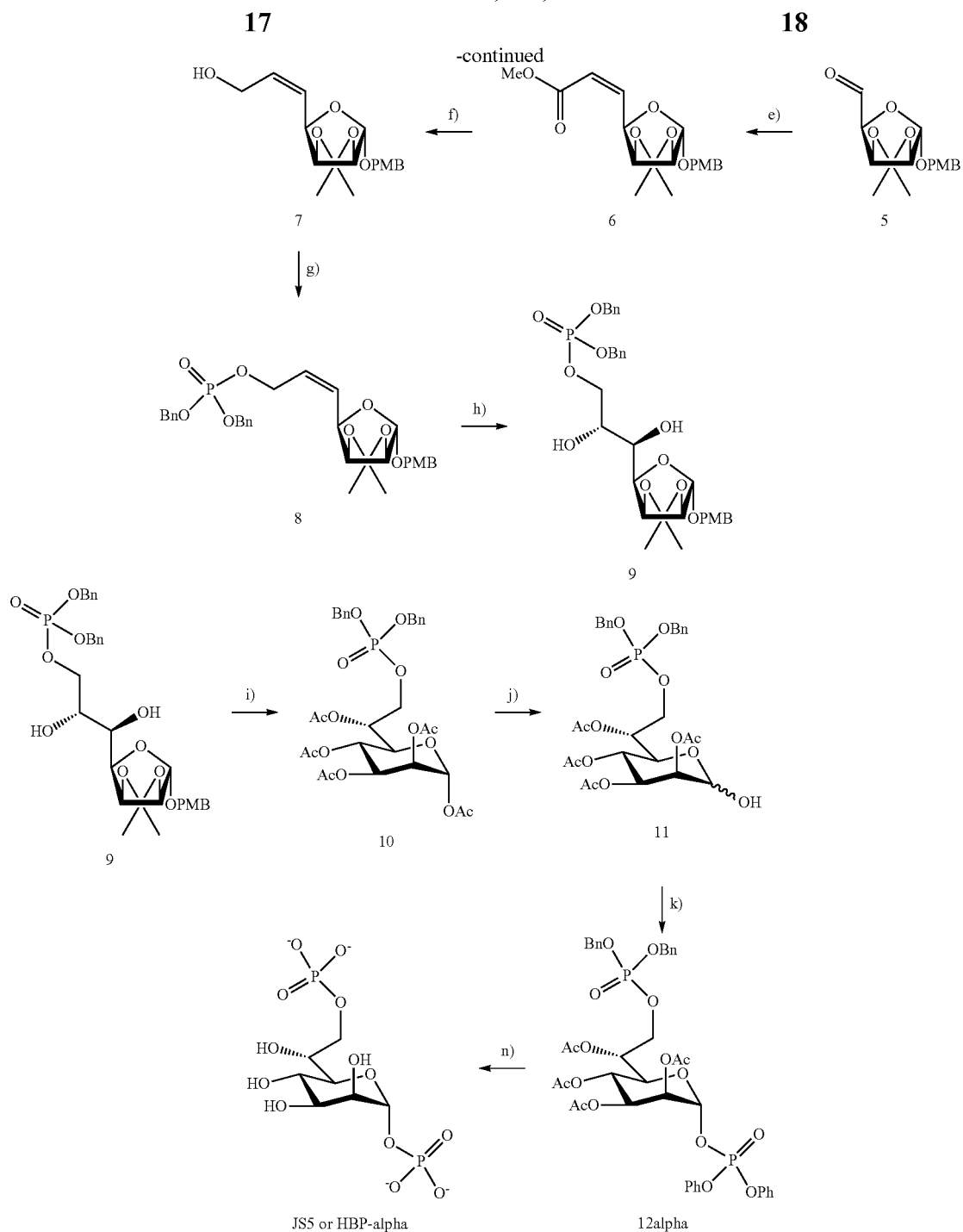

wherein: a) acetone/FeCl$_3$; b) NaH, PMBCl; c) acetic acid/water (4/1); d) NaIO$_4$; e) Ph$_3$PCHCOOMe; f) DIBAL; g) iPr$_2$NP(OBn)$_2$, tetrazole and then tBuOOH; and h) OsO$_4$, NMMO; i) 1. TFA/water/DMC 2. acetic anhydride/pyridine (1/1) 3. separation of α and β; and j) DIPEA, ammonium acetate, DMF; k) 1. P(O)(OPh)$_2$Cl, DCM concentrated, DMAP 2. separation of α and β; and n) 1. H$_2$, PtO$_2$ 2. H$_2$, Pd/C 3. Et$_3$N, water, MeOH.

(40) A process for preparing D-glycero-D-manno-heptopyranose 1β,7-bisphosphate (JS6 or HBP-β) and D-glycero-D-manno-heptopyranose 1α,7-bisphosphate (JS5 or HBP-α), comprising a reaction step as outlined below

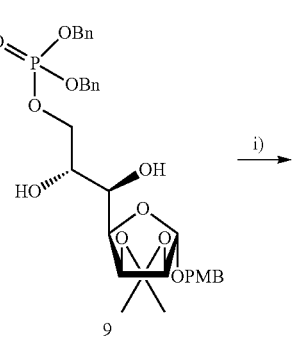

-continued

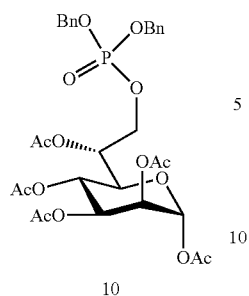

10 wherein: i) 1. TFA/water/DMC 2. acetic anhydride/pyridine (1/1) 3. separation of α and β.

(41) A process for preparing D-glycero-D-manno-heptopyranose 1β,7-bisphosphate (JS6 or HBP-β) and D-glycero-D-manno-heptopyranose 1α,7-bisphosphate (JS5 or HBP-α), comprising a reaction step as outlined below

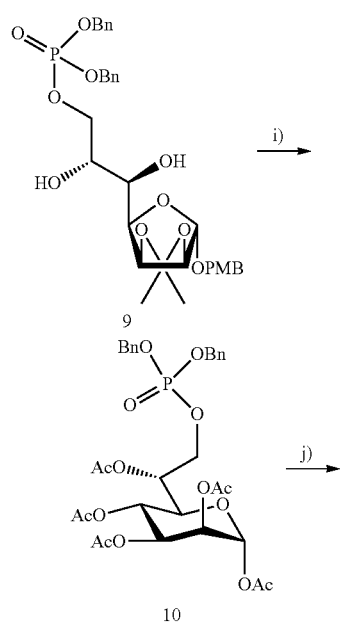

wherein: i) 1. TFA/water/DMC 2. acetic anhydride/pyridine (1/1) 3. separation of α and β; and j) DIPEA, ammonium acetate, DMF.

(42) A process according to (41) above, further comprising: dividing compound 11 into first and second portions, subjecting the first portion to a reaction sequence as outlined below to obtain D-glycero-D-manno-heptopyranose 1β,7-bisphosphate (JS6 or HBP-β), and subjecting the second portion to a reaction sequence as outlined below to obtain D-glycero-D-manno-heptopyranose 1α,7-bisphosphate (JS5 or HBP-α)

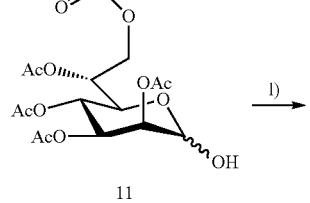

-continued

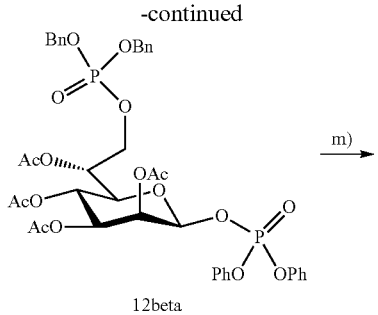

12beta

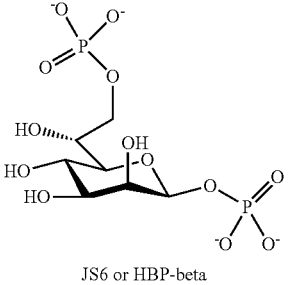

JS6 or HBP-beta

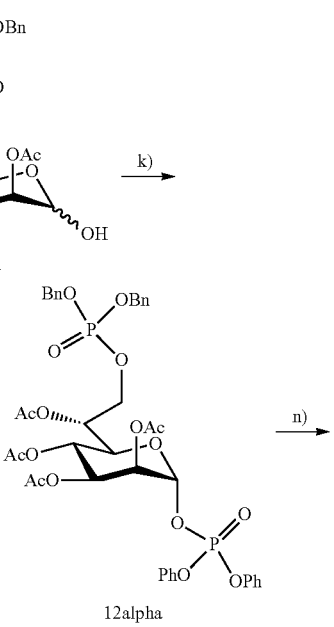

12alpha

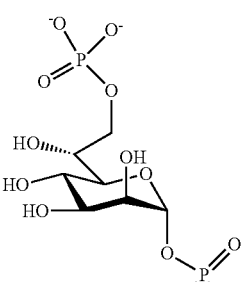

JS5 or HBP-alpha wherein: l) 1. P(O)(OPh)₂Cl, DCM diluted, DMAP 2. separation of α and β; and m) 1. H₂, PtO₂ 2. H₂, Pd/C 3. Et₃N, water, MeOH; k) 1. P(O)(OPh)₂Cl, DCM concentrated, DMAP 2. separation of α and β; and n) 1. H₂, PtO₂ 2. H₂, Pd/C 3. Et₃N, water, MeOH.

(43) A process for preparing D-glycero-D-manno-heptopyranose 1β,7-bisphosphate (JS6 or HBP-β) and D-glycero-D-manno-heptopyranose 1α,7-bisphosphate (JS5 or HBP-α), comprising a reaction sequence as outlined below
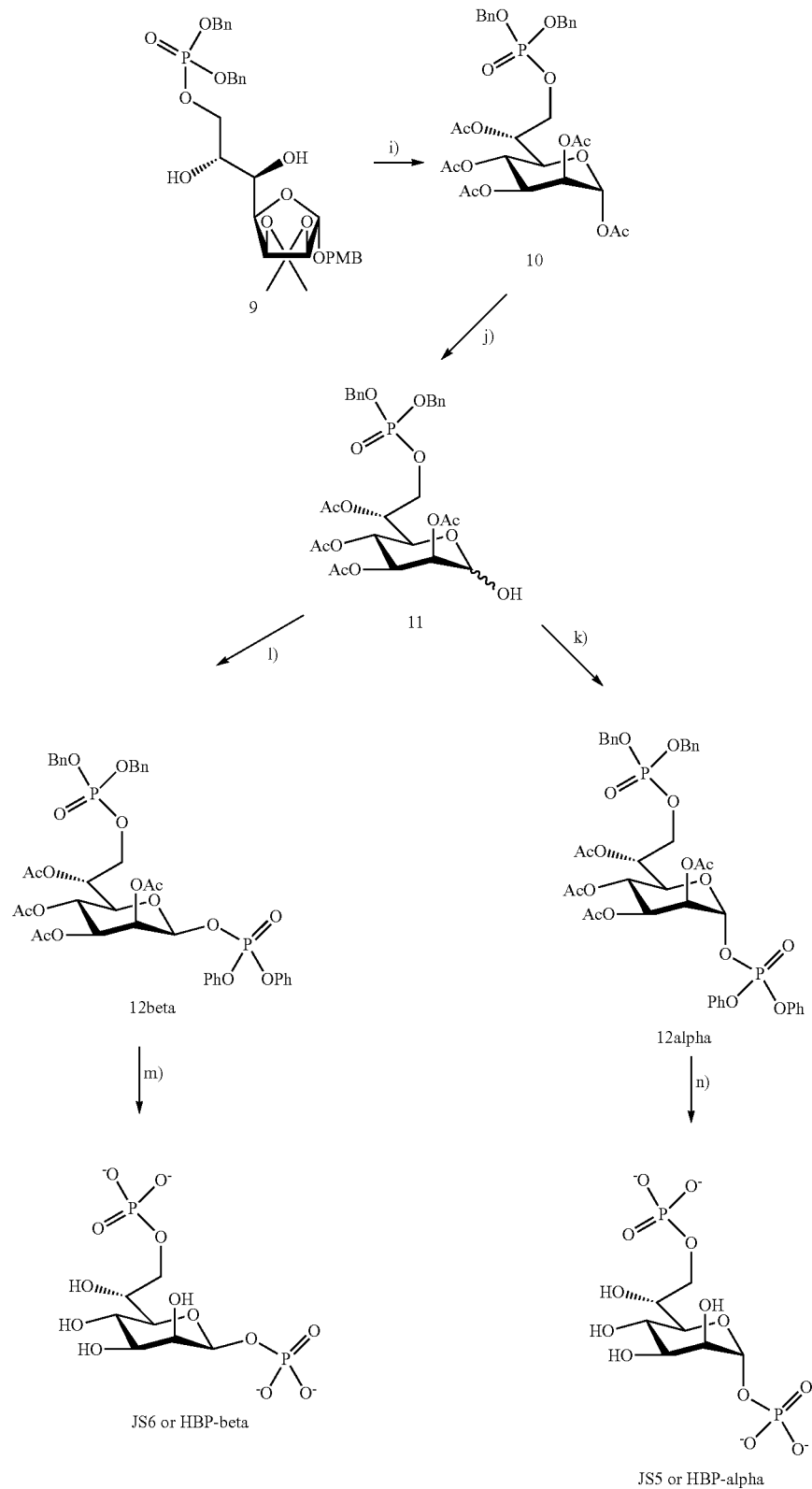

wherein: i) 1. TFA/water/DMC 2. acetic anhydride/pyridine (1/1) 3. separation of α and β; k) 1. P(O)(OPh)₂Cl, DCM concentrated, DMAP 2. separation of α and β; n) 1. H₂, PtO₂ 2. H₂, Pd/C 3. Et₃N, water, MeOH; 1) 1. P(O)(OPh)₂Cl, DCM diluted, DMAP 2. separation of α and β; and m) 1. H₂, PtO₂ 2. H₂, Pd/C 3. Et₃N, water, MeOH.

(44) A process for preparing D-glycero-D-manno-heptopyranose 1β,7-bisphosphate (JS6 or HBP-β) and D-glycero-D-manno-heptopyranose 1α,7-bisphosphate (JS5 or HBP-β), comprising the following reaction sequence:

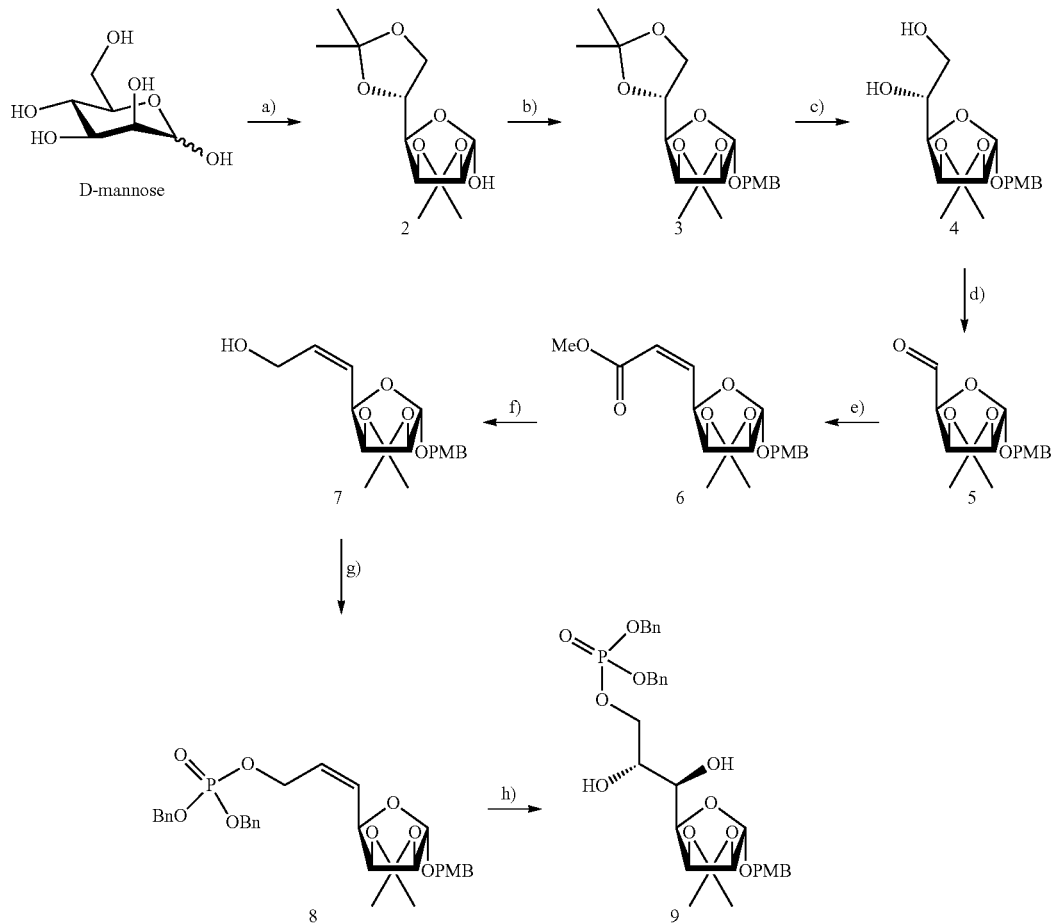

wherein: a) acetone/FeCl₃; b) NaH, PMBCl; c) acetic acid/water (4/1); d) NaIO₄; e) Ph₃PCHCOOMe; f) DIBAL; g) iPr₂NP(OBn)₂, tetrazole and then tBuOOH; and h) OsO₄, NMMO; i) 1. TFA/water/DMC 2. acetic anhydride/pyridine (1/1) 3. separation of α and β; and j) DIPEA, ammonium acetate, DMF; k) 1. P(O)(OPh)₂Cl, DCM concentrated, DMAP 2. separation of α and β; n) 1. H₂, PtO₂ 2. H₂, Pd/C 3. Et₃N, water, MeOH; 1) 1. P(O)(OPh)₂Cl, DCM diluted, DMAP 2. separation of α and β; and m) 1. H₂, PtO₂ 2. H₂, Pd/C 3. Et₃N, water, MeOH.

(45) A phosphorylated heptose compound obtained by the process as defined in any one of (1) to (24) and (28) to (44) above or a derivative or an analogue thereof, with the proviso that the compound is different from D-glycero-D-manno-heptopyranose 1β,7-bisphosphate (HBP-β) and D-glycero-D-manno-heptopyranose 1α,7-bisphosphate (HBP-α).

(46) A pharmaceutical composition comprising a phosphorylated heptose compound as defined in (45) above and a pharmaceutically acceptable carrier.

(47) A device coated or filled with a phosphorylated heptose compound as defined in (45) above or a reaction product as defined in (25) or (26) above, with the proviso that the compound is different from D-glycero-D-manno-heptopyranose 1β,7-bisphosphate (HBP-β) and D-glycero-D-manno-heptopyranose 1α,7-bisphosphate (HBP-α).

(48) Use of an effective amount of a phosphorylated heptose compound as defined in claim 45, a reaction product as defined in (25) or (26) above, or a pharmaceutical composition as defined in (45) or (27) above, for modulating an immune response in a subject.

(49) Use of a phosphorylated heptose compound as defined in (45) above or a reaction product as defined in (25) or (26) above, in the preparation of a medicament for modulating an immune response in a subject.

(50) A method of modulating an immune response in a subject, comprising administering to the subject an effective amount of a phosphorylated heptose compound as defined in (45) above, a reaction product as defined in (25) or (26) above, or a pharmaceutical composition as defined in (45) or (27) above.

(51) A phosphorylated heptose compound as defined in (45) above, a reaction product as defined in (25) or (26) above or a pharmaceutical composition as defined in (46) or (27) above, for use in modulating an immune response in a subject.

(52) A use as defined in (48) or (49) above or a method as defined in (50) above, wherein the immune response of the subject is enhanced.

(53) A use as defined in (48) or (49) above or a method as defined in (50) above, further comprising use of an immunogen.

(54) A use or method according to (53) above, wherein the immunogen is in a vaccine composition.

(55) A use or method according to (53) above, wherein the immunogen is an antigen derived from a bacteria, virus or other pathogen.

(56) A use as defined in (48) or (49) above or a method as defined in (50) above, comprising treating or preventing a bacterial, viral or parasitic infection.

(57) A use as defined in (48) or (49) above or a method as defined in (50) above, comprising treating or preventing a bacterial by Gram-negative bacteria.

(58) A use as defined in (48) or (49) above or a method as defined in (50) above, comprising treating or preventing a bacterial by Gram-positive bacteria.

(59) A use or method according to (57) above, wherein the Gram-negative bacteria are selected from the group of bacteria consisting of *Neisseria, Escherichia, Klebsiella, Salmonella, Shigella, Vibrio, Helicobacter, Pseudomonas, Burkholderia, Haemophilus, Moraxella, Bordetella, Francisella, Pasteurella, Borrelia, Campylobacter, Yersinia, Rickettsia, Treponema, Chlamydia* and *Brucella*.

(60) A use or method according to (58) above, wherein the Gram-positive bacteria are selected from the group of bacteria consisting of *Staphylococcus, Streptococcus, Listeria, Corynebacterium, Enterococcus, Clostridium* and *Mycobacterium*.

(61) A use as defined in (48) or (49) above or a method as defined in (50) above, comprising treating Human Immunodeficiency virus (HIV).

(62) A use or method according to (61) above, wherein the use of the phosphorylated heptose compound, the reaction product or the pharmaceutical composition induces HIV gene expression from latently infected cells.

(63) A use or method according to (56) above, wherein the parasitic infection is caused by a parasite selected from the group of parasites consisting of *Leishmania, Plasmodium, Toxoplasma, Trypanosoma* and *Schistosoma*.

(64) A use as defined in (48) or (49) above or a method as defined in (50) above, comprising treating a cancer.

(65) A use as defined in (48) or (49) above or a method as defined in (50) above, comprising a direct use of the phosphorylated heptose compound, the reaction product or the pharmaceutical composition on cancer cells.

(66) A use as defined in (48) or (49) above or a method as defined in (50) above, comprising preventing, treating, ameliorating, or inhibiting an injury, disease, disorder or condition wherein modulation of the immune response is beneficial.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 28: A) $^1$H NMR of compound 12a (Scheme 2) B) $^{13}$C NMR of compound 12a C) $^{31}$P NMR of compound 12a.

DESCRIPTION OF ILLUSTRATIVE EMBODIMENTS

Figure 1:
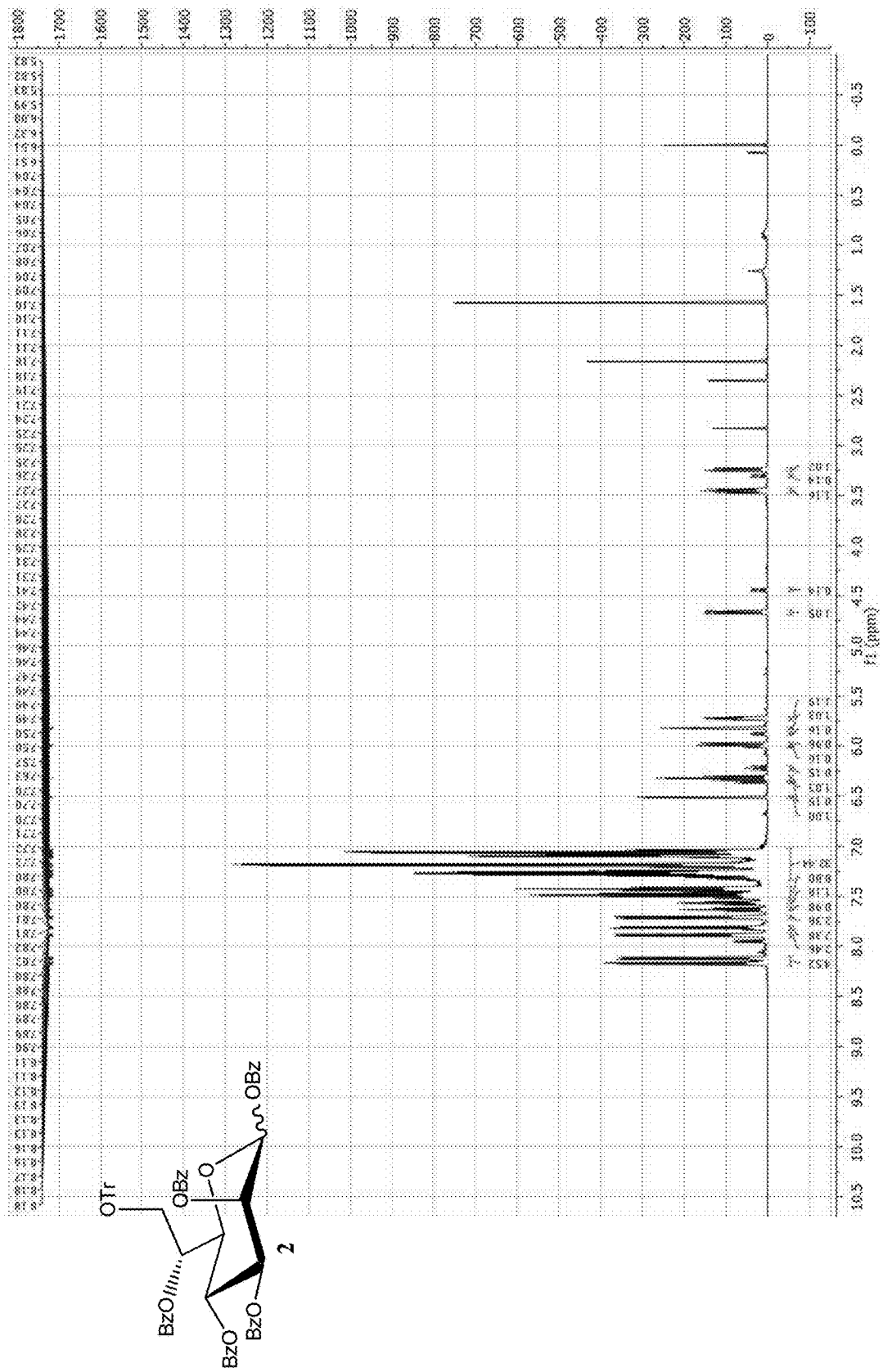
FIG. 1: $^1$H NMR of compound 2 (Scheme 1) at 25° C.
Figure 2:
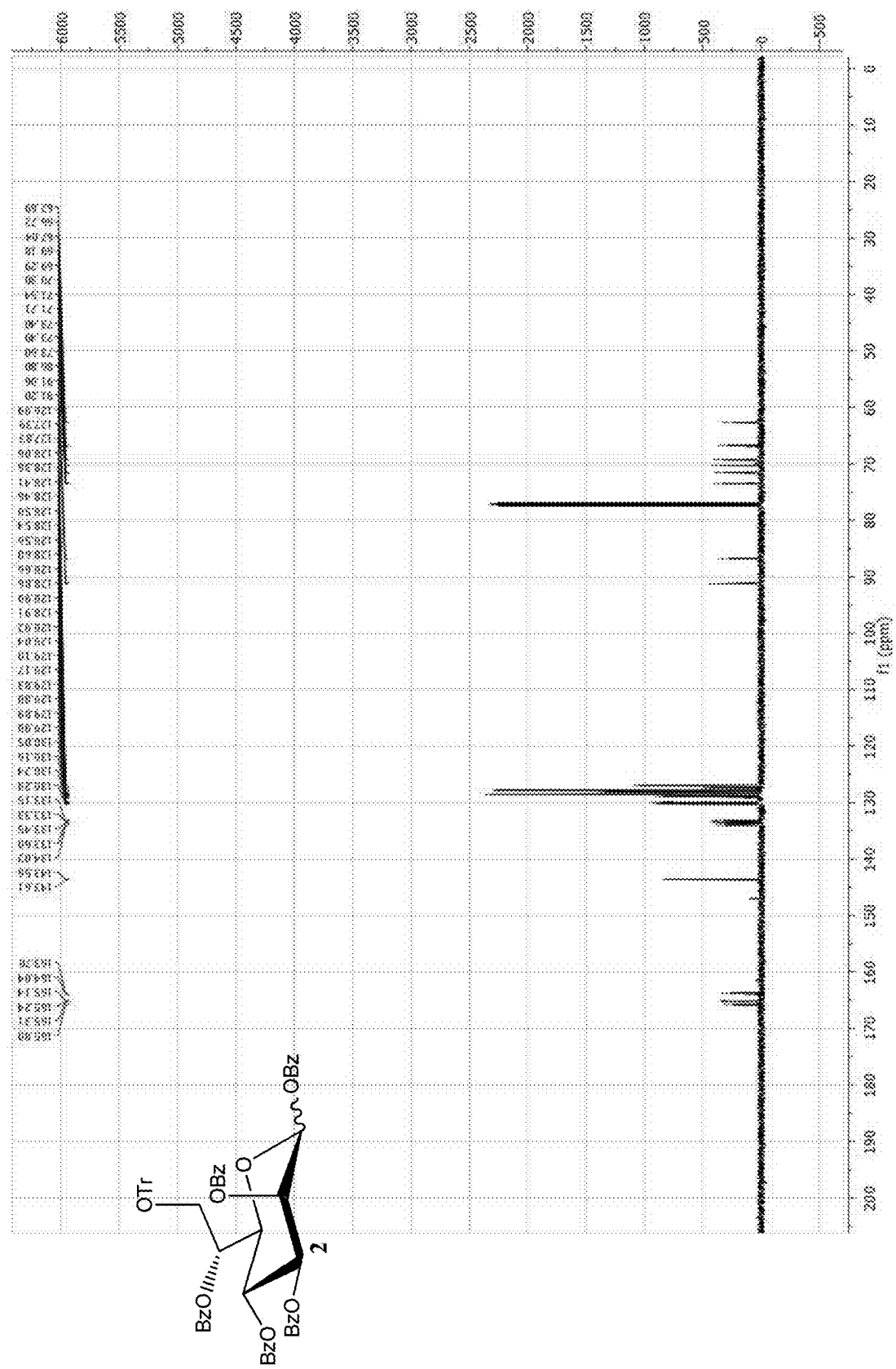
FIG. 2: $^{13}$C NMR of compound 2 (Scheme 1) at 25° C.
Figure 3:
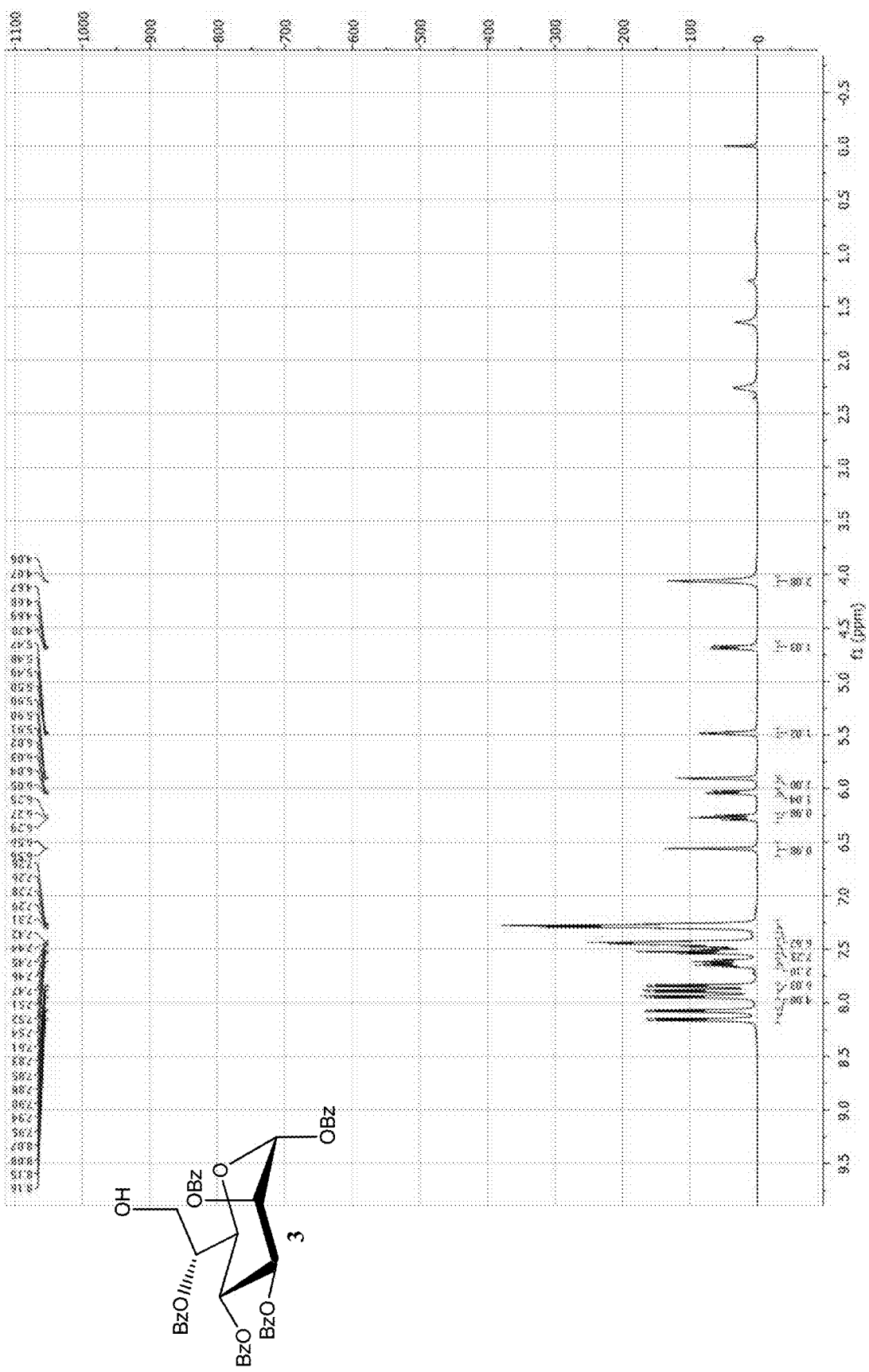
FIG. 3: $^1$H NMR of compound 3 (α; Scheme 1) at 25° C.
Figure 4:
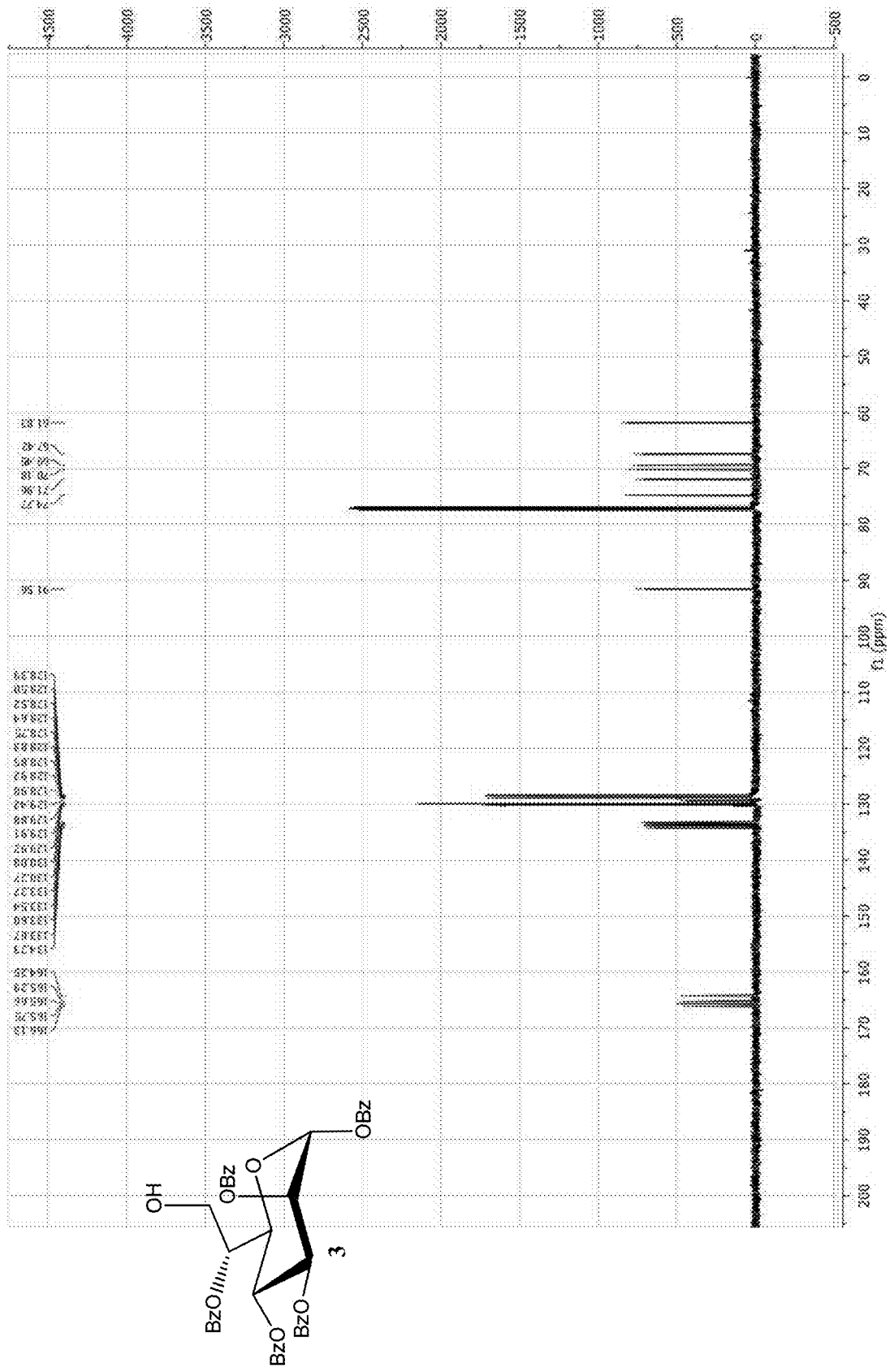
FIG. 4: $^{13}$C NMR of compound 3 (α; Scheme 1) at 25° C.
Figure 5:
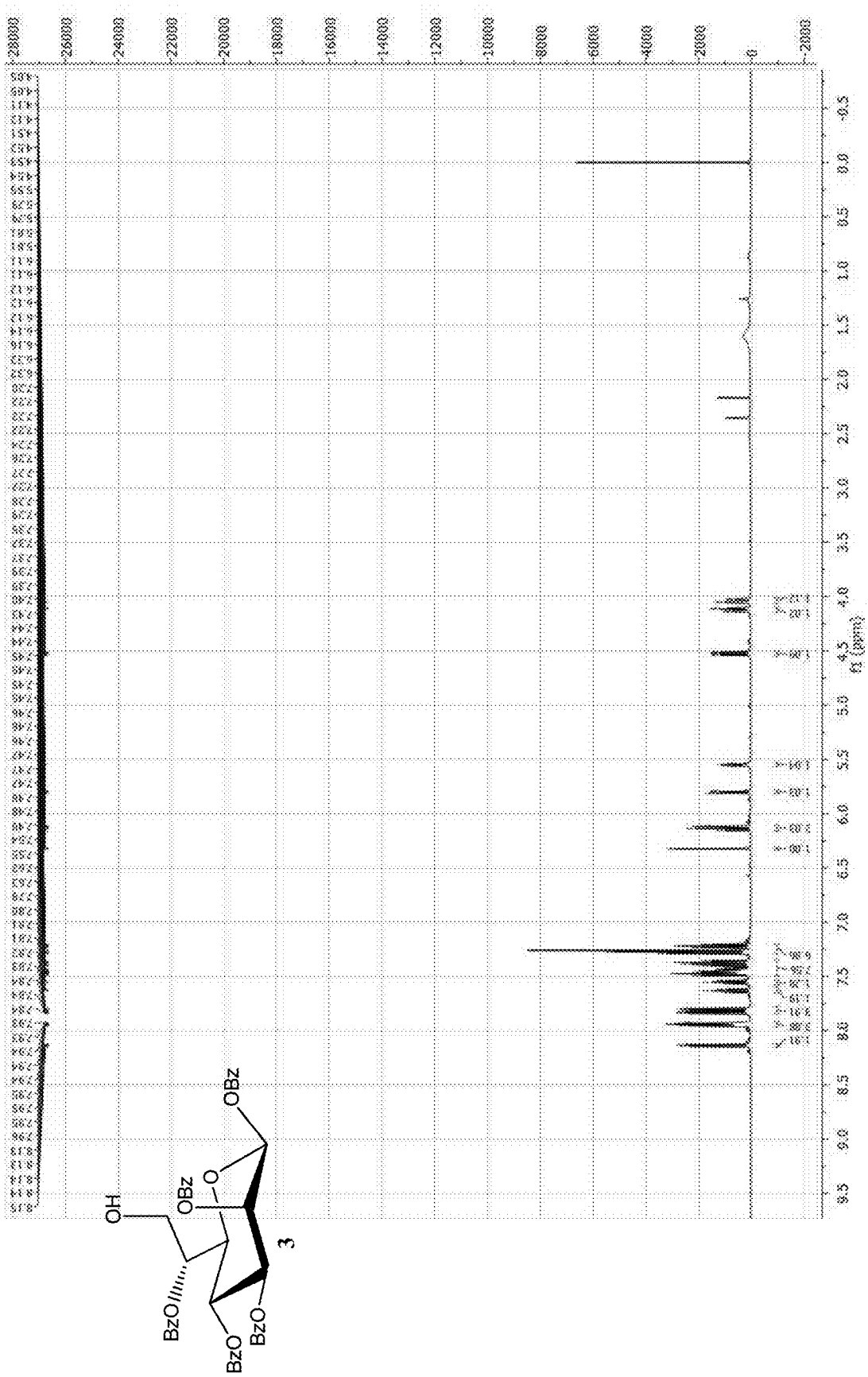
FIG. 5: $^1$H NMR of compound 3 (β; Scheme 1) at 25° C.
Figure 6:
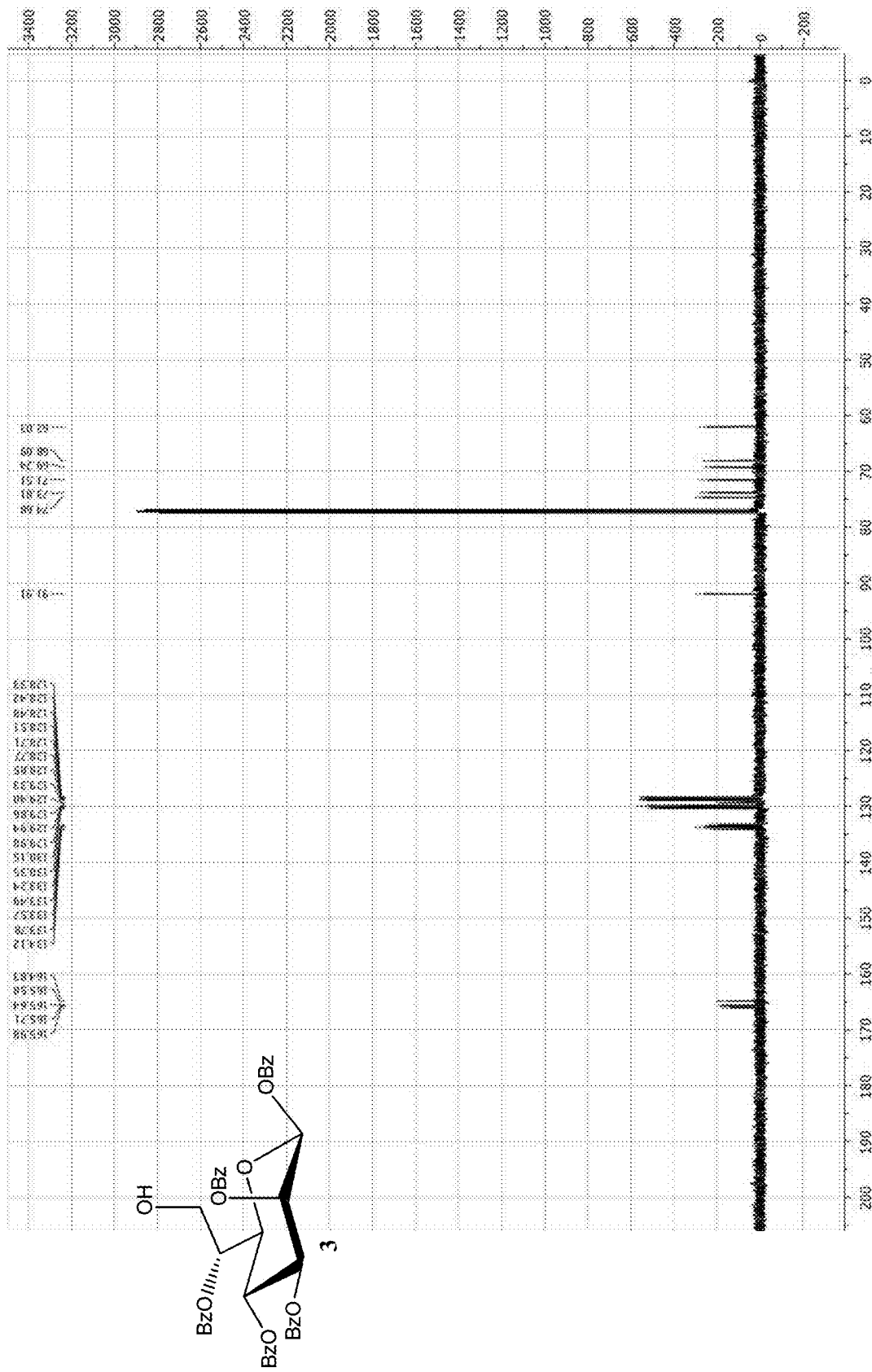
FIG. 6: $^{13}$C NMR of compound 3 (β; Scheme 1) at 25° C.
Figure 7:
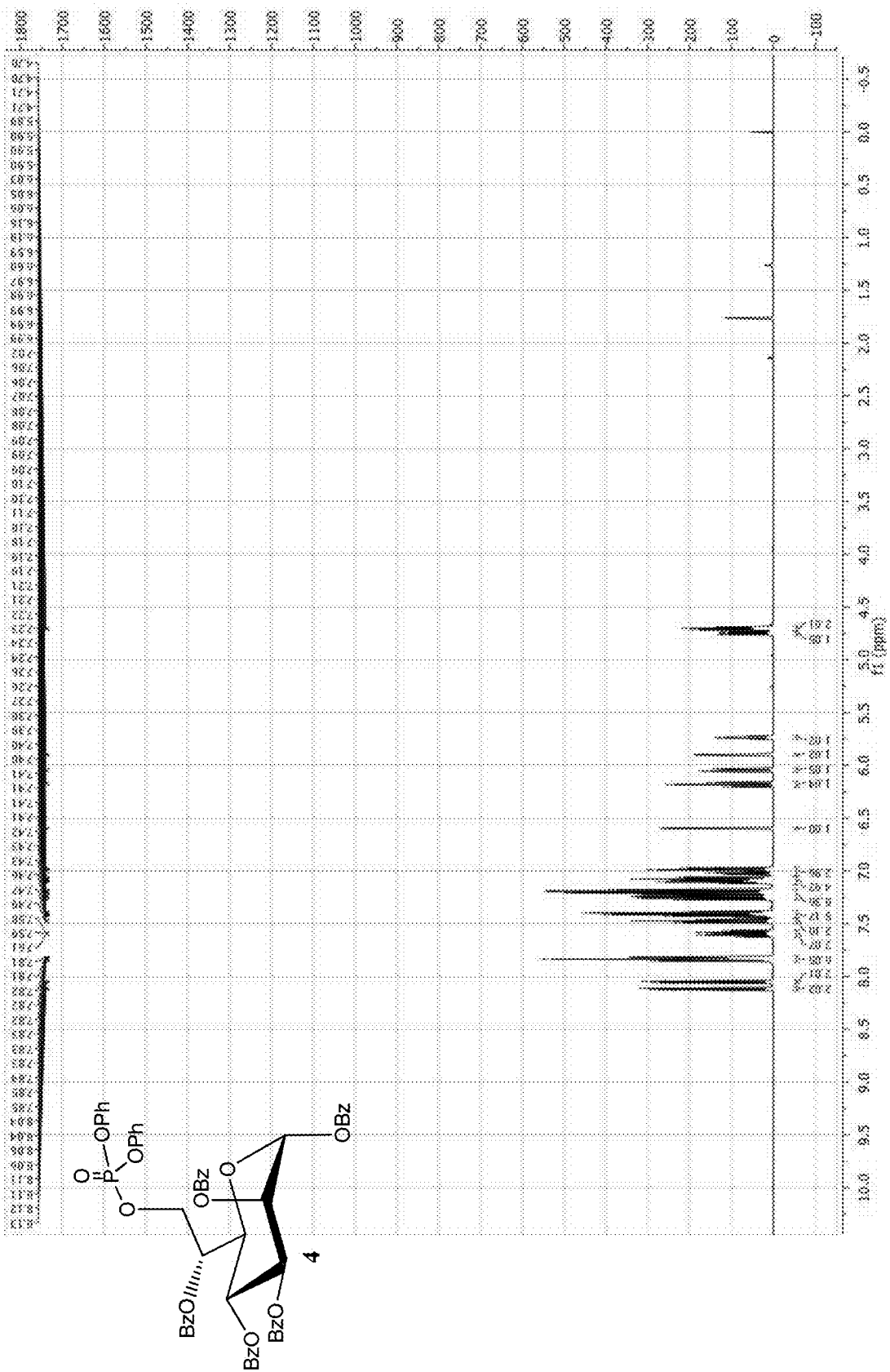
FIG. 7: $^1$H NMR of compound 4 (Scheme 1) at 25° C.
Figure 8:
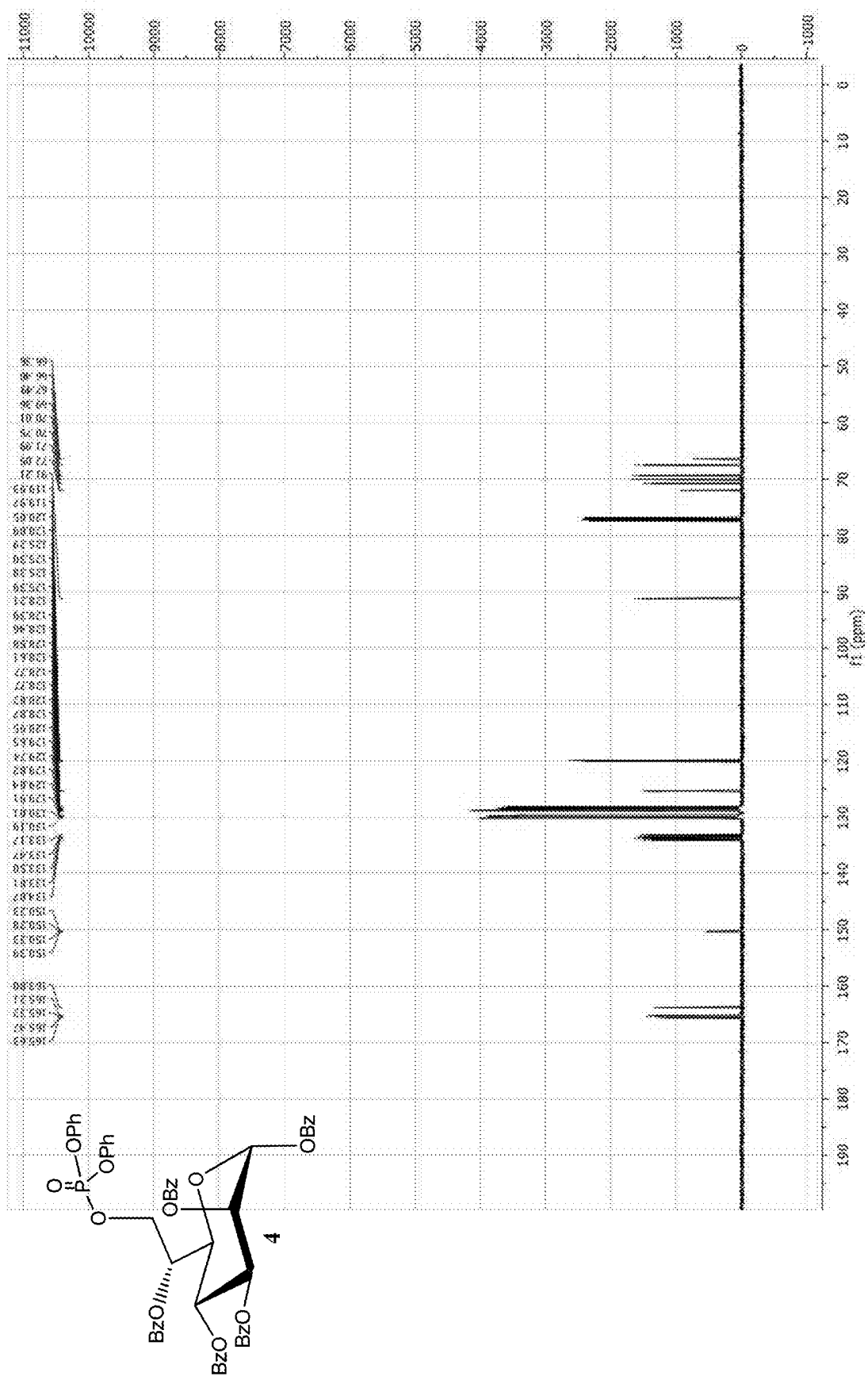
FIG. 8: $^{13}$C NMR of compound 4 (Scheme 1) at 25° C.
Figure 9:
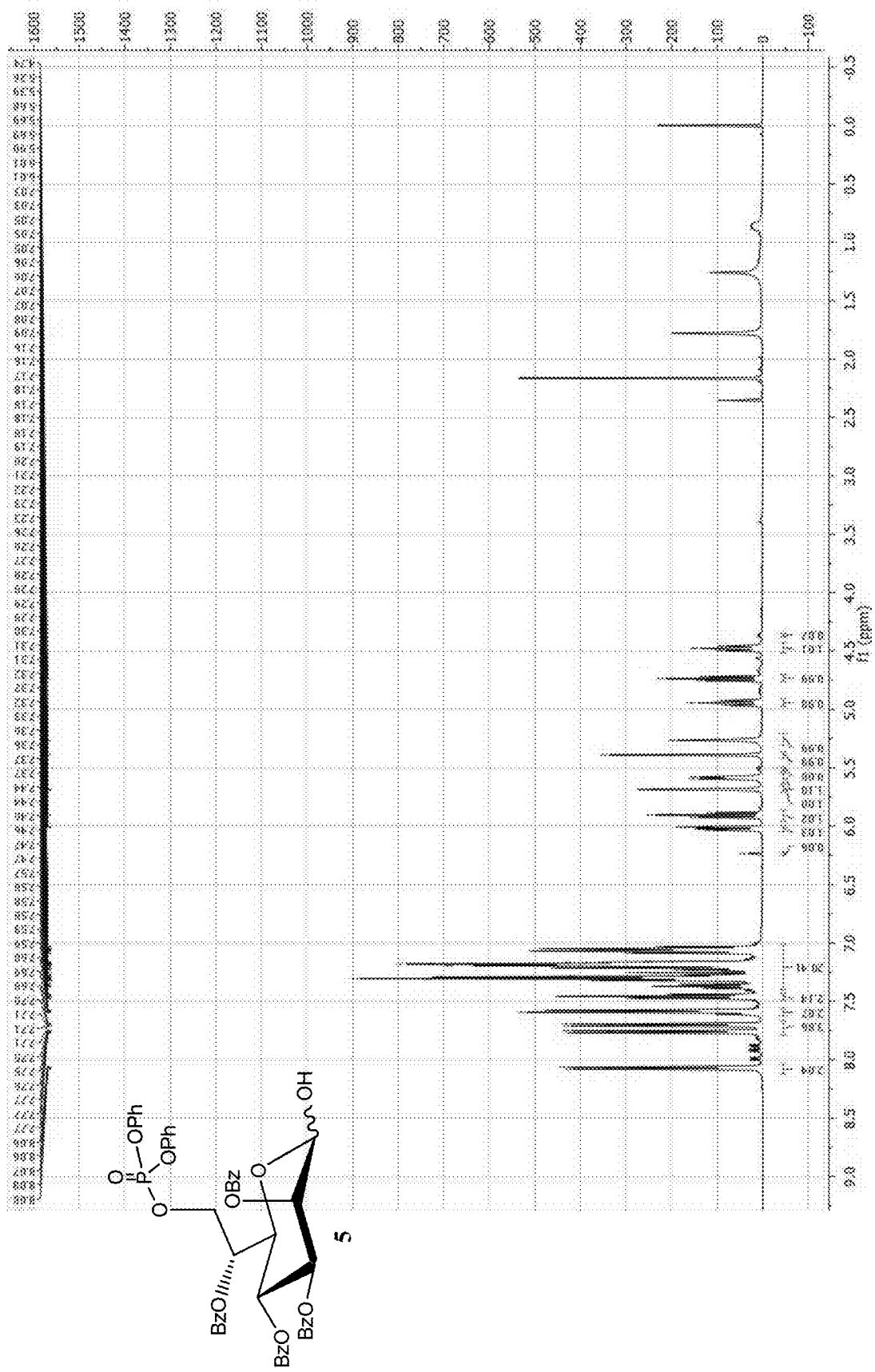
FIG. 9: $^1$H NMR of compound 5 (Scheme 1) at 25° C.
Figure 10:
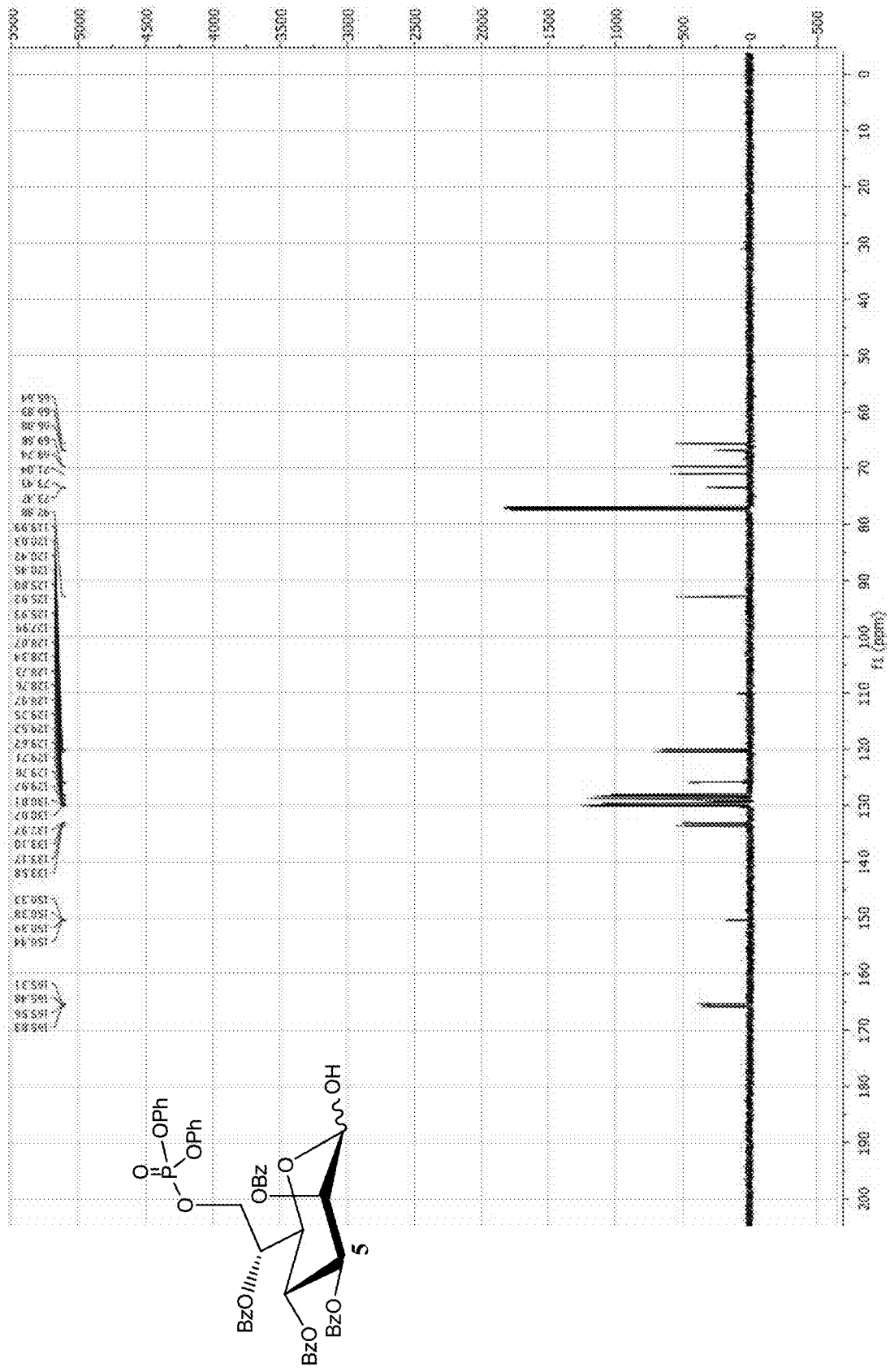
FIG. 10: $^{13}$C NMR of compound 5 (Scheme 1) at 25° C.
Figure 11:
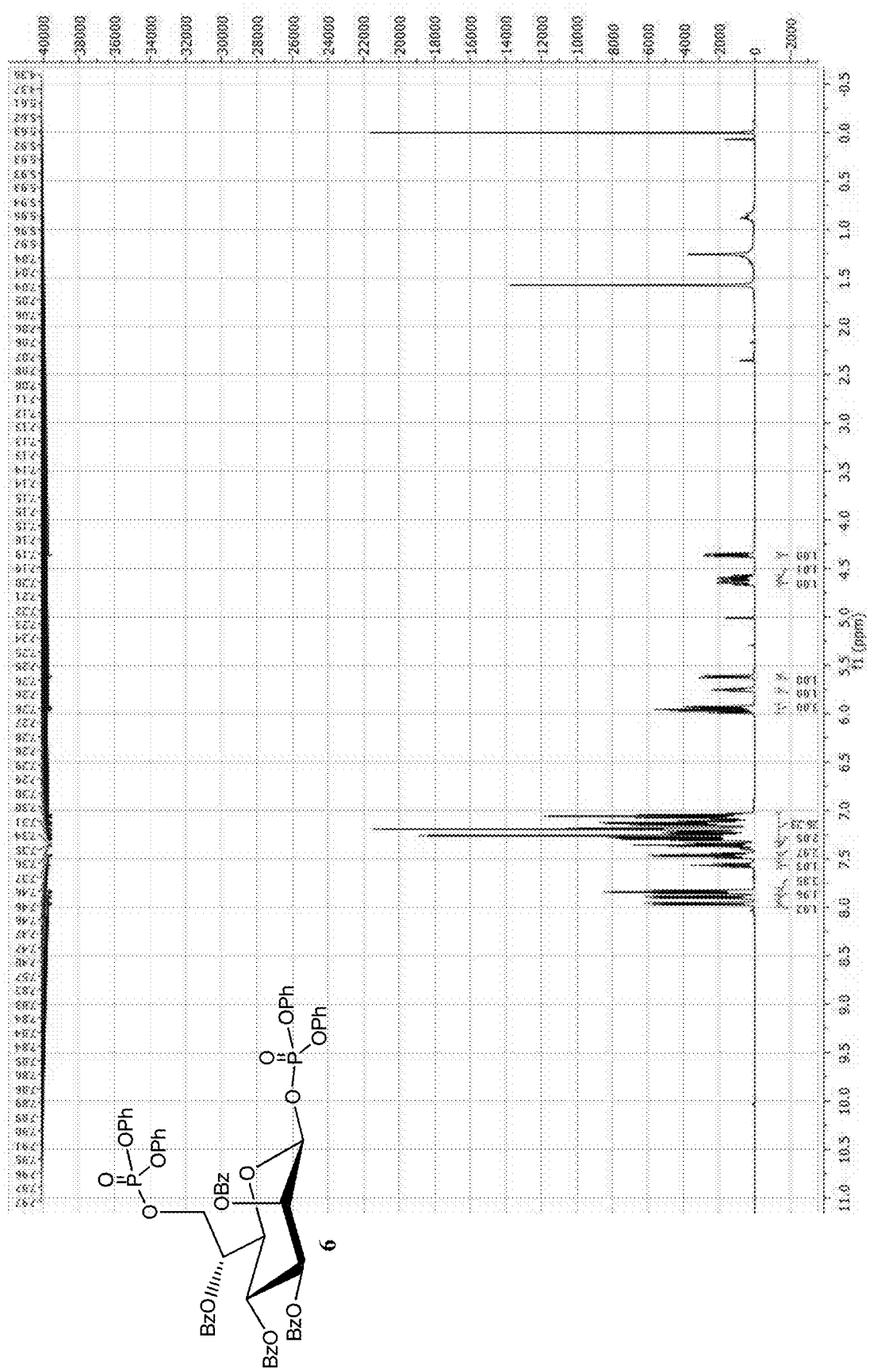
FIG. 11: $^1$H NMR of compound 6 (β; Scheme 1) at 25° C.
Figure 12:
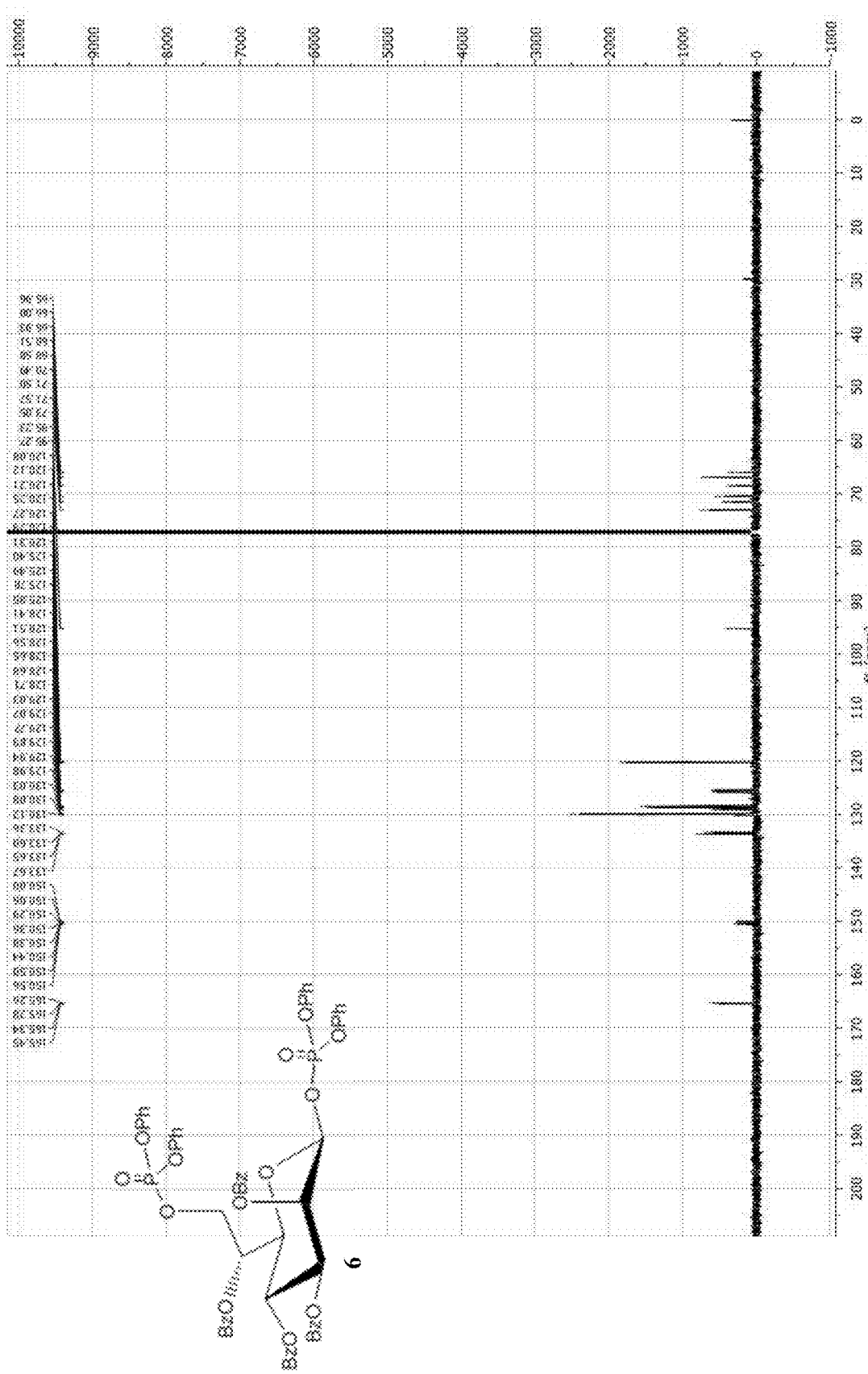
FIG. 12: $^{13}$C NMR of compound 6 (β; Scheme 1) at 25° C.
Figure 13:
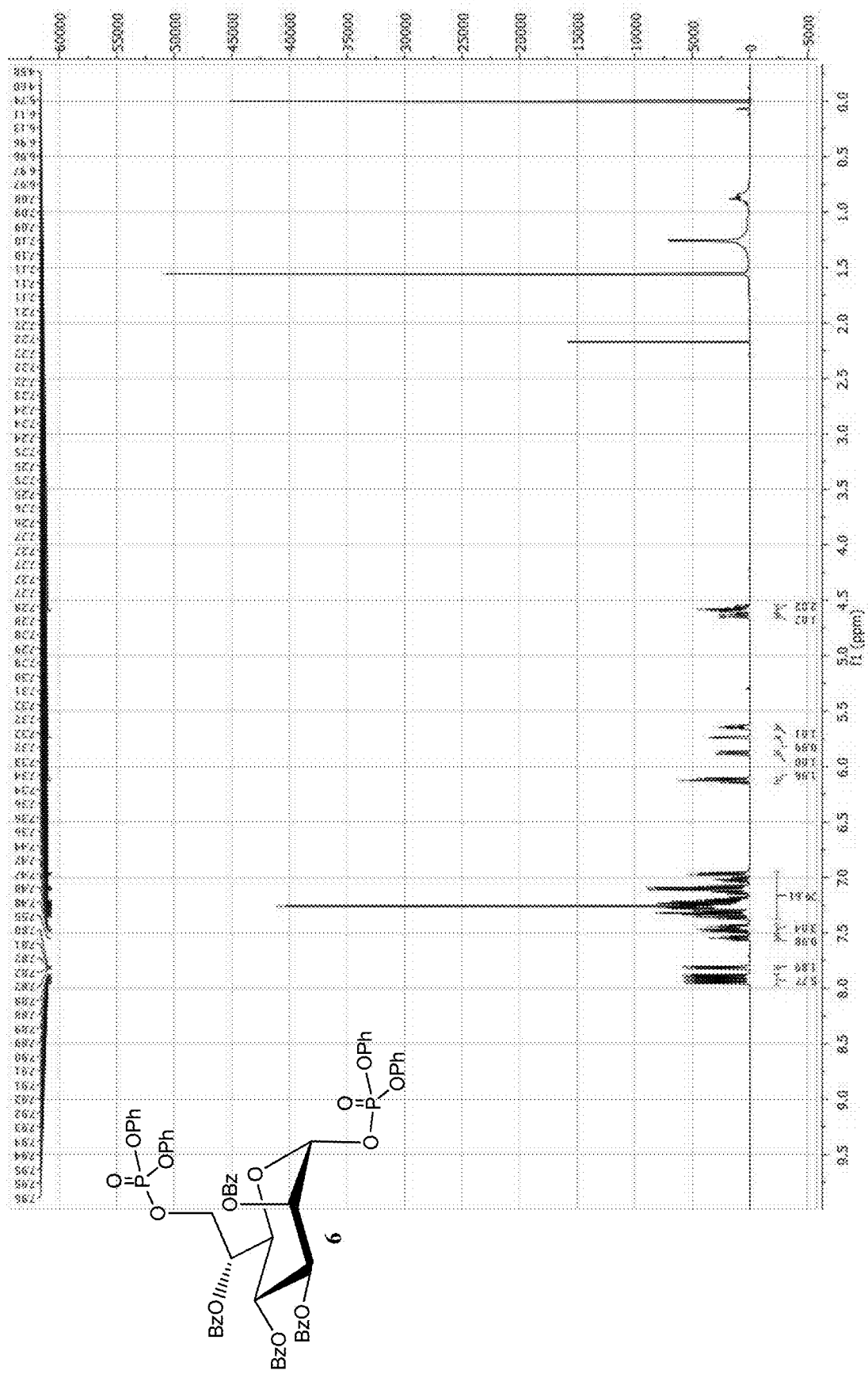
FIG. 13: $^1$H NMR of compound 6 (α; Scheme 1) at 25° C.
Figure 14:
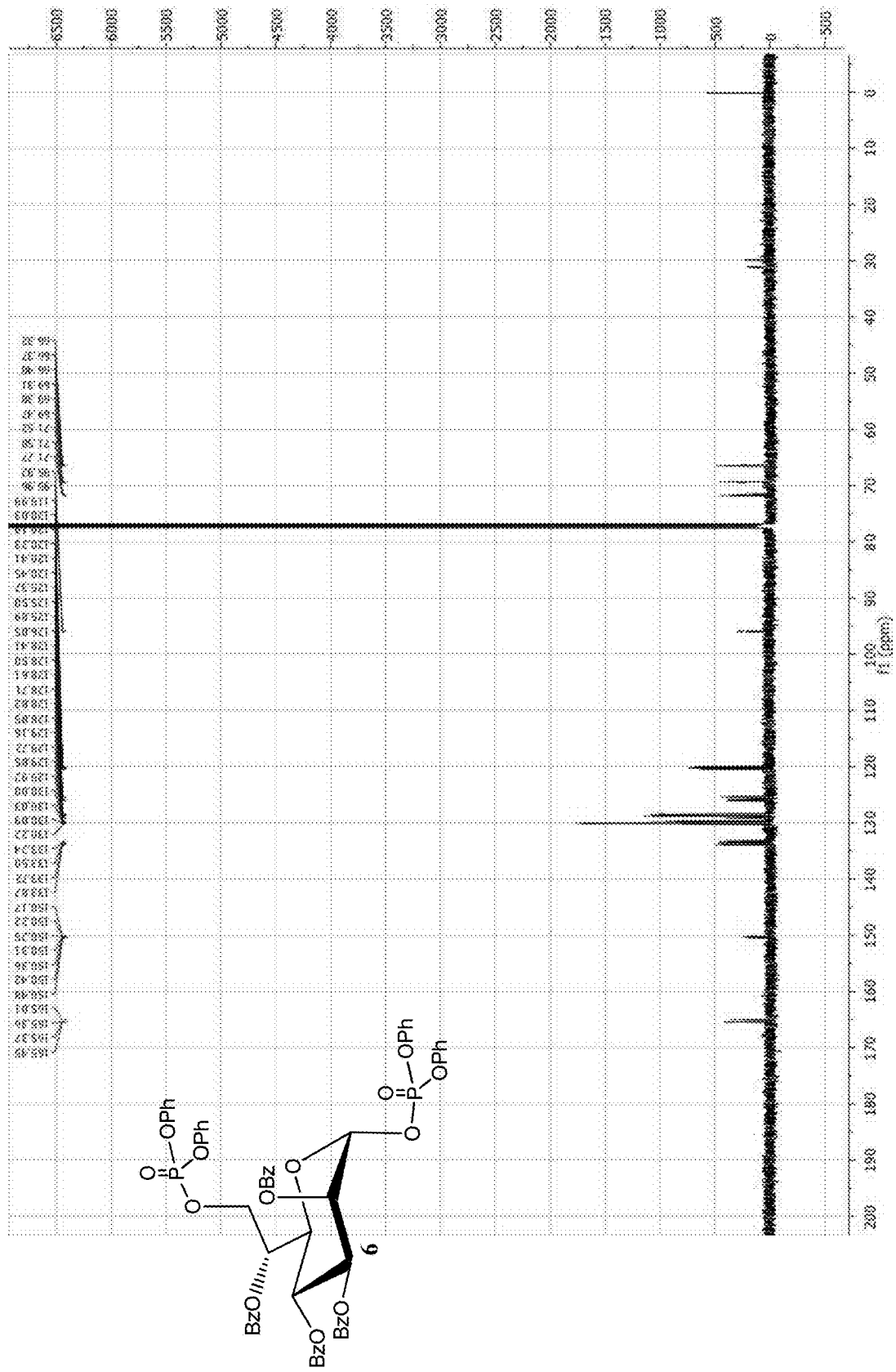
FIG. 14: $^{13}$C NMR of compound 6 (α; Scheme 1) at 25° C.
Figure 15:
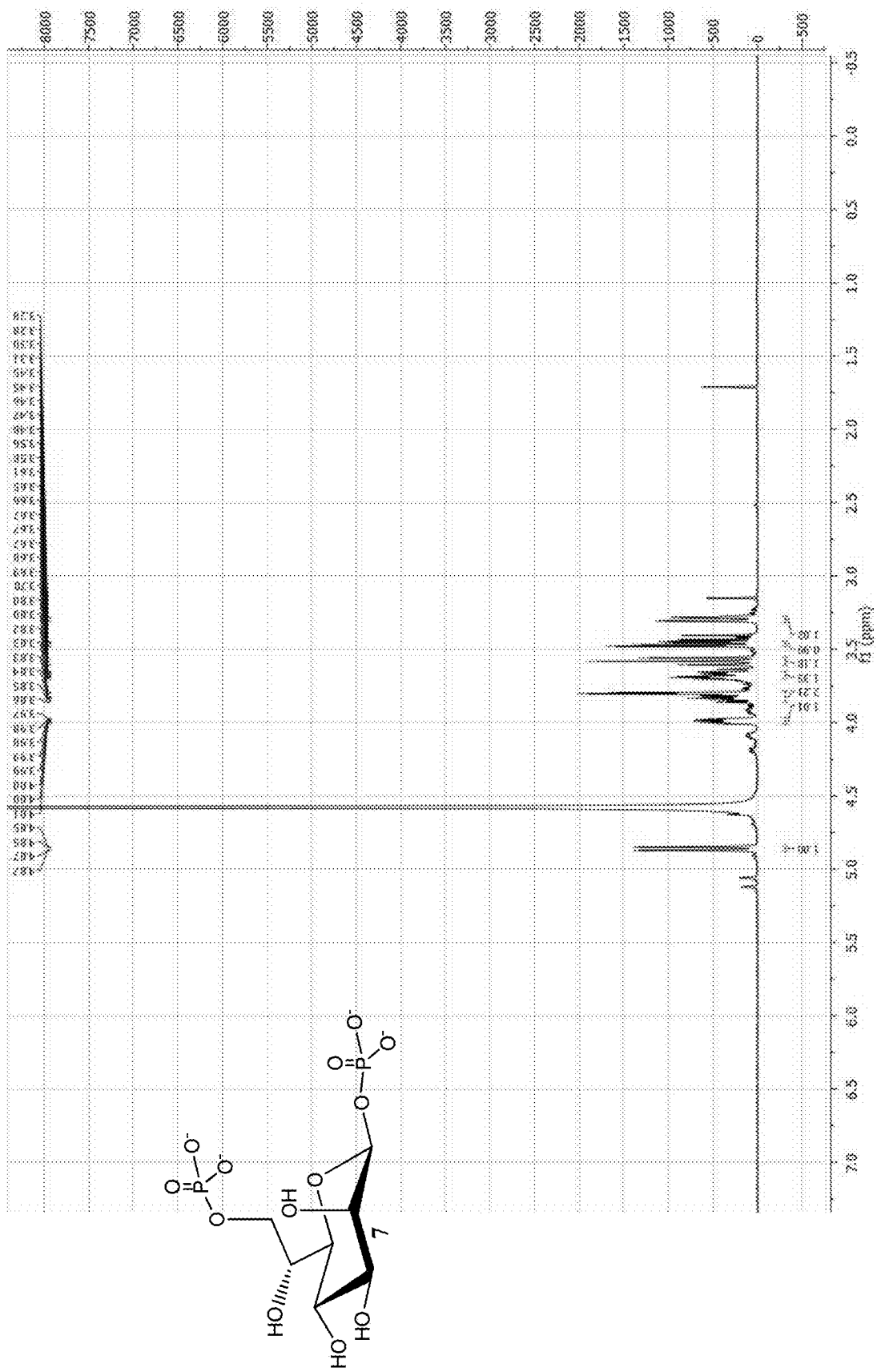
FIG. 15: $^1$H NMR of compound 7 or HBP-β (D-glycero-D-manno-heptopyranose 1β,7-bisphosphate; Scheme 1) at 25° C.
Figure 16:
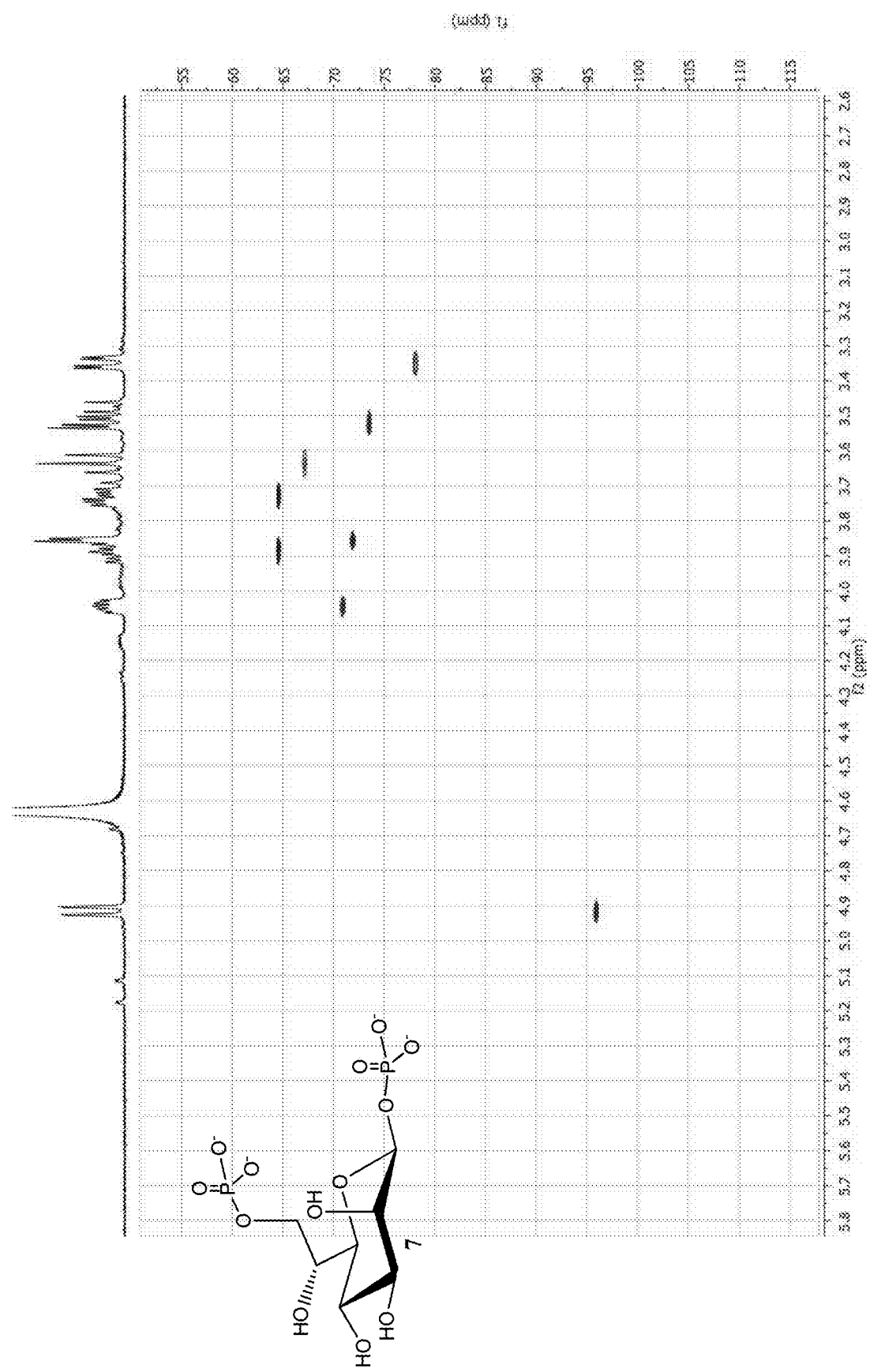
FIG. 16: $^1$H-$^{13}$C NMR of compound 7 or HBP-β (D-glycero-D-manno-heptopyranose 1β,7-bisphosphate; Scheme 1) at 25° C.
Figure 17:
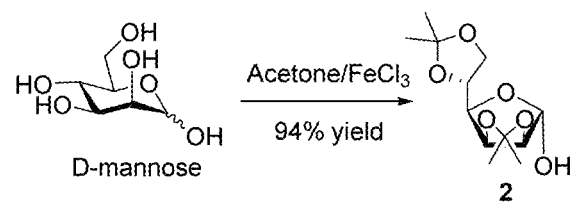
FIG. 17: A) $^1$H NMR of compound 2 (Scheme 2) B) $^{13}$C NMR of compound 2.
Figure 17:
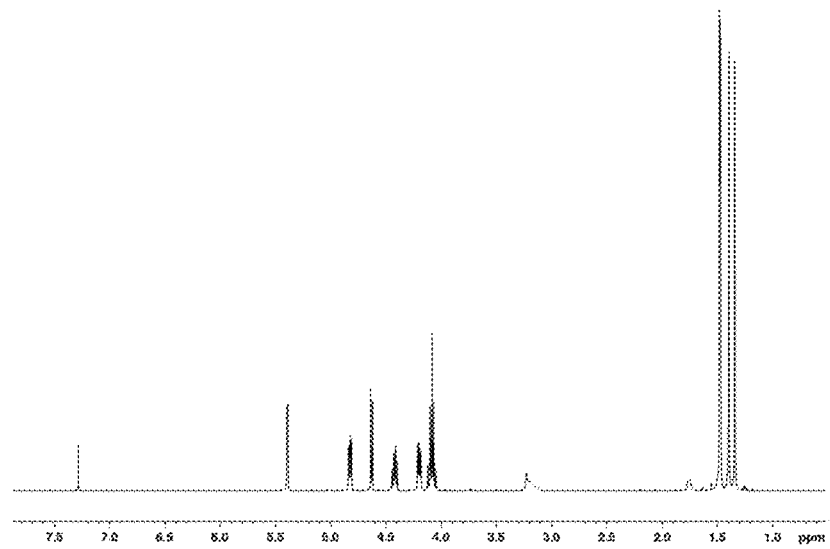
Figure 17:
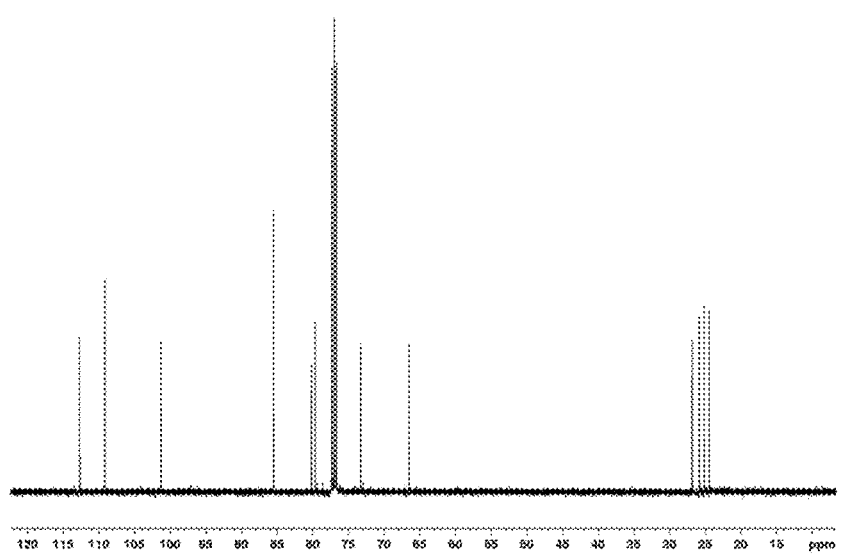
Figure 18:
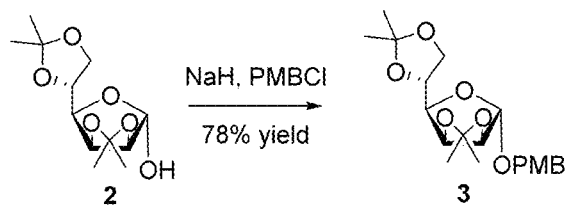
FIG. 18: A) $^1$H NMR of compound 3 (Scheme 2) B) $^{13}$C NMR of compound 3.
Figure 18:
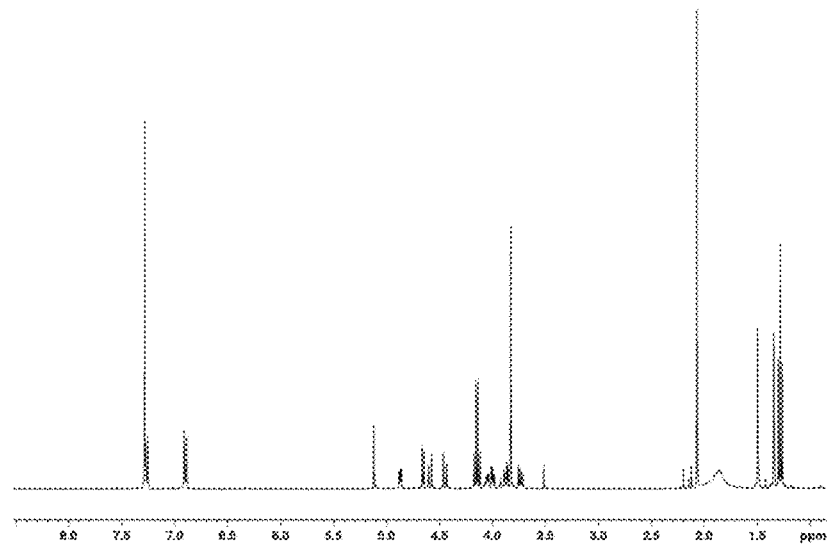
Figure 18:
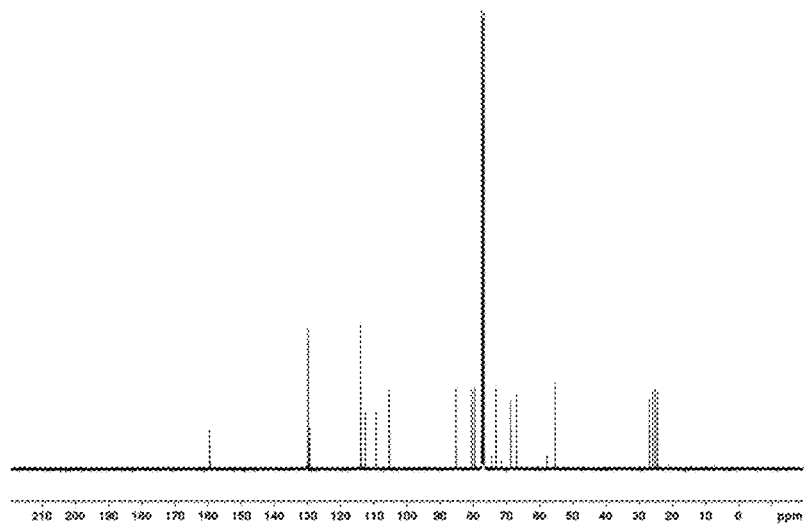
Figure 19:
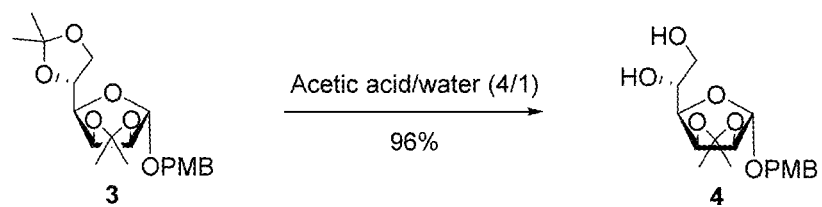
FIG. 19: A) $^1$H NMR of compound 4 (Scheme 2) B) $^{13}$C NMR of compound 4.
Figure 19:
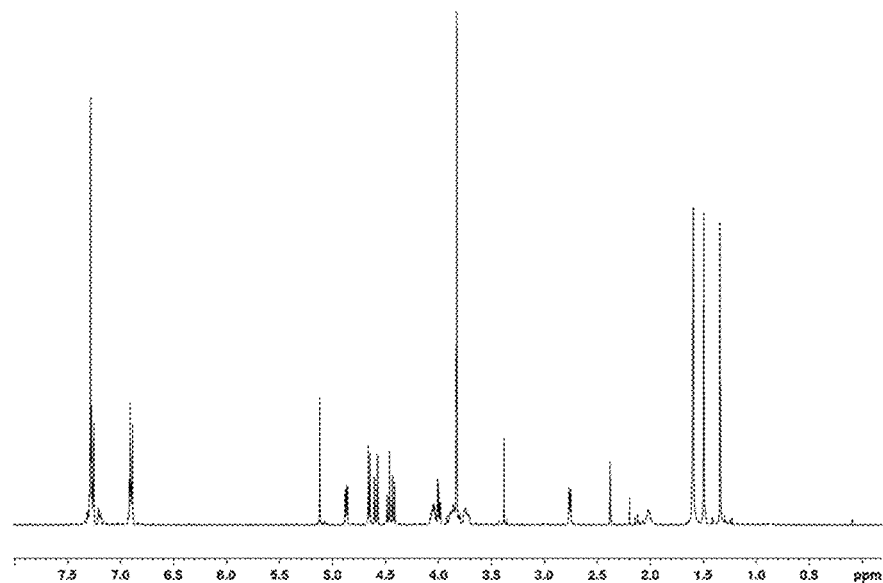
Figure 19:
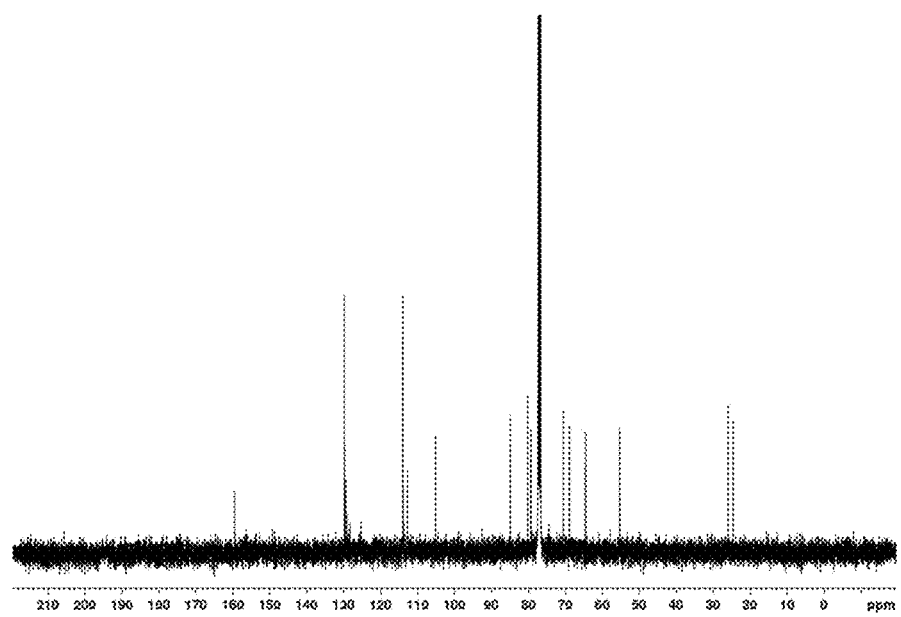
Figure 20:
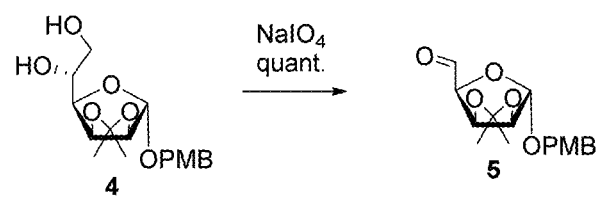
FIG. 20: A) $^1$H NMR of compound 5 (Scheme 2) B) $^{13}$C NMR of compound 5.
Figure 20:
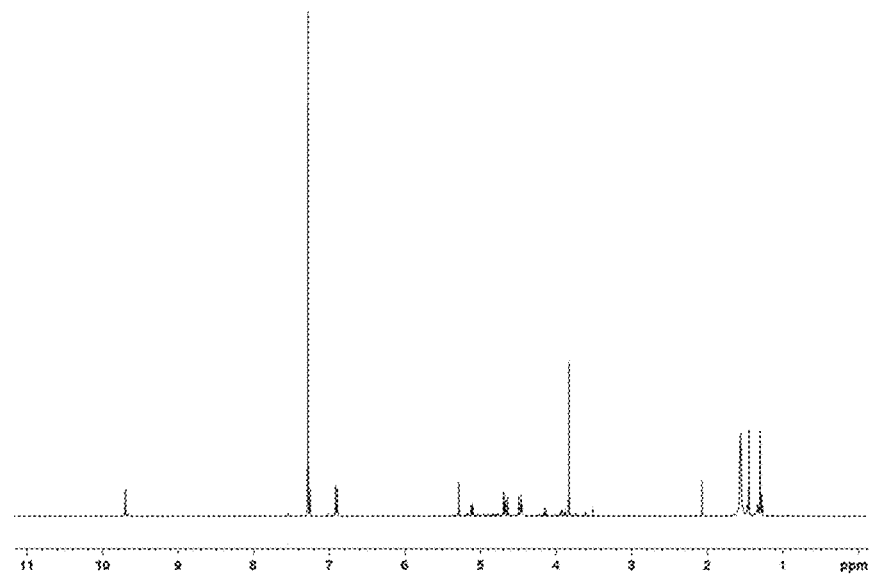
Figure 20:
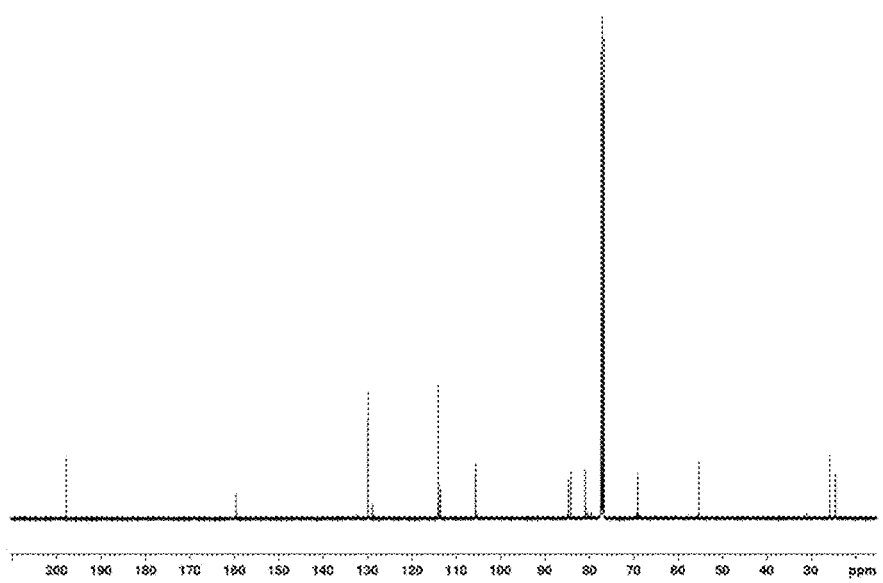
Figure 21:
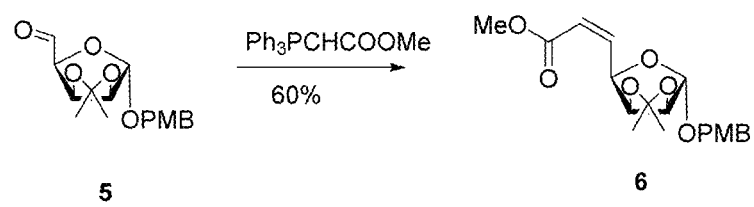
FIG. 21: A) $^1$H NMR of compound 6 (Scheme 2) B) $^{13}$C NMR of compound 6.
Figure 21:
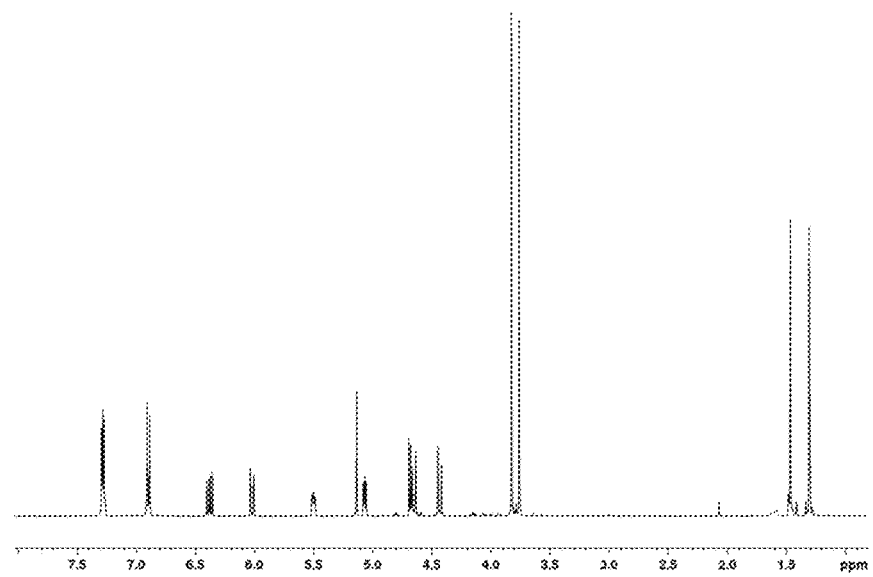
Figure 21:
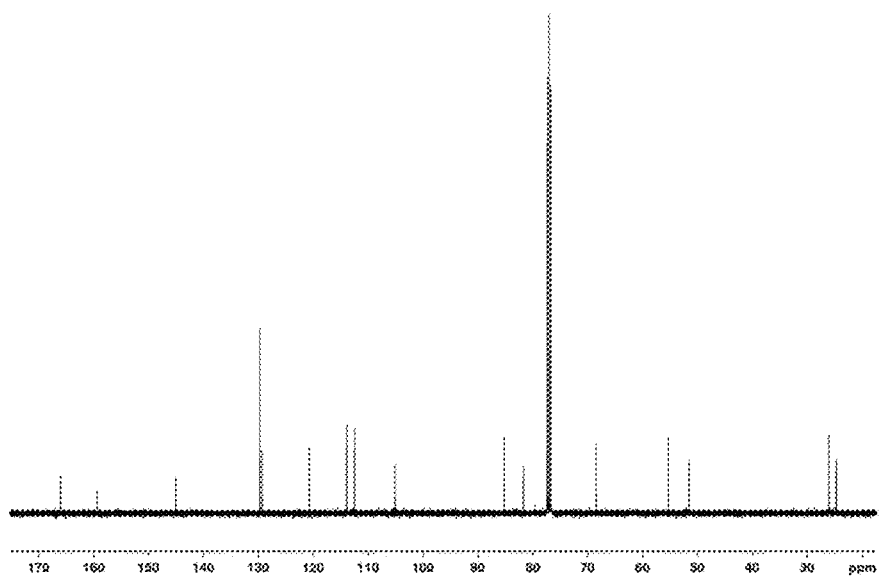
Figure 22:
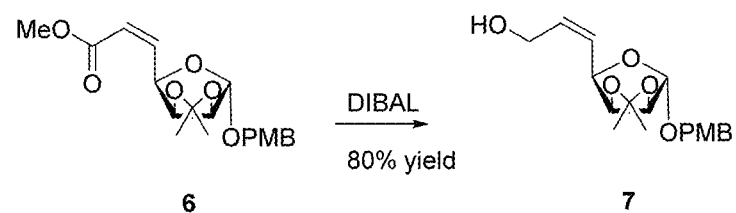
FIG. 22: A) $^1$H NMR of compound 7 or HBP-β (Scheme 2) B) $^{13}$C NMR of compound 7 or HBP-β.
Figure 22:
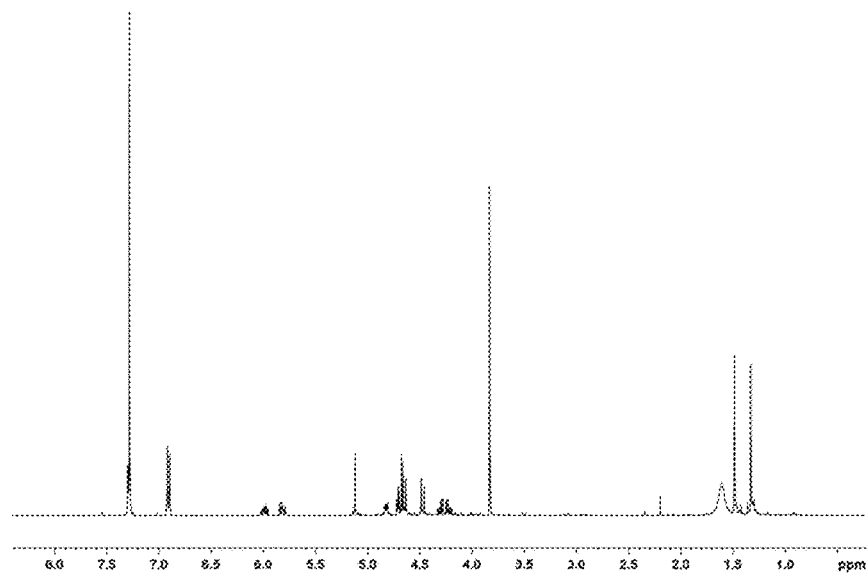
Figure 22:
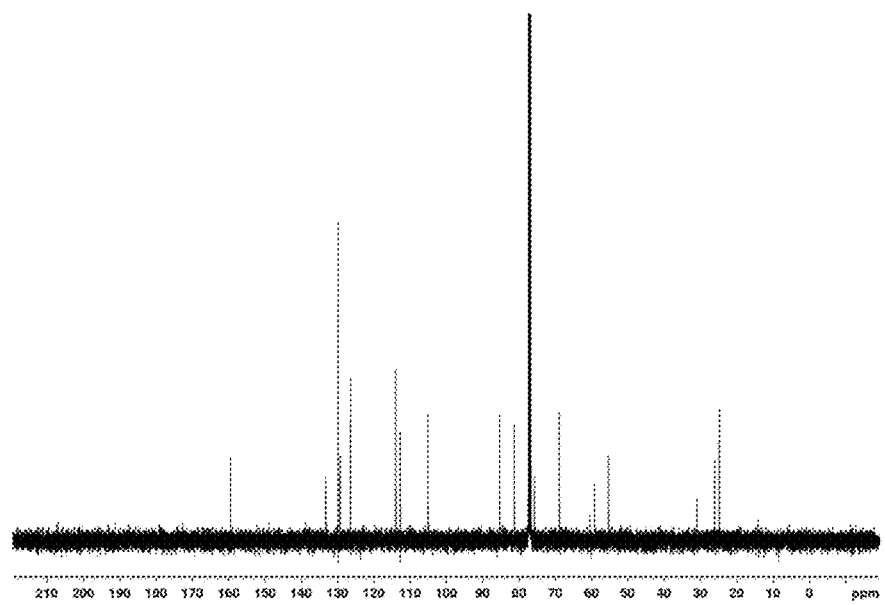
Figure 23:
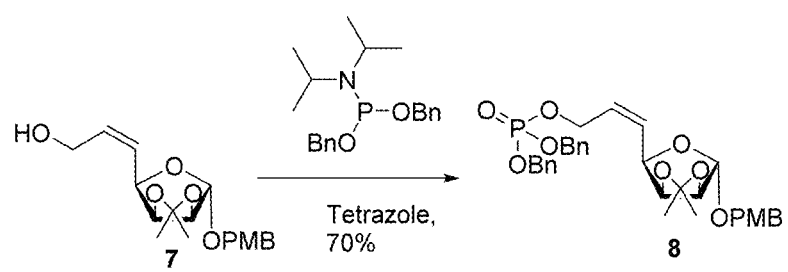
FIG. 23: A) $^1$H NMR of compound 8 (Scheme 2) B) $^{13}$C NMR of compound 8 C) $^{31}$P NMR of compound 8.
Figure 23:
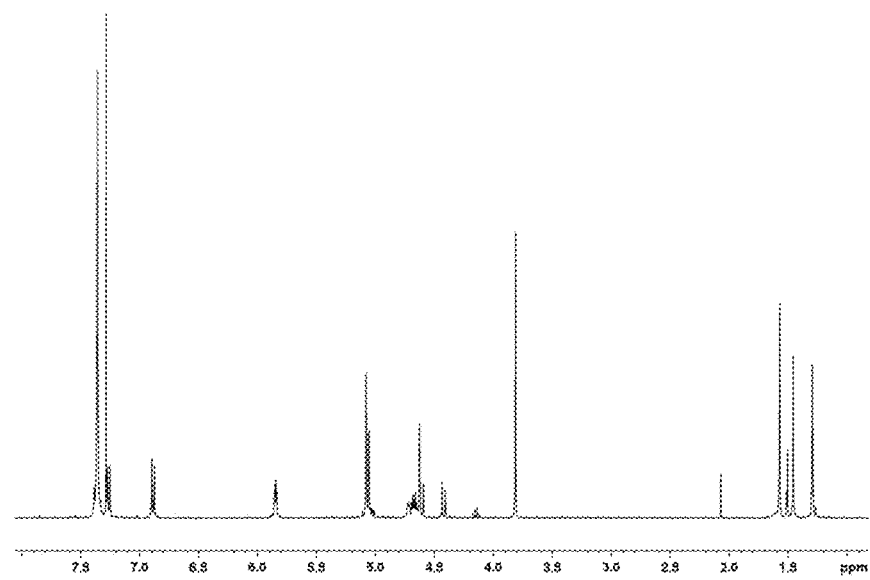
Figure 23:
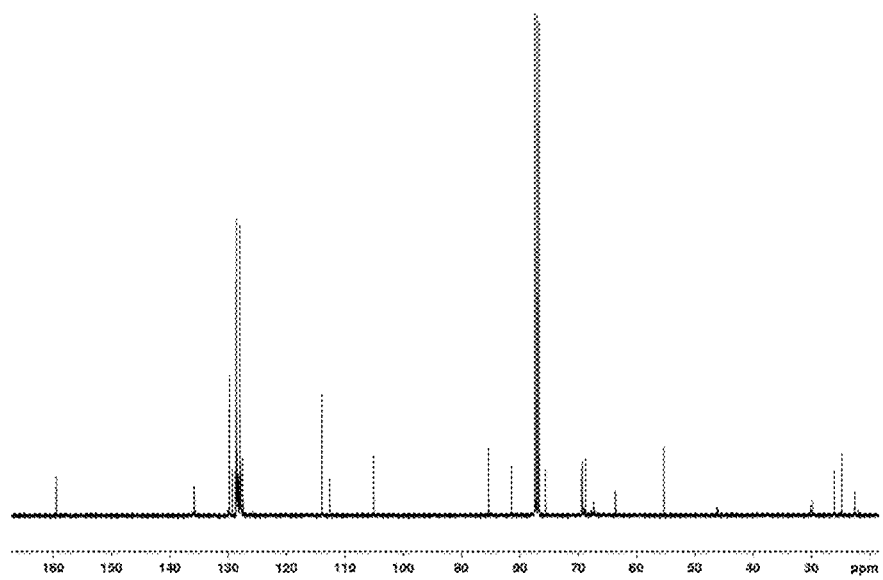
Figure 23:
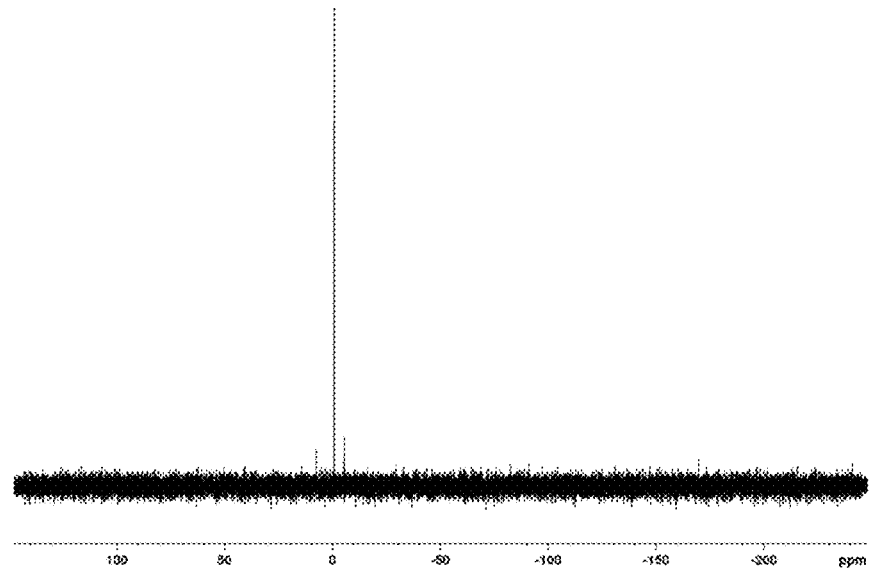
Figure 24:
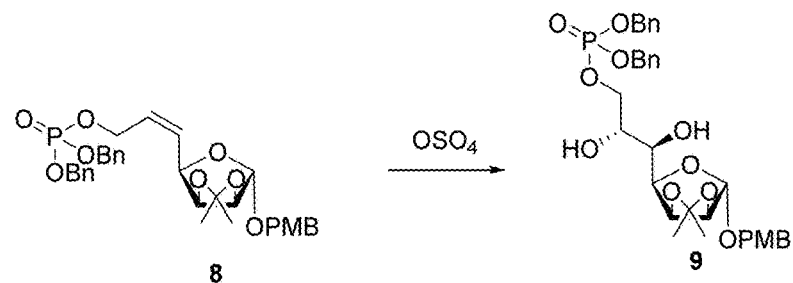
FIG. 24: A) $^1$H NMR of compound 9 (Scheme 2) B) $^{13}$C NMR of compound 9 C) $^{31}$P NMR of compound 9.
Figure 24:
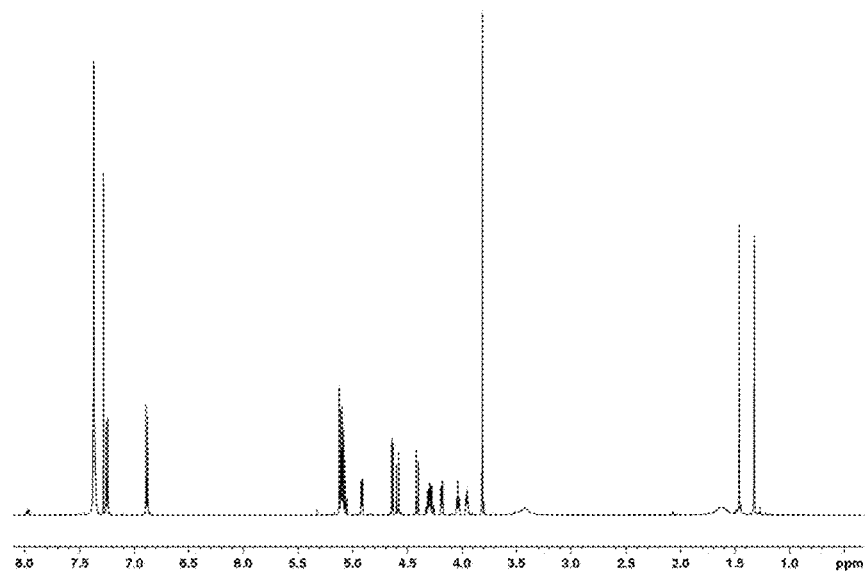
Figure 24:
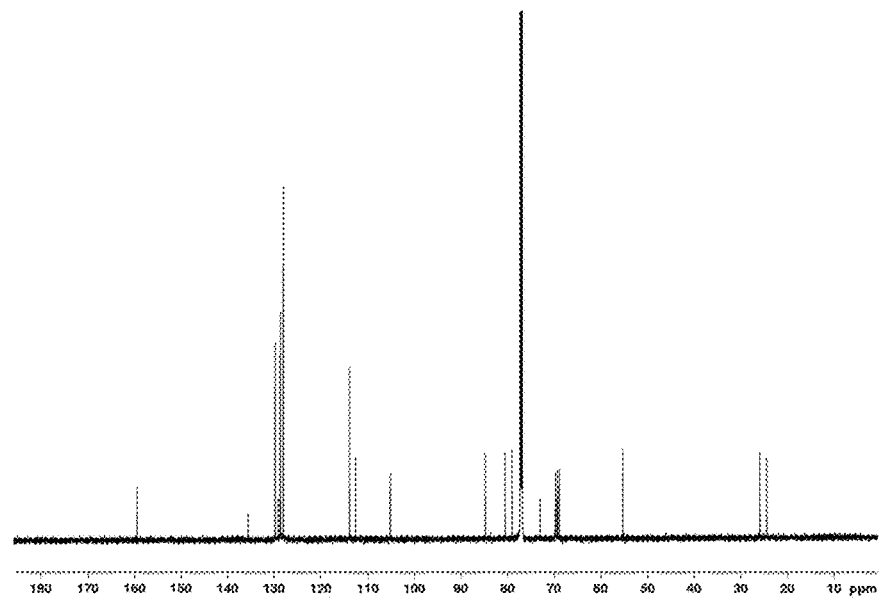
Figure 24:
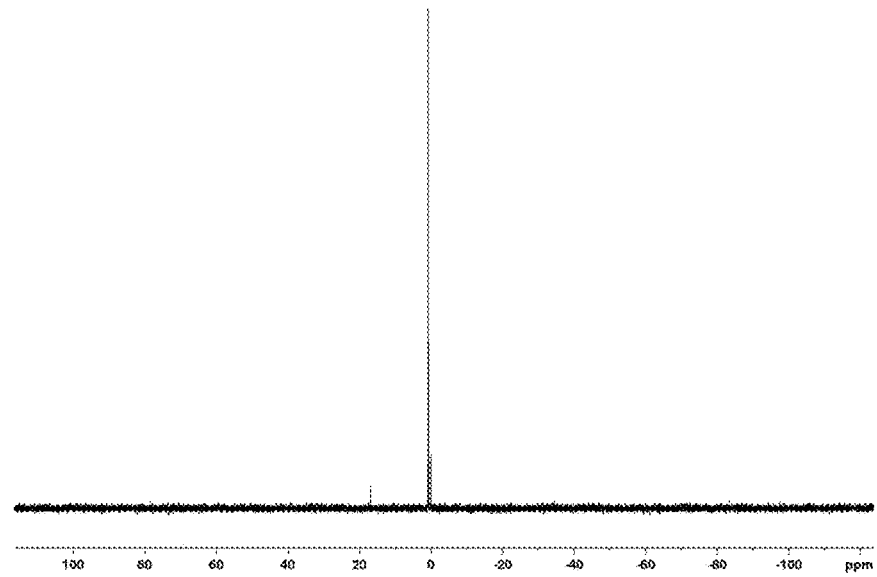
Figure 25:
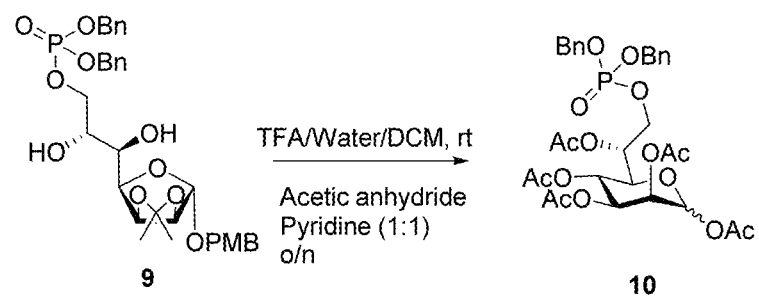
FIG. 25: A) $^1$H NMR of compound 10 (Scheme 2) B) $^{13}$C NMR of compound 10.
Figure 25:
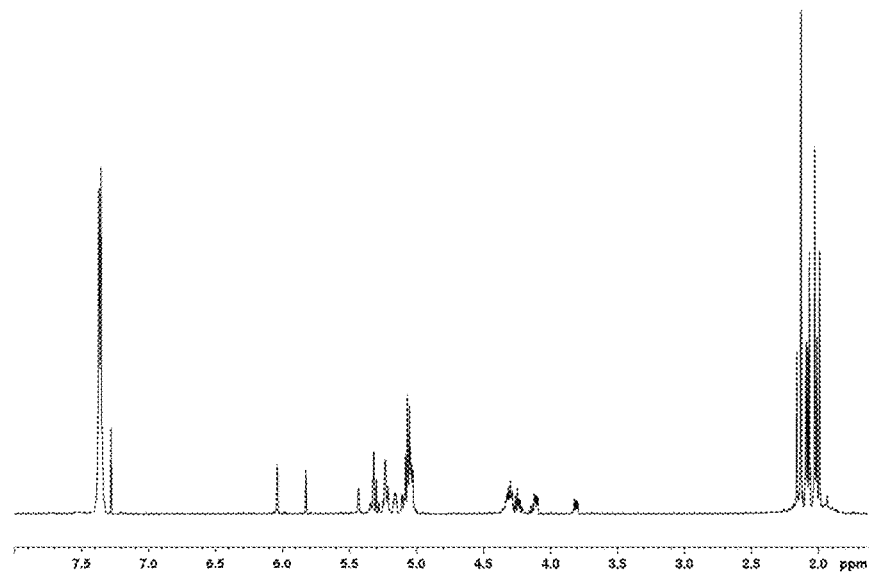
Figure 25:
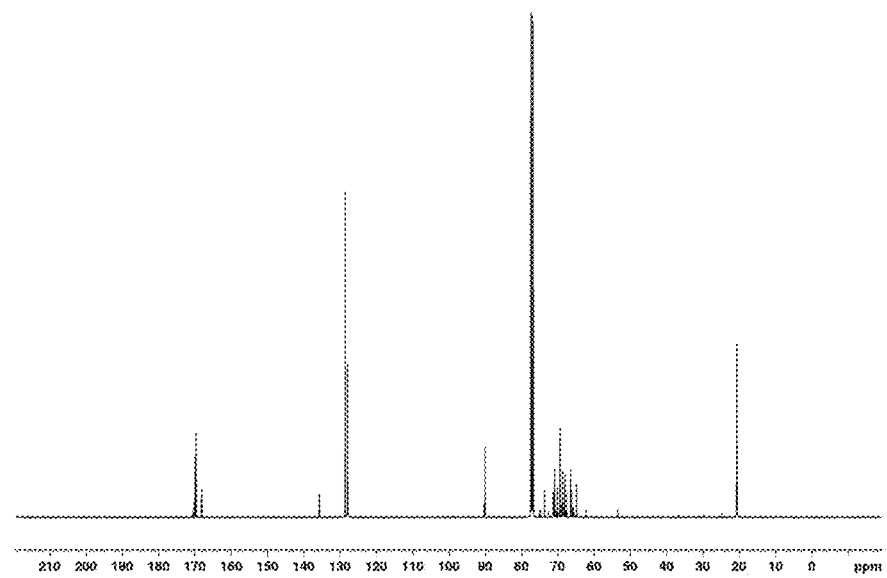
Figure 26:
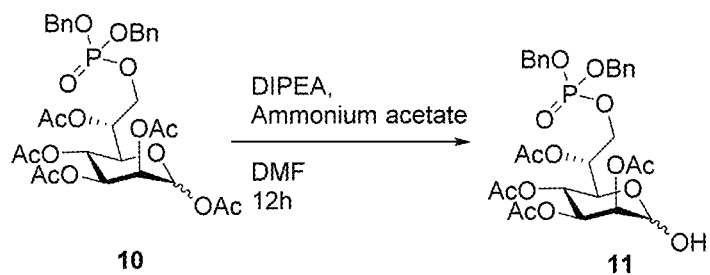
FIG. 26: A) $^1$H NMR of compound 11 (Scheme 2) B) $^{13}$C NMR of compound 11 C) $^{31}$P NMR of compound 11.
Figure 26:
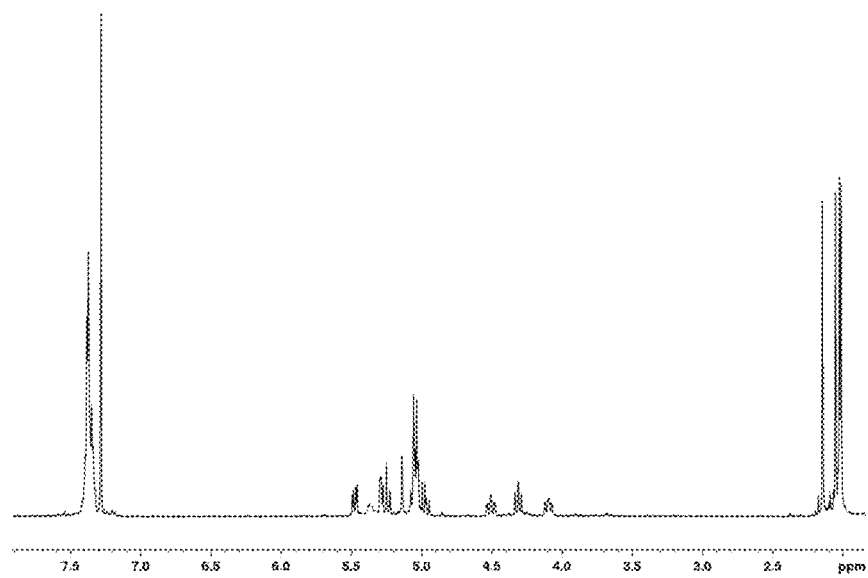
Figure 26:
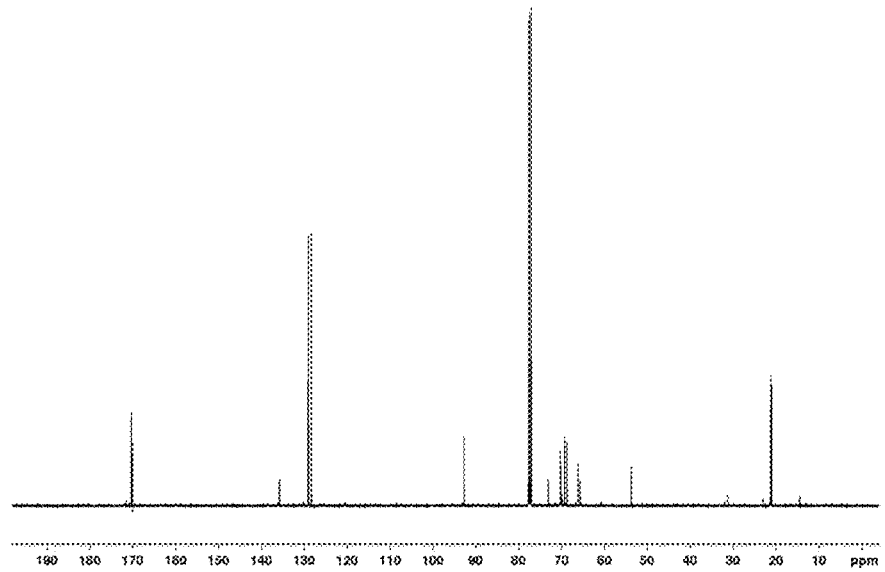
Figure 26:
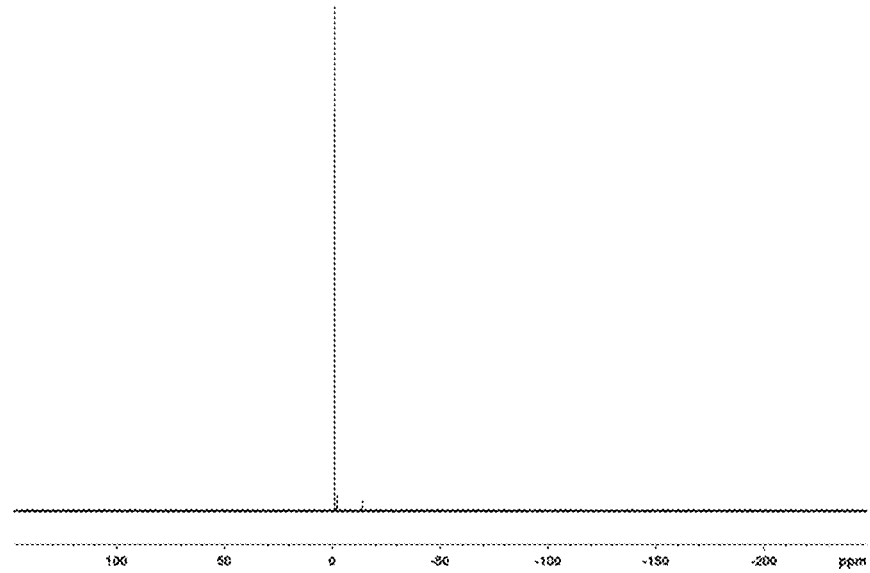
Figure 27:
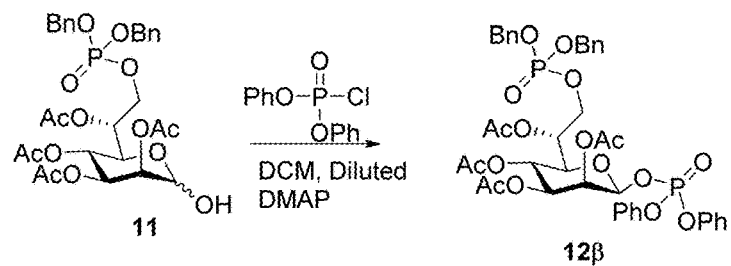
FIG. 27: A) $^1$H NMR of compound 12R (Scheme 2) B) $^{13}$C NMR of compound 12R C) $^{31}$P NMR of compound 12p.
Figure 27:
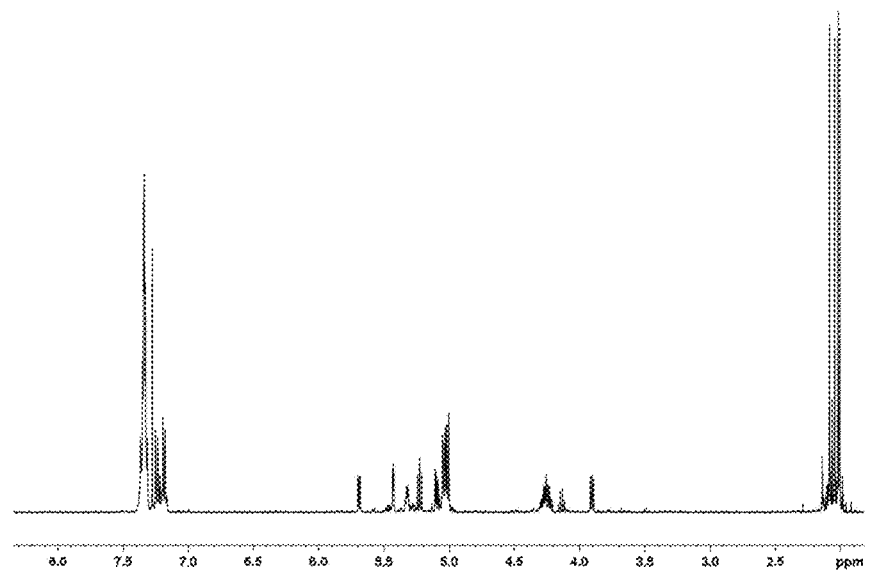
Figure 27:
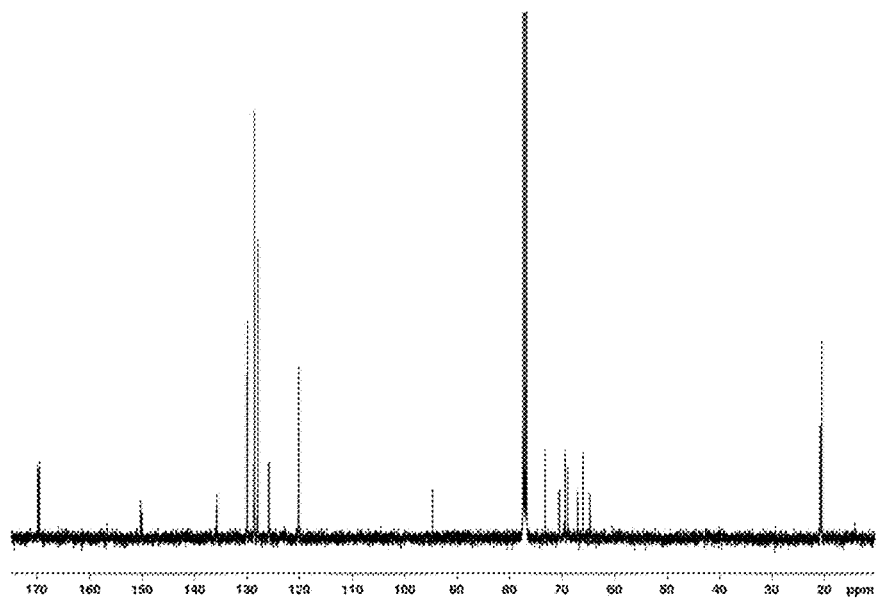
Figure 27:
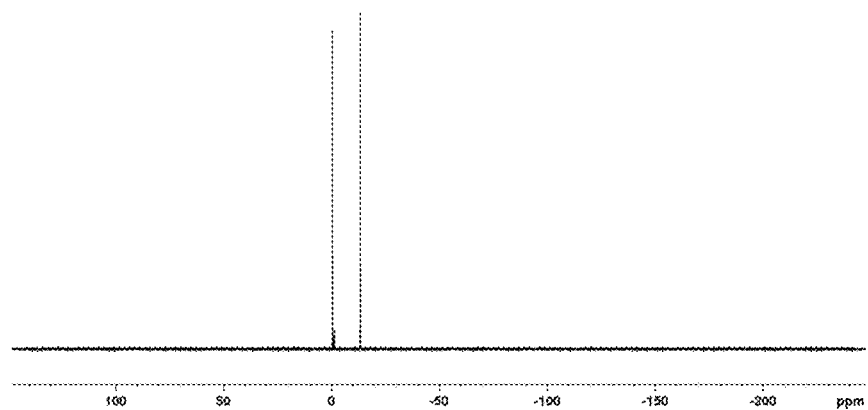
Figure 28:
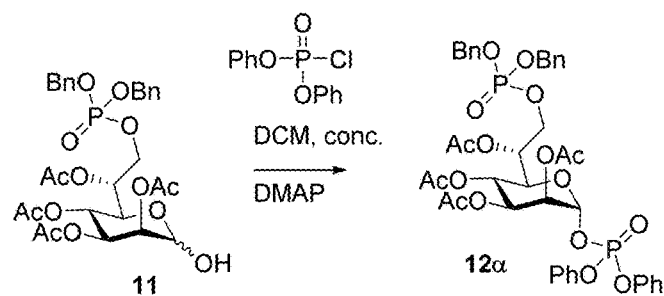
Figure 28:
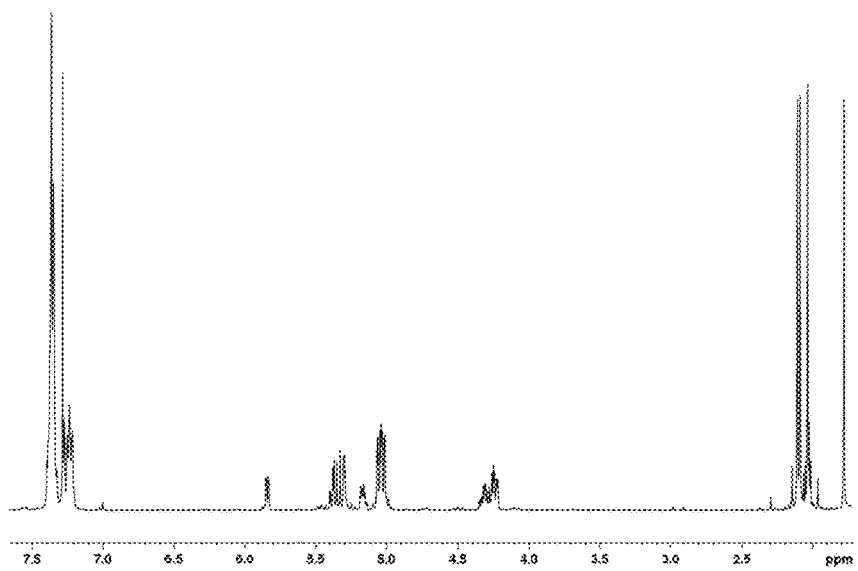
Figure 28:
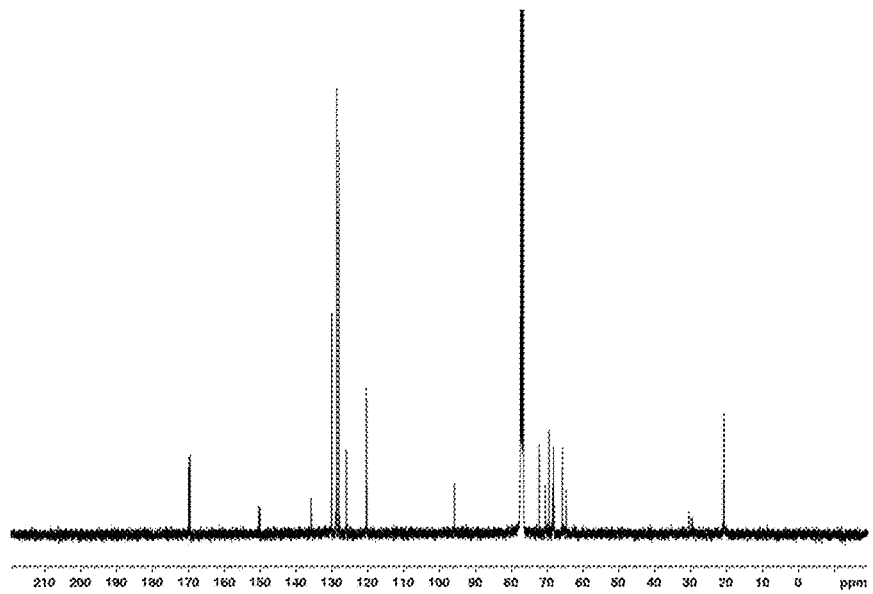
Figure 28:
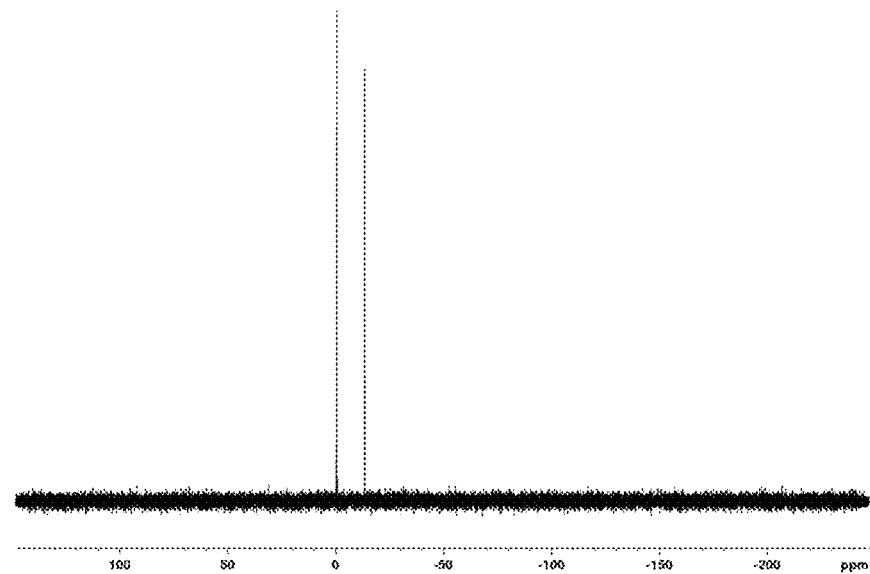
Figure 29:
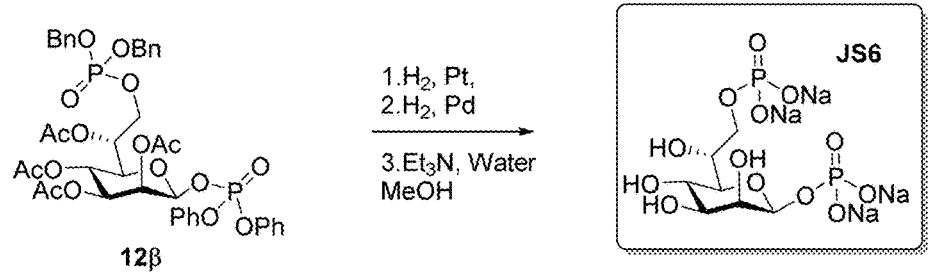
FIG. 29: A) $^1$H NMR of compound JS6 or HBP-β (D-glycero-D-manno-heptopyranose 1β,7-bisphosphate; Scheme 2) B) $^{13}$C NMR of compound JS6 or HBP-β C) $^{31}$P NMR of compound JS6 or HBP-β.
Figure 29:
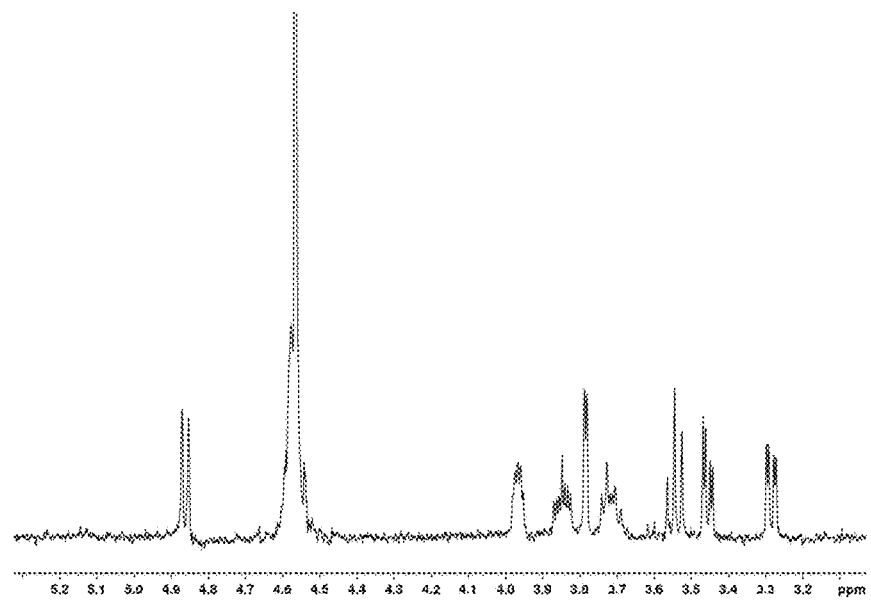
Figure 29:
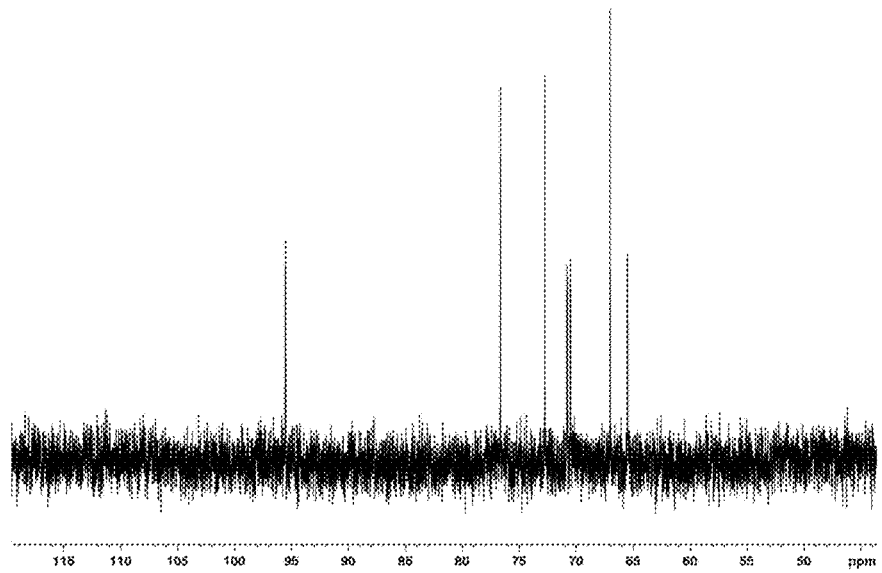
Figure 29:
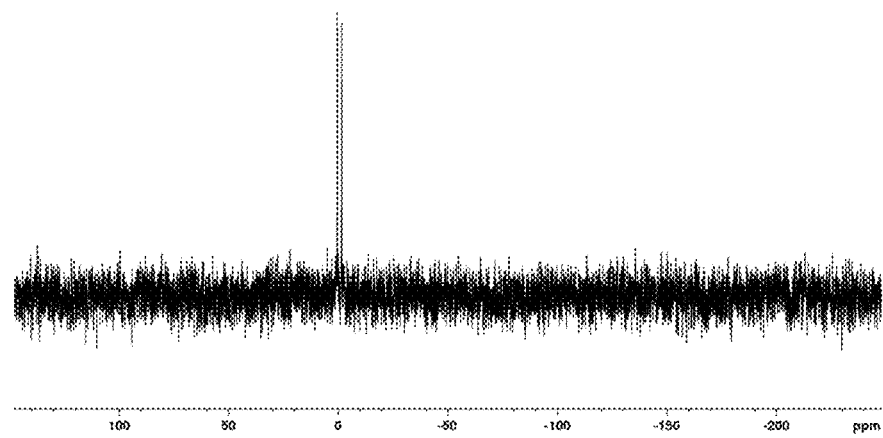
Figure 30:
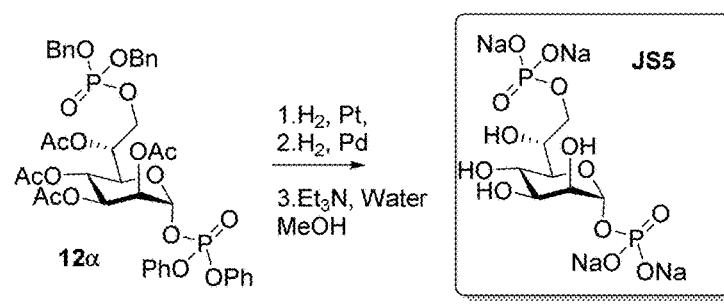
FIG. 30: A) $^1$H NMR of compound JS5 or HBP-α (D-glycero-D-manno-heptopyranose 1α,7-bisphosphate; Scheme 2) B) $^{31}$P NMR of compound JS5 or HBP-α.
Figure 30:
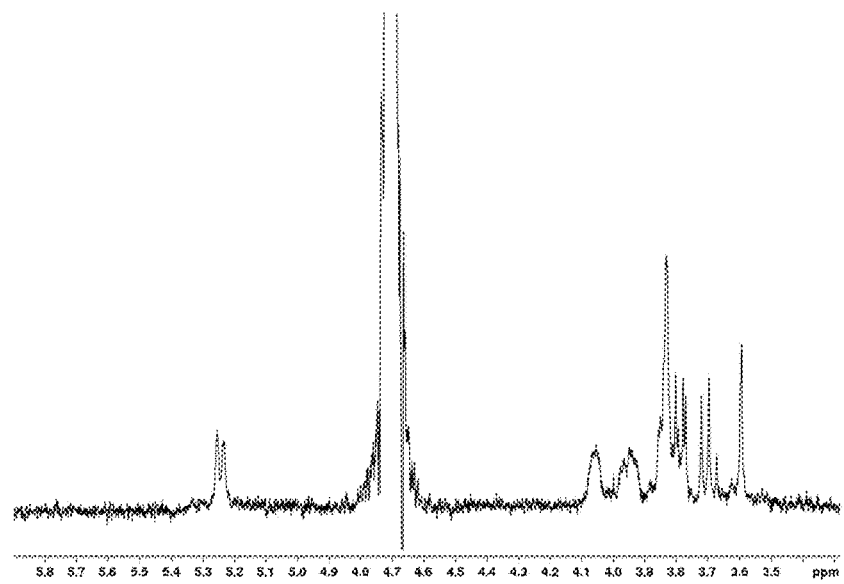
Figure 30:
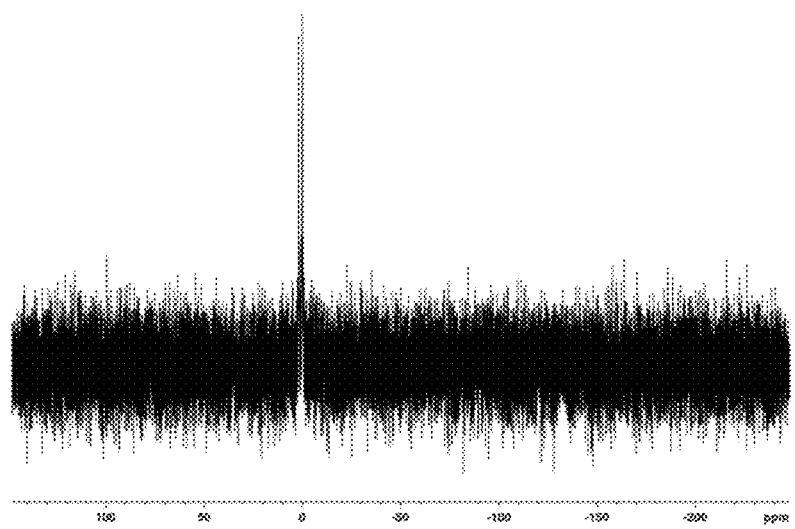

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments, and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

As used herein, the term "phosphorylated heptose compound" refers a monosaccharide with seven carbon atoms, wherein at least one hydroxyl group is replaced by a group comprising a phosphorus atom. For example, the term "bi-phosphorylated heptose compound" refers a monosaccharide with seven carbon atoms, wherein two hydroxyl groups are replaced by a group comprising a phosphorus atom. The term also refers to a derivative or an analogue of such compound.

As used herein, the term "protecting group" refers to a hydroxyl protecting group. The protecting group is introduced in the molecule and modifies the hydroxyl group such that a subsequent chemical reaction is chemoselective.

As used herein, the term "modulate" in connection with an immune or inflammatory response refers to a qualitative or quantitative alteration in the immune or inflammatory response in a subject.

As used herein, the term "vaccine" or "vaccine composition" refers to a pharmaceutical composition containing an immunogen. The composition may be used for modulating an immune response in a subject. The term also refers to subunit vaccines, i.e., vaccine compositions containing immunogens which are separate and discrete from a whole organism with which the immunogen is associated in nature.

As used herein, the term "effective amount" refers to the amount of a compound or reaction product sufficient to cure, alleviate or partially arrest the clinical manifestations of a given disease and its complications in a therapeutic intervention comprising the administration of said compound or reaction product. An effective amount for each purpose will depend on the severity of the disease or injury as well as the weight and general state of the subject.

As used herein, the term "subject" is understood as being any mammal including a human being treated with a compound of the invention.

As used herein the terms "treatment" and "treating" mean the management and care of a subject for the purpose of combating a condition, such as a disease or disorder. The term is intended to include the full spectrum of treatments for a given condition from which the patient is suffering, such administration of the active compounds to alleviate the symptoms or complications, to delay the progression of the condition, and/or to cure or eliminate the condition. The subject to be treated is preferably a mammal, in particular a human being.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The inventors have designed chemical syntheses for the preparation of phosphorylated heptose compounds. Embodiments of the invention relate to the chemical synthesis of heptopyranose phosphate compounds. Also, embodiments of the invention relate to the use of compounds according to the invention in modulating an immune response in a subject.

The present invention is illustrated in further details by the following non-limiting examples.

Example 1—Preparation of D-glycero-D-manno-heptopyranose 1β,7-bisphosphate (7 or HBP-β)

The chemical synthesis of D-glycero-D-manno-heptopyranose 1β,7-bisphosphate (7 or HBP-β) is outlined in Scheme 1 below.

Compound 1 was prepared by a procedure disclosed by Brimacombe et al. [3].

Scheme 1. Chemical synthesis of D-glycero-D-manno-heptopyranose 1β, 7-bisphosphate (7 or HBP-β)

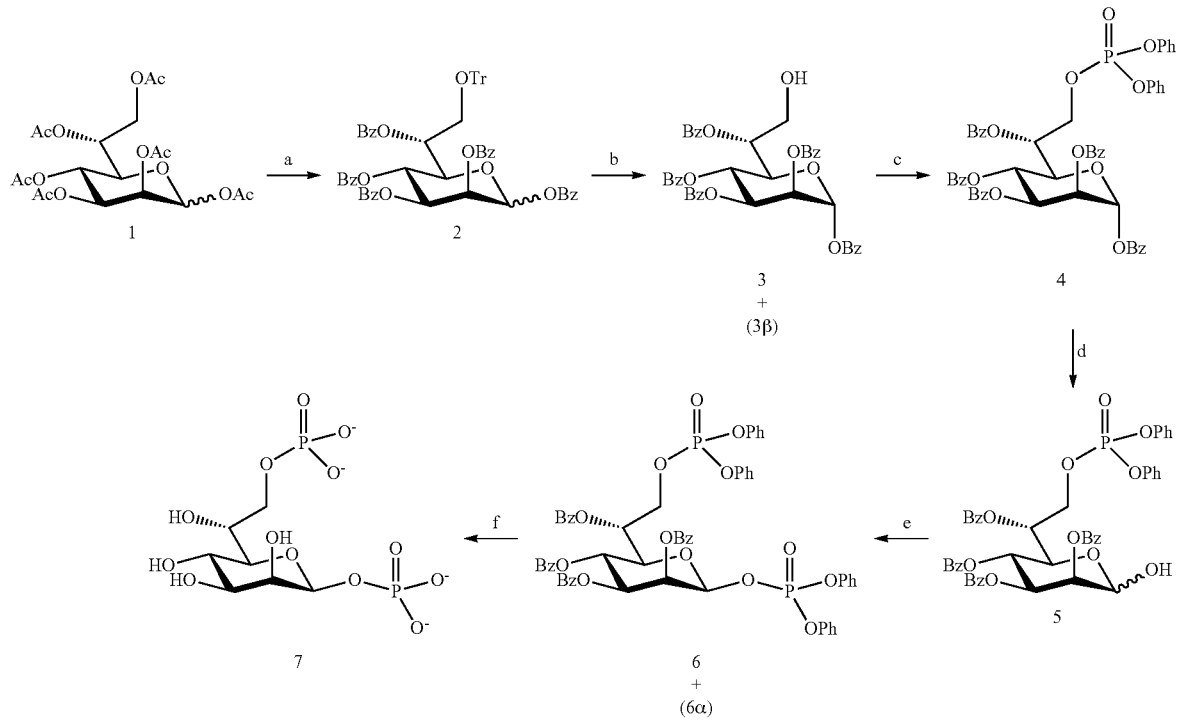

Reagents and conditions: a) 1. MeONa, MeOH, 2. TrCl, py, then BzCl, 57%; b) H₂, Pd/C, TrCl, CH₂Cl₂, 80%; c) P(O)(OPh)₂Cl, DMAP, CH₂Cl₂, 88%;
d) 1. HBr 33% in AcOH, 2. AgOTf, Ag₂CO₃, H₂O, CH₂Cl₂, 50%, e)c) P(O)(OPh)₂Cl, DMAP, CH₂Cl₂, 85%; f) 1. PtO₂, H₂, MeOH, 2. NaOH (1M), H₂O, MeOH.

Example 1a

Preparation of 1,2,3,4,6-penta-O-benzoyl-7-O-(triphenylmethyl)-D-glycero-D-manno-heptopyranose (2). Sodium methoxide (20 mg, 0.73 mmol) was added to a solution of 1 (200 mg, 0.43 mmol) in dry methanol (20 mL). The mixture was stirred at 20° C. for 2 hours. After complete conversion, Dowex® (H⁺) acidic ion exchange resin was added for neutralization. Then the resin was filtered off, washed with methanol, and the filtrate was concentrated in vacuo. The crude was dissolved in dry pyridine (5 mL) and trityl chloride (362 mg, 1.29 mmol) was added to the solution. After 48 hours, benzoyl chloride (0.5 mL, 4.3 mmol) was added. After 24 hours, H₂O (20 mL) and CH₂Cl₂ (20 mL) were added. The layers were separated, and the organic layer was dried over MgSO₄. The solids were filtered off, and the filtrate was concentrated in vacuo. Purification by flash column chromatography (toluene-EtOAc, 99:1→7:3) gave 2 (240 mg, 57%) as a colourless syrup. $R_f$ 0.61 (toluene-EtOAc, 9:1); 100:15 α:β mixture based on the integration of anomeric protons. ¹H NMR (500 MHz, CDCl₃) δ 8.20-8.09 (m, 4H), 7.91-7.86 (m, 2H), 7.83-7.78 (m, 2H), 7.74-7.67 (m, 2H), 7.65-7.61 (m, 1H), 7.59-7.55 (m, 1H), 7.53-7.39 (m, 8H), 7.33-7.02 (m, 20H), 6.51 (d, J 2.0 Hz, 1H, H-1), 6.32 (t, J 10.0 Hz, 1H, H-4), 5.99 (dd, J 3.2 Hz, J 10.1 Hz, 1H, H-3), 5.82 (t, J 2.7 Hz, 1H, H-2), 5.73 (dt, J 3.4 Hz, J 7.4 Hz, 1H, H-6), 4.66 (dd, J 3.4 Hz, J 10.0 Hz, 1H, H-5), 3.50-3.40 (m, 1H, H-7a), 3.24 (dd, J 3.4 Hz, J 10.4 Hz, 1H, H-7b); ¹³C NMR (126 MHz, CDCl₃) δ 165.8, 165.3, 165.2, 165.1, 163.8 (5C, CO, Bz), 143.6, 134.0, 133.6, 133.4, 133.3, 133.1, 130.2, 130.2, 130.0, 129.9, 129.9, 129.8, 128.9, 128.9, 128.9, 128.7, 128.6, 128.6, 128.5, 128.5, 128.4, 128.1, 127.8, 127.4, 127.0 (C₆H₅), 91.2 (C-1, $J_{C-1,H-1}$ 181 Hz), 86.8 (Ph₃C), 73.5 (C-6), 71.5 (C-5), 70.3 (C-3), 69.3 (C-2), 66.7 (C-4), 62.7 (C-7); HRMS (ESI): [M+Na]⁺ m/z Calcd for C₆₁H₄₈O₁₂Na, 995.3043; found, 995.3084.

Example 1b

Preparation of 1,2,3,4,6-penta-O-benzoyl-D-glycero-α-D-manno-heptopyranose (3a) and 1,2,3,4,6-penta-O-benzoyl-D-glycero-β-D-manno-heptopyranose (3b). 10% w Pd/C (20 mg, 18.9 μmol) and trityl chloride (20 mg, 71.7 μmol) were added to a solution of compound 2 (160 mg, 0.16 mmol) in CH₂Cl₂ (5 mL). The mixture was hydrogenolysed in a high-pressure reactor (Berghof) at 20° C. (p=20 bar). After 2.5 hours, the solids were removed by filtration using a 'sandwich filter' (3 frits stacked on top of each other in the following order: 20 μm, 10 μm, 5 μm), rinsed with CH₂Cl₂ (8 mL), and the filtrate was concentrated in vacuo. Purification by flash column chromatography (toluene-EtOAc, 98:2→7:3) gave 3a (86 mg, 72%) and 3b (9 mg, 7%) as colorless syrups.

1,2,3,4,6-Penta-O-benzoyl-D-glycero-α-D-manno-heptopyranose (3a): $R_f$ 0.32 (toluene-EtOAc, 9:1); [α]$_D^{20}$ −81.6 (C 1.0, CHCl₃); ¹H NMR (500 MHz, CDCl₃) δ 8.18-8.05 (m, 4H), 7.99-7.81 (m, 6H), 7.68-7.57 (m, 2H), 7.56-7.39 (m, 7H), 7.33-7.24 (m, 6H), 6.56 (d, J 2.1 Hz, 1H, H-1), 6.27 (t, J 10.0 Hz, 1H, H-4), 6.04 (dd, J 3.3 Hz, J 9.9 Hz, 1H, H-3), 5.90 (t, J 2.6 Hz, 1H, H-2), 5.48 (q, J 4.5 Hz, 1H, H-6), 4.68 (dd, J 3.8 Hz, J 10.1 Hz, 1H, H-5), 4.11-4.00 (m, 2H, H-7a, H-7b); ¹³C NMR (126 MHz, CDCl₃) δ 166.1, 165.7, 165.7, 165.3, 164.2 (5C, CO, Bz), 134.2, 133.9, 133.6, 133.5, 133.3, 130.3, 130.1, 129.9, 129.9, 129.9, 129.4, 129.0, 128.9, 128.8, 128.8, 128.7, 128.6, 128.5, 128.5, 128.4

($C_6H_5$), 91.6 (C-1, $J_{C-1,H-1}$ 181.0 Hz), 74.8 (C-6), 72.0 (C-5), 70.2 (C-3), 69.4 (C-2), 67.4 (C-4), 61.8 (C-7); HRMS (ESI): [M+Na]⁺ m/z Calcd for $C_{42}H_{34}O_{12}Na$, 753.1948; found, 753.1965.

1,2,3,4,6-Penta-O-benzoyl-D-glycero-β-D-manno-heptopyranose (3b): $R_f$ 0.23 (toluene-EtOAc, 9:1); $[α]_D^{20}$ −76.2 (C 1.0, CHCl₃); ¹H NMR (500 MHz, CDCl₃) δ 8.19-8.05 (m, 2H), 7.97-7.90 (m, 4H), 7.86-7.75 (m, 4H), 7.65-7.61 (m, 1H), 7.57-7.52 (m, 1H), 7.50-7.35 (m, 7H), 7.30-7.19 (m, 6H), 6.32 (d, J 1.2 Hz, 1H, H-1), 6.17-6.06 (m, 2H, H-2, H-4), 5.80 (dd, J 3.3 Hz, J 9.6 Hz, 1H, H-3), 5.58-5.50 (m, 1H, H-6), 4.53 (dd, J 5.4 Hz, J 9.5 Hz, 1H, H-5), 4.12 (dd, J 4.7 Hz, J 12.7 Hz, 1H, H-7a), 4.04 (dd, J 3.3 Hz, J 12.7 Hz, 1H, H-7b); ¹³C NMR (126 MHz, CDCl₃) δ 166.0, 165.7, 165.6, 165.6, 164.8 (5C, CO, Bz), 134.1, 133.8, 133.6, 133.5, 133.2, 130.3, 130.1, 130.0, 129.9, 129.9, 129.4, 129.3, 128.8, 128.8, 128.7, 128.5, 128.5, 128.4, 128.3 ($C_6H_5$), 91.9 (C-1, $J_{C-1,H-1}$ 165.0 Hz), 74.7 (C-6), 73.8 (C-5), 71.5 (C-3), 69.2 (C-2), 68.1 (C-4), 62.0 (C-7); HRMS (ESI): [M+Na]m/z Calcd for $C_{42}H_{34}O_{12}Na$, 753.1948; found, 753.1929.

Example 1c

Preparation of 1,2,3,4,6-penta-O-benzoyl-7-O-[bis(phenyloxy)phosphoryl]-D-glycero-α-D-manno-heptopyranose (4). To a stirred solution of 3a (40 mg, 54.8 μmol) and N,N-dimethylaminopyridine (39 mg, 0.32 mmol) in dry CH₂Cl₂ (2 mL), a solution of diphenyl phosphorochloridate (17 μL, 82 μmol), in CH₂Cl₂ (1.4 mL) was added dropwise over 10 minutes at room temperature under N₂. After 30 minutes, the reaction mixture was diluted with CH₂Cl₂ (10 mL), washed with 1 M aq TEAB buffer (2×20 mL) and brine (20 mL). The organic layer was dried over MgSO₄. The solids were filtered off, and the filtrate was concentrated in vacuo. Purification by flash column chromatography (toluene-EtOAc, 98:2→7:3) gave 4 (50 mg, 94%) as a colourless syrup. $R_f$ 0.35 (toluene-EtOAc, 9:1); $[α]_D^{20}$ −40.6 (C 1.0, CHCl₃); ¹H NMR (500 MHz, CDCl₃) δ 8.15-8.08 (m, 2H), 8.09-8.01 (m, 2H), 7.88-7.78 (m, 6H), 7.64-7.54 (m, 2H), 7.50-7.45 (m, 2H), 7.44-7.37 (m, 5H), 7.28-7.17 (m, 8H), 7.12-7.05 (m, 5H), 7.04-6.96 (m, 3H), 6.60 (d, J 2.0 Hz, 1H, H-1), 6.18 (t, J 9.9 Hz, 1H, H-4), 6.04 (dd, J 3.3 Hz, J 9.8 Hz, 1H, H-3), 5.90 (dd, J 2.1 Hz, J 3.3 Hz, 1H, H-2), 5.76-5.71 (m, 1H, H-6), 4.75 (dd, J 4.8 Hz, J 10.0 Hz, 1H, H-5), 4.72-4.68 (m, 2Hm H-7a, H-7b); ¹³C NMR (126 MHz, CDCl₃) δ 165.6, 165.5, 165.3, 165.2, 163.8 (5C, CO, Bz), 150.4, 150.3 (2 d, $J_{C,p}$ 7.2 Hz, 2 Ph), 134.1, 133.8, 133.5, 133.5, 133.2, 130.2, 130.0, 129.9, 129.8, 129.8, 129.7, 129.6, 128.9, 128.9, 128.8, 128.8, 128.8, 128.6, 128.6, 128.5, 128.4, 128.2, 125.4, 125.4, 125.3, 125.3, 120.1, 120.0, 120.0, 119.9 ($C_6H_5$), 91.2 (C-1, $J_{C-1,H-1}$ 181.5 Hz), 72.0 (d, $J_{6,p}$ 8.1 Hz, C-6), 70.7 (C-5), 70.0 (C-3), 69.4 (C-2), 67.5 (C-4), 66.4 (d, $J_{7,p}$ 5.8 Hz, C-7); HRMS (ESI): [M+Na]⁺ m/z Calcd for $C_{54}H_{43}O_{15}NaP$, 985.2237; found, 985.2225.

Example 1 d

Preparation of 2,3,4,6-tetra-O-benzoyl-7-O-[bis(phenyloxy)phosphoryl]-D-glycero-D-manno-heptopyranose (5). HBr (0.5 mL, 33% in AcOH) was added dropwise to a solution of 4 (40 mg, 41.6 μmol) and glacial acetic acid (0.1 mL) in dry CH₂Cl₂ (0.1 mL). The reaction vessel was protected from light. The mixture was stirred at room temperature overnight (TLC, toluene-EtOAc, 8:2) and then was poured into ice-water (5 mL) under vigorous stirring. The resulting mixture was extracted with CH₂Cl₂ (5 mL). The layers were separated, and the organic layer was washed sequentially with sat. NaHCO₃-solution (10 mL), and water (10 mL), dried over MgSO₄, and concentrated in vacuo. The obtained crude was dissolved in CH₂Cl₂ (2 mL). To the solution H₂O (3 mL), silver triflate (21.4 mg, 83.2 μmol) and silver carbonate (22.9 mg, 83.2 μmol) were added and the mixture was sonicated until consumption of the bromide (2 hours). The reaction mixture was diluted with CH₂Cl₂ (10 mL), and H₂O (10 mL). The organic layer was separated and was dried over MgSO₄. The solids were filtered off, and the filtrate was concentrated in vacuo. Purification by flash column chromatography (toluene-EtOAc, 97:3→7:3) gave 5 (18 mg, 50%) as a colourless syrup. $R_f$ 0.32 (toluene-EtOAc, 8:2); α:β 100:7 based on anomeric signals. ¹H and ¹³C NMR signals for the alpha anomer: ¹H NMR (500 MHz, CDCl₃) 8.10-8.01 (m, 2H), 7.79-7.67 (m, 4H), 7.62-7.54 (m, 2H), 7.62-7.55 (m, 2H), 7.41-7.01 (m, 20H), 6.02 (dd, J 2.9 Hz, J 10.2 Hz, 1H, H-3), 5.90 (t, J 9.8 Hz, 1H, H-4), 5.70-5.67 (m, 1H, H-2), 5.59 (bd, J 8.2 Hz, 1H, H-6), 5.39 (bs, 1H, H-1), 5.26 (bs, 1H, OH), 4.94 (t, J 10.4 Hz, 1H, H-7a), 4.74 (t, J 9.0 Hz, 1H, H-5), 4.48 (t, J 10.1 Hz, 1H, H-7b); ¹³C NMR (126 MHz, CDCl₃) δ 165.8, 165.6, 165.5, 165.3 (4C, CO, Bz), 150.4, 150.4 (2d, $J_{C,p}$ 7.4 Hz, $J_{C,p}$ 7.5 Hz, 2 C, Ph), 133.6, 133.2, 133.1, 133.0, 130.1, 130.0, 130.0, 129.8, 129.7, 129.6, 129.5, 129.2, 129.0, 128.8, 128.7, 128.3, 128.1, 128.0, 125.9, 125.9, 125.8, 120.4, 120.4, 120.0, 120.0 ($C_6H_5$), 92.9 (C-1, $J_{C-1,H-1}$ 176.5 Hz), 73.4 (d, $J_{6,p}$ 5.3 Hz, C-6), 71.0 (C-2), 69.7 (C-3), 69.7 (C-4), 66.8 (d, $J_{7,p}$ 6.2 Hz, C-7), 65.6 (C-5); HRMS (ESI): [M+Na]⁺ m/z Calcd for $C_{47}H_{39}O_{14}NaP$, 881.1975; found, 881.2003.

Example 1e

Preparation of diphenyl {2,3,4,6-tetra-O-benzoyl-7-O-[bis(phenyloxy)phosphoryl]-D-glycero-α-D-manno-heptopyranosyl} phosphate (6b) and diphenyl {2,3,4,6-tetra-O-benzoyl-7-O-[bis(phenyloxy)phosphoryl]-D-glycero-β-D-manno-heptopyranosyl} phosphate (6a). To a stirred solution of 5 (18 mg, 21 μmol) and N,N-dimethylaminopyridine (26 mg, 0.21 mmol) in dry CH₂Cl₂ (0.6 mL), a solution of diphenyl phosphorochloridate (33 μL, 159 μmol), in CH₂Cl₂ (0.8 mL) was added dropwise with the aid of a syringe pump (injection rate 0.2 mL/h with a 1 mL syringe) at room temperature under N₂. After 4 hours, the reaction mixture was diluted with CH₂Cl₂ (5 mL), washed with 1 M aq TEAB buffer (2×5 mL) and H₂O (10 mL). The organic layer was dried over MgSO₄. The solids were filtered off, and the filtrate was concentrated in vacuo. Purification by flash column chromatography (toluene-EtOAc, 97:3→7:3) gave 6b (1.7 mg, 8%) and 6a (18 mg, 87%) as colourless syrup.

Diphenyl {2,3,4,6-tetra-O-benzoyl-7-O-[bis(phenyloxy)phosphoryl]-D-glycero-β-D-manno-heptopyranosyl} phosphate (6a): $R_f$ 0.67 (cyclohexane-EtOAc, 65:35); $[α]_D^{20}$ −43.1 (C 1.0, CHCl₃); ³¹P NMR (162 MHz, CDCl₃) δ −12.3, −14.0; ¹H NMR (500 MHz, CDCl₃) δ 7.98-7.93 (m, 2H), 7.91-7.87 (m, 2H), 7.87-7.82 (m, 4H), 7.57 (tt, J 1.3 Hz, J 7.4 Hz, 1H), 7.87-7.82 (m, 3H), 7.38-7.34 (m, 2H), 7.33-7.02 (m, 26H), 6.00-5.92 (m, 3H, H-1, H-2, H-4), 5.76 (td, J 3.5 Hz, J 5.4 Hz, 1H, H-6), 5.62 (dd, J 3.2 Hz, J 8.9 Hz, 1H, H-3), 4.65 (ddd, J 3.4 Hz, J 6.7 Hz, J 11.3 Hz, 1H, H-7a), 4.59 (ddd, J 5.7 Hz, J 7.5 Hz, J 11.3 Hz, 1H, H-7b), 4.36 (dd, J 5.4 Hz, J 8.5 Hz, 1H, H-5); ¹³C NMR (126 MHz, CDCl₃) δ165.4, 165.3, 165.3, 165.3 (4C, CO, Bz), 150.5, 150.4, 150.3, 150.0 (4d, $J_{C,p}$ 7.3 Hz, $J_{C,p}$ 7.3 Hz, $J_{C,p}$ 7.4 Hz, $J_{C,p}$ 7.8 Hz, 4 C, Ph), 133.7, 133.6, 133.6, 133.4, 130.1, 130.1, 130.0, 130.0, 129.9, 129.9, 129.8, 129.3, 129.0, 128.7, 128.7, 128.6, 128.6, 128.5, 128.4, 125.8, 125.8, 125.5, 125.4, 120.3, 120.3, 120.3, 120.2, 120.2, 120.1, 120.1 ($C_6H_5$), 95.3 (C-1, $J_{C-1,H-1}$ 167 Hz, $J_{1,p}$ 8.0 Hz), 73.0 (C-5), 71.5 (d, $J_{6,p}$ 8.0 Hz, C-6), 70.5 (C-3), 68.5 (d, $J_{2,p}$ 8.6 Hz, C-2), 66.9 (C-4), 66.0 (d, $J_{7,p}$ 6.0 Hz, C-7); HRMS (ESI): [M+Na]⁺ m/z Calcd for $C_{59}H_{48}O_{17}NaP_2$, 1113.2264; found, 1113.2308.

Diphenyl {2,3,4,6-tetra-O-benzoyl-7-O-[bis(phenyloxy) phosphoryl]-D-glycero-α-D-manno-heptopyranosyl} phosphate (6b): $R_f$ 0.74 (cyclohexane-EtOAc, 65:35); $[\alpha]_D^{20}$ −26.4 (C 0.5, CHCl$_3$); $^{31}$P NMR (162 MHz, CDCl$_3$) δ −12.3, −14.1; $^1$H NMR (500 MHz, CDCl$_3$) δ 7.97-7.86 (m, 6H), 7.85-7.76 (m, 2H), 7.55 (tt, J 1.3 Hz, J 7.5 HZ, 1H), 7.52-7.41 (m, 3H), 7.38-6.92 (m, 28H), 6.16-6.09 (m, 2H, H-1, H-4), 5.88 (dd, J 3.2 Hz, J 9.9 Hz, 1H, H-3), 5.74 (dd, J 2.1 Hz, J 3.2 Hz, 1H, H-2), 5.65 (ddd, J 3.1 Hz, J 4.0 Hz, J 7.2 Hz, 1H, H-6), 4.64 (dd, J 3.0 Hz, J 10.3 Hz, 1H, H-5), 4.62-4.54 (m, 2H, H-7a, H-7b); $^{13}$C NMR (126 MHz, CDCl$_3$) δ 165.4, 165.4, 165.4, 165.0 (4C, CO, Bz), 150.5, 150.3, 150.2 150.2 (4d, $J_{C,p}$ 7.3 Hz, $J_{C,p}$ 7.3 Hz, $J_{C,p}$ 7.4 Hz, $J_{C,p}$ 7.2 Hz, 4 C, Ph), 133.9, 133.7, 133.5, 133.2, 130.2, 130.1, 130.0, 130.0, 129.9, 129.8, 129.7, 129.2, 128.8, 128.8, 128.7, 128.6, 128.5, 128.4, 126.0, 125.9, 125.5, 125.4, 120.4, 120.4, 120.2, 120.2, 120.0, 120.0 (C$_6$H$_5$), 95.9 (C-1, $J_{C-1,H-1}$ 183.5 Hz, $J_{1,p}$ 5.6 Hz), 71.8 (C-5), 71.5 (d, $J_{2,p}$ 8.6 Hz, C-6), 69.4 (d, $J_{6,p}$ 11.1 Hz, C-2), 69.3 (C-3), 66.5 (C-4), 66.3 (d, $J_{7,p}$ 6.0 Hz, C-7); HRMS (ESI): [M+Na]$^+$ m/z Calcd for C$_{59}$H$_{48}$O$_{17}$NaP$_2$, 1113.2264; found, 1113.2224.

Example 1f

Preparation of D-glycero-D-manno-heptopyranose 1β,7-bisphosphate (7 or HBP-β). PtO$_2$ (8 mg, 35.2 μmol) was added to a solution of compound 6a (18 mg, 18.2 μmol) in dry MeOH (4 mL). The mixture was hydrogenolysed in a high-pressure reactor (Berghof) at 20° C. (p=20 bar). After 16 hours, the solids were removed by filtration using a 'sandwich filter' (3 frits stacked on top of each other in the following order: 20 μm, 10 μm, 5 μm), and rinsed with MeOH (4 mL). To the filtrate, Et$_3$N (10 mL, 18.2 μmol) was added and the solution concentrated in vacuo. A 1M NaOH aq solution (0.1 mL) was added to a solution of the crude in H$_2$O (0.3 mL) and MeOH (0.3 mL). After 3 hours, the solution was reduced to half volume under a flow of air and then loaded onto a PD-10 desalting column (GE Healthcare). Fractions containing the deprotected compound were concentrated in vacuo and purified by reverse-phase chromatography (C-18, H$_2$O-MeOH, 9:1→8:2→7:3→6:4→2: 8→0:10) to give 7 or HBP-β (5.8 mg, 82% pure) as a colorless, amorphous solid. $^1$H NMR (500 MHz, D20) δ 4.86 (dd, J 1.0 Hz, J 8.9 Hz, 1H, H-1), 3.99 (ddd, J 2.4 Hz, J 4.0 Hz, J 7.6 Hz, 1H, H-6), 3.87-3.82 (m, 1H, H-7a), 3.80 (d, J 3.3 Hz, 1H, H-2), 3.71-3.65 (m, 1H, H-7b), 3.58 (t, J 9.8 Hz, 1H, H-4), 3.46 (dd, J 3.3 Hz, J 9.8 Hz, 1H, H-3), 3.29 (dd, J 2.4 Hz, J 9.8 Hz, 1H, H-5); $^{13}$C NMR (126 MHz, D$_2$O, taken from HSQC) δ 94.9 (C-1), 77.0 (C-5), 72.5 (C-3), 70.8 (C-2), 69.8 (C-6), 66.1 (C-4), 63.5 (C-7). The NMR data of compound 7 or HBP-β are in agreement with the prior art [8].

Figure 32:
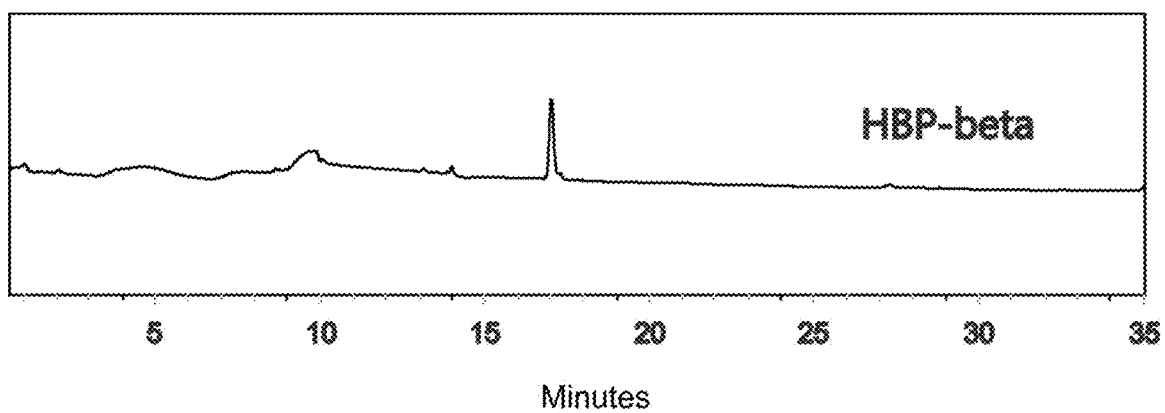
FIG. 32: Purity of HBP JS6 or HBP-β. Chromatogram of JS6 or HBP-β. Detector: PAD, Column: Carbopac™ Solvent A: NaOH, 0.1M, Solvent B: AcONa, 1M and NaOH 0.05M, Conditions: 0-100% B in 30 minutes and 100% solvent B for 5 minutes.

An HPLC analysis shows that compound 7 or HBP-β is pure; see FIG. 32.

As will be understood by a skilled person, variations may be made to the various chemical syntheses described above in Example 1 without departing from the invention.

Example 2—Preparation of D-glycero-D-manno-heptopyranose 1β,7-bisphosphate (JS6 or HBP-β) and D-glycero-D-manno-heptopyranose 1α,7-bisphosphate (JS5 or HBP-α)

Scheme 2 below outlines a chemical synthesis which leads to the preparation of D-glycero-D-manno-heptopyranose 1β,7-bisphosphate (JS6 or HBP-β) and D-glycero-D-manno-heptopyranose 1α,7-bisphosphate (JS5 or HBP-α). A mixture is obtained in each case, which may be enriched by one of the two compounds depending on the reaction conditions.

Certain intermediate compounds featured in Scheme 2 below were prepared, at least in part, following procedures known in the art. For example, compound 2 was prepared by a procedure disclosed by Okuda et al. [4]. Compounds 4, 5, 6, 7 and 8 were prepared following procedures derived from the disclosures of Brimacombe et al. [3,5]. Compound 9 was prepared by a procedure derived from the disclosure of Gizlek et al. [6]. Compounds 11, 12α, JS5 (or HBP-α) and JS6 (or HBP-β) were prepared by procedure derived from the disclosure of Zamyatina et al. [7].

Scheme 2. Chemical synthesis of D-glycero-D-manno-heptopyranose 1β,7-bisphosphate (JS6 or HBP-β) and D-glycero-D-manno-heptopyranose 1α,7-bisphosphate (JS5 or HBP-α).

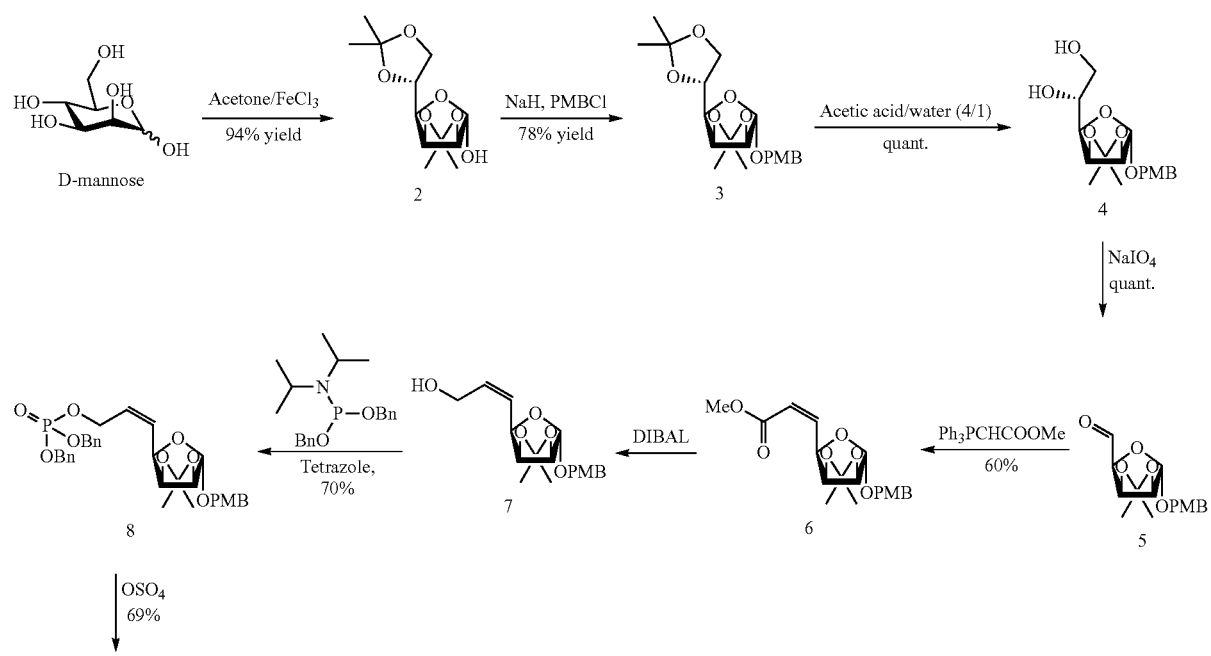

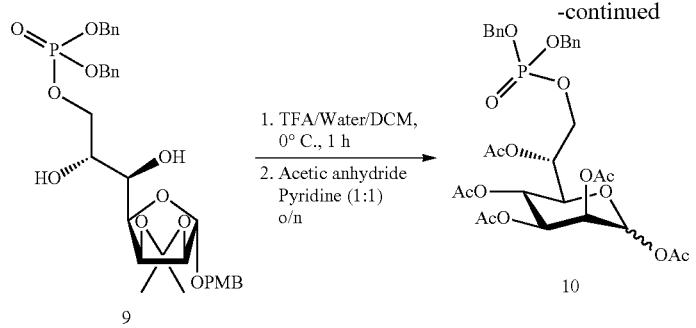
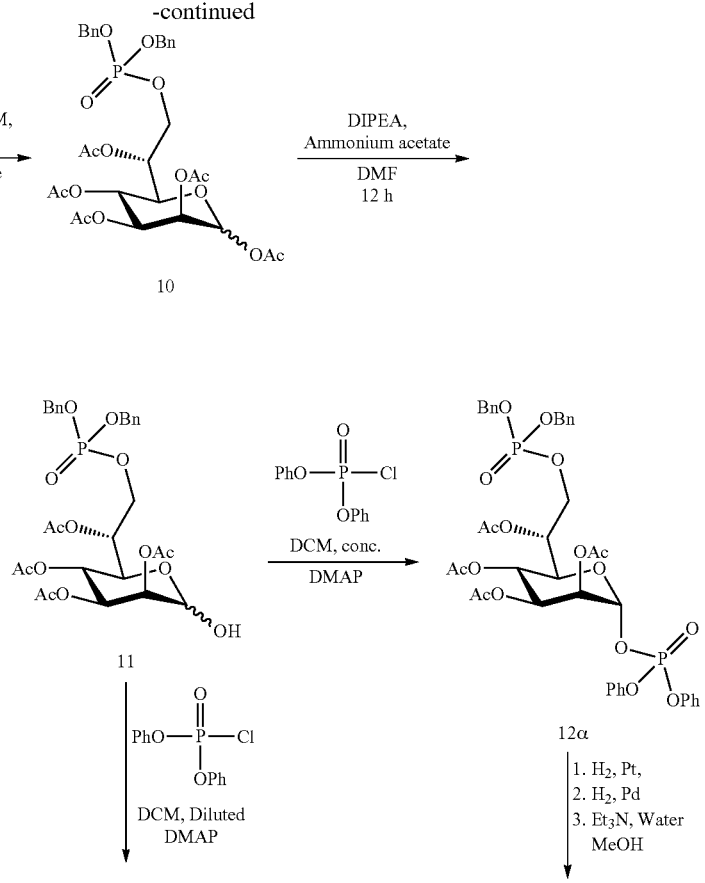
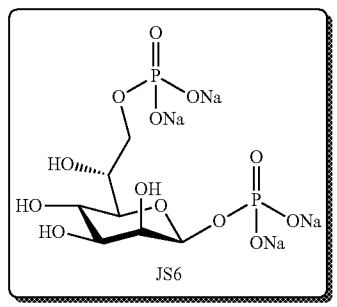
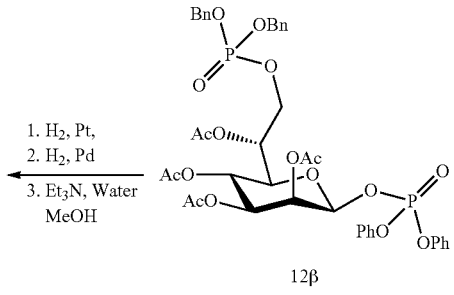
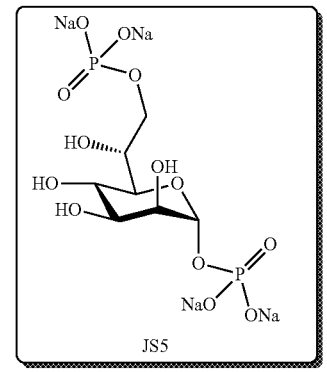

Example 2a

Compound 2 was prepared by the procedure according to Okuda et al. [4]. (2) $[\alpha]_D^{21}$=17.1 (c=0.67, CH$_2$Cl$_2$), MS (ESI): [M+H]$^+$ m/z Calcd for C$_{12}$H$_{21}$O$_6$, 261.1; found, 261.0. $^1$H NMR, (400 MHz, CDCl$_3$) δ 5.39 ($J_{H1',H2'}$=1.8 Hz, d, 1H, H1'), 4.82 ($J_{H3',H2'}$=5.8 Hz, $J_{H3',H4'}$=3.8 Hz, dd, 1H, H3'), 4.63 ($J_{H2',H3'}$=5.8 Hz, d, 1H, H2'), 4.42 (m, 1H, H5'), 4.20 ($J_{H4',H3'}$=3.6 Hz, dd, 1H, H4'), 4.08 (m, 2H, H6'), 3.2 (s, 1H, OH), 1.48 (3H, s, C$\underline{H}_3$COCH2',OCH3'), 1.47 (3H, s, C$\underline{H}_3$COCH5',OCH6'), 1.39 (3H, s, C$\underline{H}_3$COCH5',OCH6'), 1.34 (3H, s, C$\underline{H}_3$COCH2',OCH3'). $^{13}$C NMR (400 MHz, CDCl$_3$) δ 112.7 (C2',3'O$_2$C), 109.1 (C5',6'O$_2$C) 101.3 (C1'), 85.5 (C2'), 80.1 (C4'), 79.4 (C3'), 73.1 (C5'), 66.5 (C6'), 26.8 (C$\underline{H}_3$COCH5',OCH6'), 25.8 (C$\underline{H}_3$COCH2',OCH3'), 25.1 (C$\underline{H}_3$COCH5',OCH6'), 24.4 (C$\underline{H}_3$COCH2',OCH3').

Example 2b

Preparation of 4-methoxybenzyl 2,3,5,6-di-O-isopropylidene-α-D-mannofuranoside (3). To a solution of sodium hydride (60% in mineral oil, 5.23 g, 131 mmol) in anhydrous DMF (120 mL), was slowly added 2 (19.3 g, 74 mmol) in anhydrous DMF (60 mL) at 0° C. After 30 minutes, p-methoxybenzyl chloride (16.3 mL, 119.4 mmol) was injected dropwise and the mixture was stirred for 1 hour at 0° C. after which the reaction was quenched by the addition of MeOH (15 mL). This mixture was stirred for 5 minutes and poured slowly into water. It was then extracted with ethyl acetate and the combined organic layers washed with water. The ethyl acetate fraction was then dried with magnesium sulfate, filtered and concentrated. Purification of the residue on silica gel chromatography afforded title compound 3 (22.2 g, 58 mmol, 78%). ($R_f$=0.47, EtOAc/Hexanes, 3/7, v/v). $[\alpha]_D^{21}$=68.0 (c=0.63, $CH_2Cl_2$), MS (ESI): $[M+NH_4]^+$ m/z Calcd for $C_{20}H_{32}NO_7$, 398.2; found, 397.9. $^1$H NMR, (400 MHz, $CDCl_3$) δ 7.27 ($J_{\underline{CH}CCH2, \underline{CH}COMe}$=9 Hz, d, 2H, C$\underline{H}$CCH$_2$, PMB), 6.90 ($J_{\underline{CH}COMe, \underline{CH}CCH2}$=9 Hz, d, 2H, C$\underline{H}$COMe, PMB), 5.07 (s, 1H, H1'), 4.80 ($J_{H3',H2'}$=6 Hz, $J_{H3',H4'}$=3.7 Hz, dd, 1H, H3'), 4.65 ($J_{H2',H3'}$=6 Hz, d, 1H, H2'), 4.61 ($J_{CHA, CHB}$=11 Hz, ABX, 1H, CHA, PMB), 4.43 (m, 2H, CHB, PMB and H5'), 4.15 ($J_{H6'A, H6'B}$=8.5 Hz, $J_{H6'A,H5'}$=6.3 Hz, ABX, 1H, H6'A), 4.05 ($J_{H6'B, H6'A}$=8.5 Hz, $J_{H6'B,H5'}$=4.3 Hz, ABX, 1H, H6'B), 4.00 ($J_{H4',H3'}$=3.7 Hz, $J_{H4',H5'}$=7.8 Hz, dd, 1H, H4'), 3.82 (3H, s, $CH_3O$), 1.48 (6H, s, C$\underline{H_3}$COCH2',OCH3' and C$\underline{H_3}$COCH5',OCH6'), 1.42 (3H, s, C$\underline{H_3}$COCH5',OCH6'), 1.33 (3H, s, C$\underline{H_3}$COCH2',OCH3'). $^{13}$C NMR (400 MHz, $CDCl_3$) δ 159.4 ($\underline{C}$OMe), 129.8 ($\underline{C}$HCCH$_2$ PMB), 113.7 ($\underline{C}$HCCH$_2$ PMB), 112.7 (C2',3'O$_2$$\underline{C}$), 109.5 (C5',6'O$_2$$\underline{C}$) 105.2 (C1'), 84.9 (C2'), 80.2 (C4'), 79.5 (C3'), 73.0 (C5'), 68.8 ($\underline{C}$H$_2$, PMB), 67.0 (C6'), 55.1 (OMe), 26.8 ($\underline{C}$H$_3$COCH5',OCH6'), 25.8 ($\underline{C}$H$_3$COCH2',OCH3'), 25.0 ($\underline{C}$H$_3$COCH5',OCH6'), 24.3 ($\underline{C}$H$_3$COCH2',OCH3').

Example 2c

Preparation of 4-methoxybenzyl 2,3-O-isopropylidene-α-D-mannofuranoside (4). A solution of 3 (17.1 g, 45 mmol) in acetic acid/water (100 mL, 4/1, v/v) was stirred at RT overnight. The mixture was concentrated and coevaporated with toluene 4 times to afford title compound 4 (14.6 g, 43 mmol, 96%). ($R_f$=0.2, EtOAc/Hexanes, 3/7, v/v). $[\alpha]_D^{21}$=61.6 (C=0.78, $CH_2Cl_2$), MS (ESI): $[M+NH_4]^+$ m/z Calcd for $C_{17}H_{28}NO_7$, 358.2; found, 357.9. $^1$H NMR, (400 MHz, $CDCl_3$) δ 7.27 ($J_{\underline{CH}CCH2, \underline{CH}COMe}$=9 Hz, d, 2H, C$\underline{H}$CCH$_2$, PMB), 6.90 ($J_{\underline{CH}COMe, \underline{CH}CCH2}$=9 Hz, d, 2H, C$\underline{H}$COMe, PMB), 5.12 (s, 1H, H1'), 4.87 ($J_{H3',H2'}$=6.0 Hz, $J_{H3',H4'}$=3.7 Hz, dd, 1H, H3'), 4.66 ($J_{H2',H3'}$=6 Hz, d, 1H, H2'), 4.59 ($J_{CHA, CHB}$=11.3 Hz, ABX, 1H, CHA, PMB), 4.45 ($J_{CHB, CHA}$=11.5 Hz, ABX, 1H, CHB, PMB), 4.05 (m, 1H, H5'), 4.00 ($J_{H4',H3'}$=3.7 Hz, $J_{H4',H5'}$=7.8 Hz, dd, 1H, H4'), 3.82 (3H, s, $CH_3O$), 3.87 (m, 1H, H6'A), 3.72 (m, 1H, H6'A) 1.50 (3H, s, C$\underline{H_3}$COCH$_2$',OCH$_3$'), 1.35 (3H, s, C$\underline{H_3}$COCH2',OCH3'). $^{13}$C NMR (400 MHz, $CDCl_3$) δ 159.4 ($\underline{C}$OMe), 129.8 ($\underline{C}$HCCH$_2$ PMB), 113.9 ($\underline{C}$HCCH$_2$ PMB), 112.7 (C2',3'O$_2$$\underline{C}$), 105.0 (C1'), 84.8 (C2'), 80.0 (C3'), 79.1 (C4') 70.4 (C5'), 68.8 ($\underline{C}$H$_2$, PMB), 64.4 (C6'), 55.2 (OMe), 25.8 ($\underline{C}$H$_3$COCH5',OCH6'), 24.4 ($\underline{C}$H$_3$COCH2',OCH3').

Example 2d

Preparation of 4-methoxybenzyl 2,3-O-isopropylidene-α-D-lyxo-pentodialdo-1,4-furanoside (5). To a solution of 4 (3.4 g, 9.9 mmol) in acetone/water (6/1, v/v) was added sodium periodate (3.17 g, 14.8 mmol) at 0° C. for 3 hours and then warmed up to RT slowly overnight. Upon reaction, the sodium iodate salt precipitates forming a thick suspension. The solvents were then evaporated and 5 dissolved in ethyl acetate. The solution was then washed with saturated ammonium chloride and then brine. The ethyl acetate layer was then dried using $MgSO_4$, filtered and evaporated to give pure title compound 5. HRMS (ESI): $[M+H]^+$ m/z Calcd for $C_{16}H_{20}NaO_6$, 331.1158; found, 331.1146. $^1$H NMR, (400 MHz, $CDCl_3$) δ 9.70 (bs, 1H, H5'), 7.27 (2H, C$\underline{H}$CCH$_2$, PMB, overlaps with $CHCl_3$), 6.90 ($J_{\underline{CH}COMe,\underline{CH}CCH2}$=8.7 Hz, d, 2H, C$\underline{H}$COMe, PMB), 5.29 (s, 1H, H1'), 5.11 (m, 1H, H3'), 4.70 ($J_{H2',H3'}$=5.9 Hz, d, 1H, H2'), 4.64 ($J_{CHA, CHB}$=11.5 Hz, ABX, 1H, CHA, PMB), 4.48 ($J_{CHB, CHA}$=11.5 Hz, ABX, 1H, CHB, PMB), 4.44 ($J_{H4',H3'}$=5.0 Hz, d, 1H, H4'), 3.83 (3H, s, $CH_3O$), 1.44 (3H, s, C$\underline{H_3}$COCH2',OCH3'), 1.29 (3H, s, C$\underline{H_3}$COCH2',OCH3'). $^{13}$C NMR (400 MHz, $CDCl_3$) δ 197.8 ($\underline{C}$(O)H) 159.6 ($\underline{C}$OMe), 129.8 ($\underline{C}$HCCH$_2$ PMB), 114.0 ($\underline{C}$HCOMe), 113.5 (C2',3'O$_2$$\underline{C}$), 105.8 (C1'), 84.8 (C2'), 84.3 (C4'), 81.1 (C3'), 69.2 ($\underline{C}$H$_2$, PMB), 55.4 (OMe), 26.0 and 24.7 ($\underline{C}$H$_3$COCH2',OCH3').

Example 2e

Preparation of methyl [methoxybenzyl (Z)-5,6-dioxy-2,3-O-isopropylidene-α-D-lyxo-hept-5-enofuranosid]uronate (6). To aldehyde 5 (14 g, 38 mmol) dissolved in anhydrous toluene (200 mL) at 0° C. was added (methoxycarbonylmethylene)phosphorane (17.5 g, 50 mmol). The reaction was kept under nitrogen for 2 hours and concentrated. Column flash chromatography afforded ester 6 in 60% yield (8.3 g, 23 mmol). Rf: 0.65 (1:1, Hexane:Ethyl Acetate, v:v). $[\alpha]_D^{21}$=−25.6 (C=0.75, $CH_2Cl_2$), HRMS (ESI): $[M+Na]^+$ m/z Calcd for $C_{19}H_{27}NaO_7$, 387.1420; found, 387.1426. $^1$H NMR, (400 MHz, $CDCl_3$) δ 7.28 ($J_{\underline{CH}CCH2, \underline{CH}COMe}$=9 Hz, d, 2H, C$\underline{H}$CCH$_2$, PMB), 6.90 ($J_{\underline{CH}COMe, \underline{CH}CCH2}$=9 Hz, d, 2H, C$\underline{H}$COMe, PMB), 6.38 ($J_{H5',H4'}$=7 Hz, $J_{H5',H6'}$=11 Hz, dd, 1H, H5'), 6.02 ($J_{H6',H5'}$=11 Hz, d, 1H, H6'), 5.50 (m, 1H, H4'), 5.13 (s, 1H, H1'), 5.07 ($J_{H3',H2'}$=6 Hz, $J_{H3',H4'}$=4 Hz, dd, 1H, H3'), 4.69 ($J_{H2',H3'}$=6 Hz, d, 1H, H2'), 4.65 ($J_{CHA, CHB}$=11 Hz, ABX, 1H, CHA, PMB), 4.43 ($J_{CHB, CHA}$=11 Hz, ABX, 1H, CHB, PMB), 3.83 (3H, s, $CH_3O$, PMB), 3.76 (3H, s, $CH_3O$, C(O)Me), 1.47 (3H, s, C$\underline{H_3}$COCH2',OCH3. $^{13}$C NMR (400 MHz, $CDCl_3$) δ 166.0 ($\underline{C}$(O)OMe), 159.4 ($\underline{C}$OMe, PMB), 145.2 (C5'), 129.8 ($\underline{C}$HCCH$_2$ PMB), 129.3 ($\underline{C}$OMe, PMB), 120.7 (C6'), 113.9 ($\underline{C}$HCCH$_2$ PMB), 112.4 (C2',3'MeO$_2$$\underline{C}$), 104.9 (C1'), 85.2 (C2'), 81.5 (C3'), 77.5 (C4'), 68.5 ($\underline{C}$H$_2$, PMB), 55.2 (OMe, PMB), 51.2 (OMe), 25.7 and 25.2 ($\underline{C}$H$_3$COCH2',OCH3').

Example 2f

Preparation of methoxybenzyl (Z)-5,6-dideoxy-2,3-O-isopropylidene-α-D-lyxo-hept-5-enofuranoside (7). DIBAL (6.2 mmol, 6.2 mL) was added to a stirred solution of ester 6 (600 mg, 1.64 mmol) in anhydrous dichloromethane (10 mL) at 0° C. under $N_2$. The reaction was shown to be to completion after 2 hours via TLC (Rf: 0.11, 2/8, EA/Hex, v/v). DCM (200 mL) was added to the solution as well as saturated ammonium chloride. A fluffy gel like solid formed and had to be filtered over glass wool and rinsed with DCM and ammonium chloride until the compound was entirely removed from the gel. The filtrate was then partitioned and the DCM fraction was washed with water. The sample was then purified using flash chromatography to obtain title compound 7 (80%, 443 mg, 1.32 mmol). $[\alpha]_D^{21}$=41.3 (C=1.2, $CH_2Cl_2$), MS (ESI): $[M+Na]^+$ m/z Calcd for $C_{18}H_{24}NaO_6$, 359.14; found, 359.14. $^1$H NMR, (400 MHz, $CDCl_3$) δ 7.29 ($J_{\underline{CH}CCH2, \underline{CH}COMe}$=8.5 Hz, d, 2H, C$\underline{H}$CCH$_2$, PMB), 6.91 ($J_{\underline{CH}COMe, \underline{CH}CCH2}$=8.6 Hz, d, 2H, C$\underline{H}$COMe, PMB), 5.99 (m, 1H, H6'), 5.82 (m, 1H, H5'), 5.12 (s, 1H, H1'), 4.80 (m, 1H, H4'), 4.70 ($J_{H3',H2'}$=5.8 Hz, $J_{H3',H4'}$=3.7 Hz, dd, 1H, H3'), 4.65 ($J_{H2',H3'}$=5.6 Hz, d, 1H, H2'), 4.65 ($J_{CHA, CHB}$=11.3 Hz, ABX, 1H, CHA, PMB), 4.47 ($J_{CHB, CHA}$=11.0 Hz, ABX, 1H, CHB, PMB), 3.83 (3H, s, $CH_3O$, PMB), 1.49 (3H, s, C$\underline{H_3}$COCH2',OCH3'), 1.33 (3H, s, C$\underline{H_3}$COCH2',OCH3') $^{13}$C NMR (400 MHz, $CDCl_3$) δ 159.4 ($\underline{C}$OMe, PMB), 133.2 (C6'), 129.8 ($\underline{C}$HCCH$_2$ PMB), 129.3 (COMe, PMB), 126.4 (C5'), 113.9 (CHCCH₂ PMB), 112.6 (C2',3'MeO₂C), 104.9 (C1'), 85.4 (C2'), 81.2 (C3'), 75.7 (C4'), 68.7 (CH₂, PMB), 59.1 (C6'), 55.4 (OMe, PMB), 26.0 and 24.8 (CH₃COCH2',OCH3').

Example 2g

Preparation of methoxybenzyl 7-O-[bis(benzyloxy)phosphoryl]-5,6-dideoxy-2,3-O-isopropylidene-α-D-lyxo-(Z)-hept-5 enofuranoside (8). To a solution of 7 (105 mg, 31 µmol) and bisbenzyloxy-N,N-diisopropylaminophosphine (270 mg, 78 µmol) in anhydrous DCM (1 mL) was added tetrazole (66 mg, 94 µmol) in anhydrous acetonitrile (0.5 mL). After a few minutes a white precipitate forms and monitoring using TLC shows the triester formation (RF=0.47, 1:4, v:v, EA:Hex). After 2 hours, the solution was then cooled to 0° C. with an ice bath and t-BuOOH was slowly added (94 µL, 5M, 470 µmol) and was stirred overnight at RT. The reaction mixture was then diluted (diethyl ether:EA, v:v, 2:1) and washed with NaHCO₃ sat. and water. The organic fraction was then dried with MgSO₄, filtered and concentrated. After column chromatography using toluene:diethylether (1:1) a yellowish oil was obtained in 70% yield (131.2 mg, 22 µmol). $[\alpha]_D^{21}$=22.9 (c=0.73, CH₂Cl₂), MS (ESI): [M+Na]⁺ m/z Calcd for C₃₂H₃₇NaO₉P, 619.2; found, 619.3. ¹H NMR, (400 MHz, CDCl₃) δ 7.36 (m, 10H, Bn), 7.27 ($J_{CHCCH2,\ CHCOMe}$=8.6 Hz, d, 2H, CHCCH₂, PMB), 6.89 ($J_{CHCOMe,CHCCH2}$=8.6 Hz, d, 2H, CHCOMe, PMB), 5.85 (m, 1H, H5'), 5.09-5.04 (m, 5H, Bn and H1'), 4.72 (m, 1H, H4'), 4.67 (m, 2H, H6'), 4.63 (bs, 2H, H2' and H3'), 4.61 ($J_{CHA,\ CHB}$=12.5 Hz, ABX, 1H, CHA, PMB), 4.42 ($J_{CHB,\ CHA}$=11.2 Hz, ABX, 1H, CHB, PMB), 3.81 (3H, s, CH₃O, PMB), 1.46 (3H, s, CH₃COCH2',OCH3), 1.29 (3H, s, CH₃COCH2',OCH3). ¹³C NMR (400 MHz, CDCl₃) δ 159.4 (COMe, PMB), 135.8 and 135.7 (CCH₂O, Bn), 129.8 (CHCCH₂ PMB), 129.2 (COMe, PMB), 128.9-127.2 (Bn), 113.9 (CHCCH₂ PMB), 112.5 (C2',3'MeO₂C), 105.0 (C1'), 85.3 (C2'), 81.4 (C3'), 75.6 (C4'), 69.4 and 69.3 (CH₂Ph), 68.6 (CH₂, PMB), 63.6 (C6'), 55.0 (OMe, PMB), 26.0 and 24.5 (CH₃COCH2',OCH3'). ³¹P NMR (400 MHz, CDCl₃) δ −0.7.

Example 2h

Preparation of methoxybenzyl 7-O-[bis(benzyloxy)phosphoryl]-2,3-O-isopropylidene-D-glycero-α-D-manno heptofuranoside (9). Alkene 2 (3 g, 5.4 mmol) was stirred with NMMO (2.7 mL, 10.8 mmol, 50% in water) for 30 minutes at RT in acetone:dioxane:water (1:2:1, v:v:v). Then osmium tetraoxide (2.74 mL, 0.4 mmol, 4% in water) was added to the solution. The solution turned slowly yellow. After 5 hours, TLC monitoring showed that the reaction was completed. The solution was treated with ice cold HCL (5M) and then with 45% Na₂S₂O₅ and water. A total 92% yield was obtained however, this contained 31% of the gulose derivative. Using flash chromatography, the most part of the gulose was removed and the resulting oil was crystallized using hexane and dichloromethane. This afforded pure 9 in 69% yield (2.34 g, 3.7 mmol). Rf=0.47 in ethyl acetate. $[\alpha]_D^{21}$=41.0 (C=0.51, CH₂Cl₂), HRMS (ESI): [M+Na]⁺ m/z Calcd for C₃₂H₃₉NaO₁₁P, 653.2128; found, 653.2128. ¹H NMR, (600 MHz, CDCl₃) δ 7.37-7.31 (m, 10H, Bn), 7.23 ($J_{CHCCH2,\ CHCOMe}$=8.6 Hz, d, 2H, CHCCH₂, PMB), 6.86 ($J_{CHCOMe,\ CHCCH2}$=8.6 Hz, d, 2H, CHCOMe, PMB), 5.12-5.01 (m, 5H, Bn and H1'), 4.89 ($J_{H3',H2}$=5.9 Hz, $J_{H3',H4'}$=3.6 Hz, dd, 1H, H3'), 4.61 (d, $J_{H2',H3'}$=6.0 Hz, 1H, H2'), 4.56 ($J_{CHA,\ CHB}$=11.4 Hz, ABX, 1H, CHA, PMB), 4.38 ($J_{CHB,\ CHA}$=11.3 Hz, ABX, 1H, CHB, PMB), 4.30-4.20 (m, 2H, H7'), 4.16 ($J_{H4',H3'}$=3.6 Hz, $J_{H4',H5'}$=6.9 Hz, dd, 1H, H4'), 4.01 (m, 1H, H5'), 3.93 (m, 1H, H6'), 3.79 (3H, s, CH₃O, PMB), 1.44 (3H, s, CH₃COCH2',OCH3), 1.30 (3H, s, CH₃COCH2',OCH3). ¹³C NMR (600 MHz, CDCl₃) δ 159.8 (COMe, PMB), 135.9 (CCH₂O, Bn), 130.1 (CHCCH₂ PMB), 128.9-128.4 (Bn), 114.3 (CHCCH₂ PMB), 113.0 (C2',3'MeO₂C), 105.6 (C1'), 85.2 (C2'), 80.9 (C3'), 79.4 (C4'), 73.3 (C6'), 70.0-69.6 (CH₂Ph), 69.7 (C7'), 69.6 (C5'), 69.2 (CH₂PMB), 55.6 (OMe, PMB), 26.3 and 24.8 (CH₃COCH2',OCH3'), ³¹P NMR (400 MHz, CDCl₃) δ 0.8.

Example 2i

Preparation of 1,2,3,4,6-penta-O-acetyl-(7-O-[bis(benzyloxy)phosphoryl]-D-glycero-α-D-manno heptopyranoside) (10). Compound 9 (120 mg, 190 µmol) was stirred with DCM (5 mL) and water (1 mL) at 0° C. Then TFA (5 mL) was added and stirred for 1 hour. After few minutes a pink shade appears, this transforms slowly into a purple shade as the reaction warms up to RT. After this time, the reaction was coevaporated with toluene and then neutralized with triethylamine until a pH of 7 was reached. After further coevaporations, the compound was dissolved in anhydrous DMF (200 µL), then anhydrous pyridine (1 mL) and acetic anhydride (1 mL) were added and stirred for 16 hours at RT. DCM was added and washed with NaHCO₃ until a neutral pH was reached and brine. After drying over Na₂SO₄ and concentrated, the compound was columned using flash chromatography to obtain title compound 10 (1:0.6, α:β). This afforded pure 10 in 85% yield (110 mg, 162 µmol). Rf=0.14 in ethyl acetate:hexane (1:1, v:v). MS (ESI): [M+Na]⁺ m/z Calcd for C₃₁H₃₇NaO₁₅P, 703.17; found, 703.17. ¹H NMR, (600 MHz, CDCl₃) δ 7.4-7.3 (m, 10H, Bn), 6.04 (s, H1'α), 5.82 (s, H1'β), 5.43 (m, H2'β), 5.37-5.31 (H4'α and H3'α), 5.27-5.20 (m, H4' β and H6'β, H2'α), 5.17 (m, H6'α), 5.12-5.00 (m, CH₂Bn, H3'β), 4.46-4.20 (H7'α and β), 4.11 ($J_{H5'α,H4'α}$=9.0 Hz, $J_{H5'α,H6'α}$=4.1 Hz, dd, H5'α), 3.80 ($J_{H5'β,H4'β}$=9.1 Hz, $J_{H5'β,H6'β}$=4.1 Hz, dd, H5'β). ¹³C NMR (400 MHz, CDCl₃) δ 170-168 (CH₃C(O)), 135.8-135.4 (CCH₂O, Bn), 128.7-128.4 (CBn), 128.0-127.7 (CHBn), 90.0 (C1'α and β), 73.7 (C5'β), 71.0 ($J_{C6'α,β}$=7.9 Hz, d, C6'α), (C4'α), 70.9 (C5'α), 70.8 (C6'β), 70.0 (C3'β), 69.4 and 69.3 (CH₂Ph), 68.7 (C3'α), 68.1 (C2'α), 67.5 (C2'β), 66.2 (C4'β), 64.7 ($J_{C7'α,β}$=5.1 Hz, d, C7'α), 64.7 ($J_{C7'α,β}$=5.5 Hz, d, C7'β), 20.8-20.4 (CH₃C(O)).

Example 2i

Preparation of 2,3,4,6-penta-O-acetyl-(7-O-[bis(benzyloxy)phosphoryl]-D-glycero-α-D-manno heptopyranoside) (11). Compound 10 (50 mg, 74 µmol) was dissolved into DMF (5 mL) and to this was added diisopropylethylamine (1 mL) and ammonium acetate (200 mg). The reaction was stirred for 16 hours at RT after which TLC monitoring showed that the reaction was to completion (rf 0.8, EA:PE, 1:1, v:v). The reaction mixture was diluted with DCM, washed with NaHCO₃ sat. and water. The DCM fraction was then dried with Na₂SO₄, filtered and concentrated. Column chromatography afforded title compound 11 in quantitative yield (47 mg, 74 µmol). HRMS (ESI): [M+Na]⁺ m/z Calcd for C₂₉H₃₅NaO₁₄P, 661.1662; found, 661.1683. ¹H NMR, (400 MHz, CDCl₃) δ 7.4-7.3 (m, 10H, Bn), 5.47 ($J_{H3',H2'}$=3.5 Hz, $J_{H3',H4'}$=9. Hz, dd, 1H, H3'), 5.29 ($J_{H2',H1'}$=1.7 Hz, $J_{H2',H3'}$=3.5 Hz, dd, 1H, H4'), 5.25 ($J_{H4',H3'}$=9.8 Hz, $J_{H4',H5'}$=9.8 Hz, dd (apt), 1H, H4'), 5.12 (d, $J_{H1',H2'}$=1.4 Hz, 1H, H1'), 5.08-5.01 (m, 3H, CH₂Bn and H6'), 4.45 and 4.11 (m, 1H, H7'), 4.28 ($J_{H5',H6'}$=7.4 Hz, $J_{H5',H4'}$=9.8 Hz, dd, 1H, H5'), 2.11 (s, 3H, C$\underline{H}_3$COOCH2'), 2.03 (s, 3H, C$\underline{H}_3$COOCH4'), 2.02 and 2.01 (s, 3H, C$\underline{H}_3$COOCH3' and C$\underline{H}_3$COOCH6'). $^{130}$C NMR (400 MHz, CDCl$_3$) δ 170.5-169.9 ($\underline{C}$(O)), 135.9-135.6 ($\underline{C}$Bn), 129.2-128.2 ($\underline{C}$HBn), 92.7 (C1'), 73.1 ($J_{C6',P}$=5.8 Hz, d, C6'), 70.3 (C2'), 70.3-70.0 ($\underline{CH}_2$Bn), 69.3 (C3'), 68.7 (C4'), 66.1 (C5'), 65.7 ($J_{C6',P}$=5.7 Hz, C7'), 21.2-20.9 ($\underline{CH}_3$). $^{31}$P NMR (400 MHz, CDCl$_3$) δ −1.0.

Example 2k

Preparation of diphenyl (2,3,4,6-tetra-O-acetyl-[7-O-(bis[benzyloxy]phosphoryl)-D-glycero-α-D-manno-heptopyranosyl) phosphate (12α). Compound 11 (4 mg, 6 μmol) was coevaporated together with diphenyl phosphoryl chloride (2 μL, 10 μmol) and dried under vacuum. After 2 hours the compounds were dissolved in anhydrous DCM (0.5 mL) and DMAP (4 mg, 31 μmol) after 2 hours under N$_2$, the reaction was diluted with DCM and washed with TEAB buffer (until a basic pH was reached), water and brine. The mixture was dried with Na$_2$SO$_4$, filtered and concentrated under reduced pressure. Flash chromatography using hexane:diethyl ether gave title compound 12α in 54% yield (3.2 mg, 3.4 μmol, α:β, 3:1). m/z Calcd for C$_{41}$H$_{44}$NaO$_{17}$P$_2$, 893.1951; found, 893.1943. $^1$H NMR, (600 MHz, CDCl$_3$) δ 7.34-7.06 (m, 2OH, Bn and Ph), 5.65 ($J_{H1',H2'}$=1.9 Hz, $J_{H1',P}$=7.3 Hz, dd, 1H, H1'), 5.38 ($J_{H3',H2'}$=3.2 Hz, $J_{H3',H4'}$=2.18 Hz, dd, 1H, H3'), 5.33 (H4'), 5.30 (H2'), 5.17 (m, 1H, H6'), 5.08-5.00 (m, 4H, C$\underline{H}_2$Bn), 4.29 (m, 2H, H7'), 4.23 (m, 1H, H5'), 2.11-2.01 (C$\underline{H}_3$). $^{13}$C NMR (400 MHz, CDCl$_3$, from HSQC) δ 130.7-127.0 (Bn), 125.6 and 120.0 (Ph), 95.5 (C1'), 72.1 (C5'), 70.4 (C6'), 69.3 (C$\underline{H}_2$Bn), 68.1 (C3'), 68.2 (C2'), 65.7 (C4'), 64.5 (C7'), 20.6 (C$\underline{H}_3$). $^{31}$P NMR (400 MHz, CDCl$_3$) δ −0.53 and −13.42.

Example 2l

Preparation of diphenyl (2,3,4,6-tetra-O-acetyl-[7-O-(bis[benzyloxy]phosphoryl)-D-glycero-β-D-manno-heptopyranosyl) phosphate (12β). Compound 11 (29.3 mg, 46 μmol) was coevaporated separately from diphenyl phosphoryl chloride (83 μL, 460 μmol) and dried under vacuum. After 2 hours 11 was dissolved in anhydrous DCM (1 mL) and DMAP (6 mg, 46 μmol) was added. Phosphoryl chloride was dissolved into DCM (1 mL) and using a syringe pump, dropped at a rate of 0.5 mL/h over 2 hours under N$_2$, the reaction was to completion over 5 hours. The reaction was diluted with DCM and washed with TEAB buffer (until a basic pH was reached), water and brine. The mixture was dried with Na$_2$SO$_4$, filtered and concentrated under reduced pressure. Flash chromatography using hexane: diethyl ether gave title compound 12R in 75% yield (30 mg, 35 μmol, α:β, 1:4). $^1$H NMR, (400 MHz, CDCl$_3$) δ 7.4-7.1 (m, 2OH, Bn and Ph), 5.67 ($J_{H1',H2'}$=1.7 Hz, $J_{H1',P}$=7.5 Hz, dd, 1H, H1'), 5.40 ($J_{H2',H1'}$=1.7 Hz, $J_{H2',H3'}$=3.1 Hz, dd, 1H, H2'), 5.31 (m, 1H, H6'), 5.21 ($J_{H4',H3'}$=$J_{H4',H5'}$=7.9 Hz, dd (apt), 1H, H4'), 5.08 ($J_{H3',H2'}$=3.1 Hz, $J_{H3',H4'}$=7.9 Hz, dd, 1H, H3'), 5.08-5.01 (m, 3H, C$\underline{H}_2$Bn), 3.89 ($J_{H5',H6'}$=5.8 Hz, $J_{H5',H4'}$=7.3 Hz, dd, 1H, H5'), 4.24 (m, 2H, H7'), 2.06, 2.02, 2.00, 1.98 (CH$_3$). $^{13}$C NMR (400 MHz, CDCl$_3$) δ 170.0, 169.9, 169.8, 169.7 (C(O)CH$_3$), 150.5, 150.4, 150.3, 150.2 (C, Ph and Bn), 136.0, 135.9, 135.9, 135.8 (CH, Ph and Bn), 130.14, 130.10 (CH, OBn), 128.8 (m, CH, OBn), 128.12 and 128.09 (CH, OPh), 126.0 and 128.9 (CH, OPh), 120.34 (m, CH, OPh), 94.84 ($^2J_{31, C1'}$=4.6 Hz, C1'), 73.3 (C5'), 70.7 ($^3J_{31P, C6'}$=7.2 Hz, C6'), 69.5 (m, CH$_2$Bn), 69.1 (C3'), 67.2 ($^3J_{31P, C2'}$=7.3 Hz, C2'), 66.2 (C4'), 64.9 ($^2J_{31P, C7'}$=5.7 Hz, C7'), 20.8, 20.7, 20.5 (C$\underline{H}_3$). $^{31}$P NMR (400 MHz, CDCl$_3$) δ −0.36 and −13.27.

Example 2m

Preparation of D-glycero-D-manno-heptopyranose 1β,7-bisphosphate (JS6 or HBP-β). Compound 12R (6 mg, 7 μmol) was stirred in anhydrous methanol at RT with PtO$_2$ under balloon pressure for 48 hours. After filtering over celite and concentration, the compound was again dissolved in anhydrous methanol and under a H$_2$ atmosphere. After 48 hours of stirring, filtration over celite and concentration under reduced pressure, the compound was dissolved into methanol:water:trimethylamine (7:3:1, v:v:v) for 3 hours after which it was concentrated and freeze dried over water. Purification on a desalting column (G-15) exchanging the trimethylamine ions for sodium ions using Dowex-Na gave title compound JS6 or HBP-β in 90% yield (2 mg, 5 μmol). NMR assignments are provided herein above. m/z Calcd for C7H$_{16}$NaO$_{13}$P$_2$, 392.9964; found, 392.9941.

Example 2n

Preparation of D-glycero-D-manno-heptopyranose 1α,7-bisphosphate (JS5 or HBP-α). Compound 12α (5 mg, 6 μmol) was globally deprotected as described above at Example 2m. After dissolving the compound in brine, it was purified over a desalting column (G-15) eluting with water. This afforded JS5 or HBP-α in 27% yield. (0.5 mg, 1.3 μmol). $^1$H NMR, (400 MHz, D$_2$O) δ 5.24 ($J_{H1',P}$=7.8 Hz, d, 1H, H1'), 4.09 (bs, 1H, H6'), 3.97 (bs, 1H, H7'A), 3.87-3.81 (bs, 3H, H5', H2', H7'B), 3.80 ($J_{H3',H2'}$=3.1 Hz, $J_{H3',H4'}$=9.9 Hz, dd, 1H, H3'), 3.73 ($J_{H4',H3'\ and\ H4',\ H5'}$=9.8 Hz, appt however known dd with same coupling constant, 1H, H4'). $^{13}$C NMR (400 MHz, D$_2$O), from HSQC b 95.9 (C1'), 71.5 (C2'), 71.0 (C3'), 67.8 (C4'), 71.5 (C6'), 65.9 (C7'), 74.0 (C5'). $^{31}$P NMR (400 MHz, CDCl$_3$) δ 2.68 and 0.78.

Figure 33:
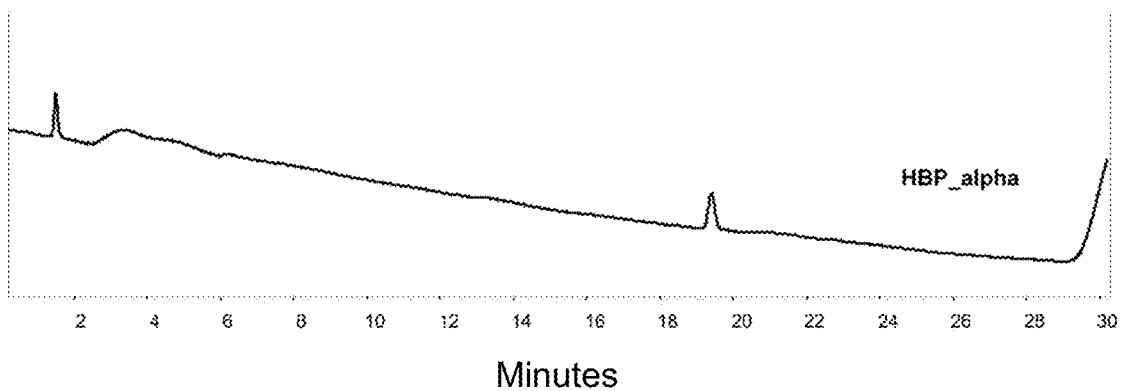
FIG. 33: Purity of HBP JS5 or HBP-α. Chromatogram of JS5 or HBP-α. Detector: PAD, Column: Carbopac™ Solvent A: NaOH, 0.1M, Solvent B: AcONa, 1M and NaOH 0.05M, Conditions: 0-100% B in 30 minutes.

An HPLC analysis shows that compound JS5 or HBP-α is pure; see FIG. 33.

Example 2o

Figure 31:
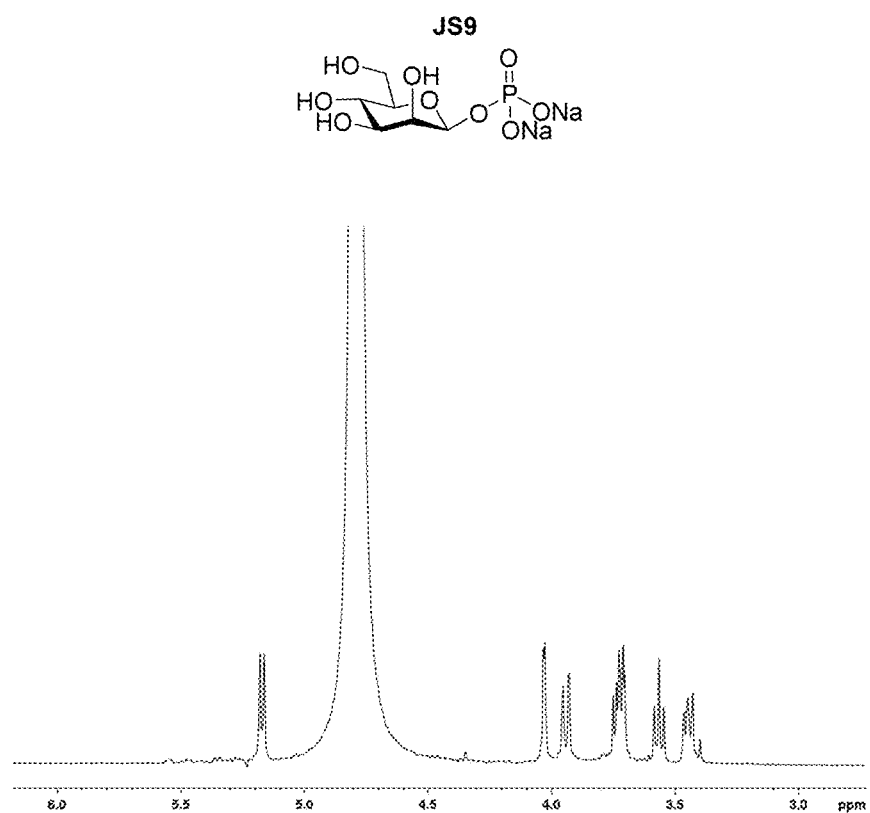
FIG. 31: $^1$H NMR of compound JS9 or Man-1β-P.
Figure 34:
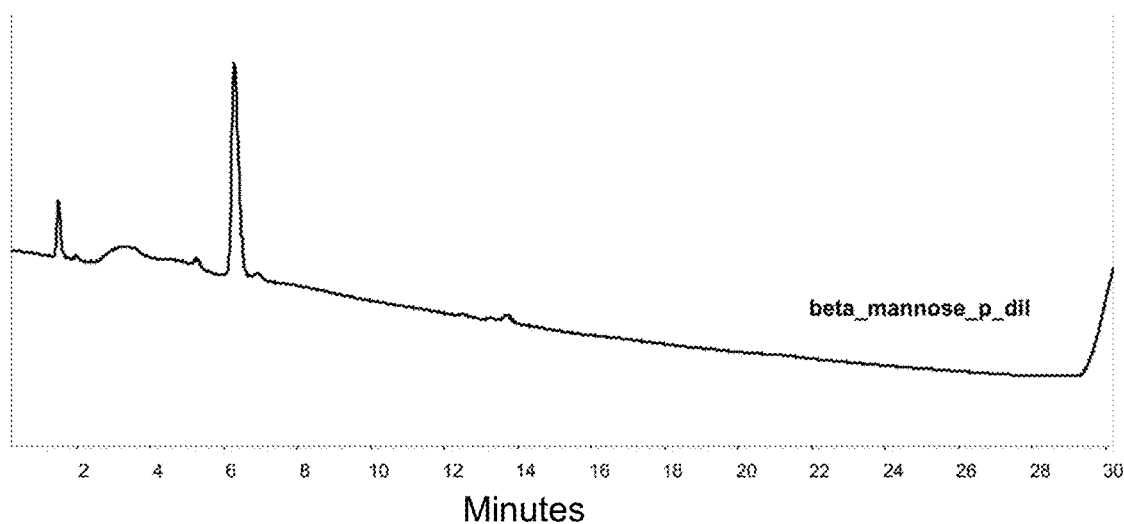
FIG. 34: Purity of JS9 or Man-1β-P. Chromatogram of JS9 or Man-1β-P. Detector: PAD, Column: Carbopac™ Solvent A: NaOH, 0.1M, Solvent B: AcONa, 1M and NaOH 0.05M, Conditions: 0-100% B in 30 minutes.

Preparation of D-mannose 1β-phosphate (JS9 or Man-1β-P), was as described by Zamyatina et al. [7], however starting from acetylated D-mannose instead of acetylated heptose and purifying in brine and eluting through a G-15 column to exchange the trimethylamine salt for sodium. The spectrum obtained (FIG. 31) is in accordance with the literature data [12]. An HPLC analysis shows that compound JS9 or Man-1β-P is pure; see FIG. 34.

As will be understood by a skilled person, variations may be made to the various chemical syntheses described above in Example 2 without departing from the invention. For example, P(O)(OPh)$_2$Cl can be used for the preparation of compound 8 from compound 7 instead of bisbenzyloxy-N,N-diisopropylaminophosphine, and iPr$_2$NP(OBn)$_2$ followed by t-BuOOH can be used for the preparation of compound 12a from compound 11 instead of diphenyl phosphoryl chloride.

As will be understood by a skilled person, in compounds 12α and 12β, the protective groups of the phosphate at positions 1 and 7 may be inverted. This is outlined in Scheme 2 and Scheme 2A.

Furthermore, as will be understood by a skilled person, in compound 12a, the protective groups of the phosphate at positions 1 and 7 may be inverted.

Example 3—Biological Experiments

Example 3a

Figure 35:
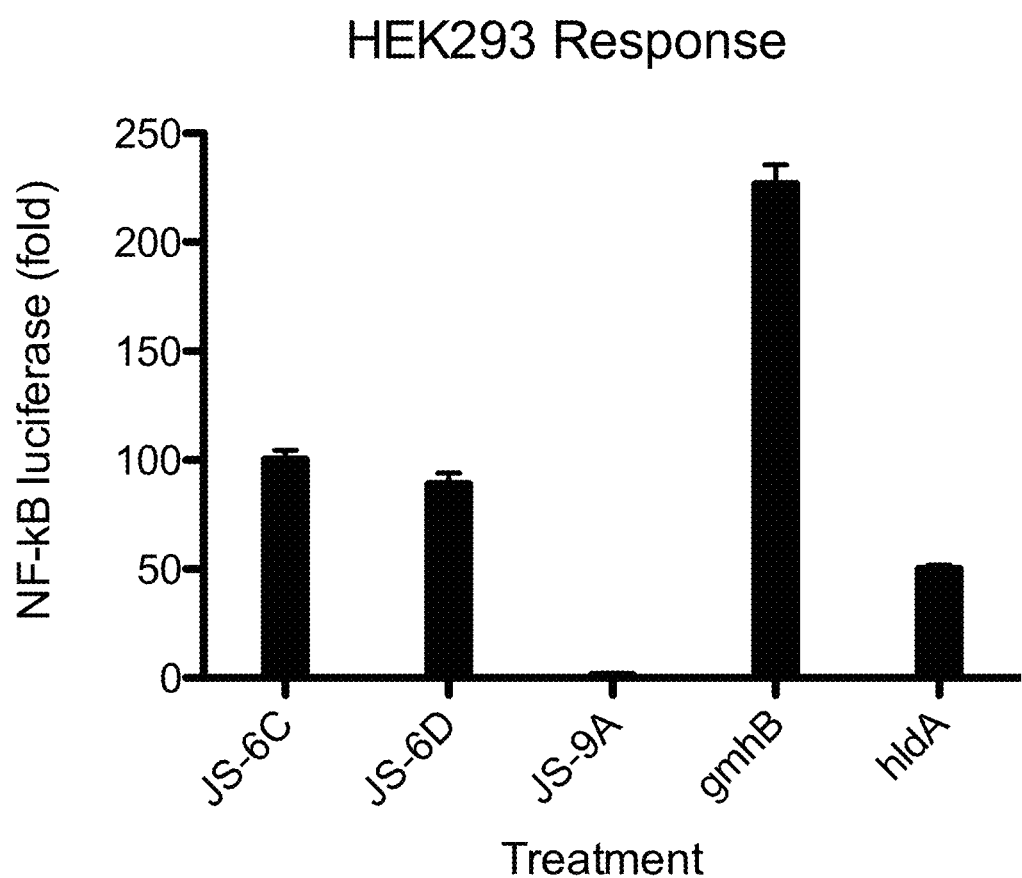
FIG. 35: Effects of compounds/products according to the invention on HEK 293T cells encoding an NF-κB-driven luciferase reporter gene. HEK 293T cells were transfected with a plasmid encoding an NF-κB-driven luciferase reporter. After 24 hours, cells were stimulated for 20 minutes in permeabilization buffer (5 μg/mL digitonin) in the presence of culture supernatant from *N. meningitidis* mutants with (gmhB) or without (hldA) HBP or 20 μg/mL of synthetic compounds according to the invention. Treatment was removed; cells were washed and incubated for 3.5 hours in complete medium. A luciferase assay was then performed. The results are mean of technical triplicates.

HBP can immunomodulate via NF-κB stimulation in vitro. HEK 293T cells were transfected with a plasmid encoding an NF-κB-driven luciferase reporter. After 24 hours, cells were stimulated for 20 minutes in permeabilization buffer (5 μg/mL digitonin) in the presence of culture supernatant from *N. meningitidis* mutants with (gmhB) or without (hldA) HBP or 20 μg/mL of synthetic compound according to the invention. Treatment was removed; cells were washed and incubated for 3.5 hours in complete medium. A luciferase assay was then performed. The results obtained are illustrated in FIG. 35. They are mean of technical triplicates.

Example 3b

Figure 36:
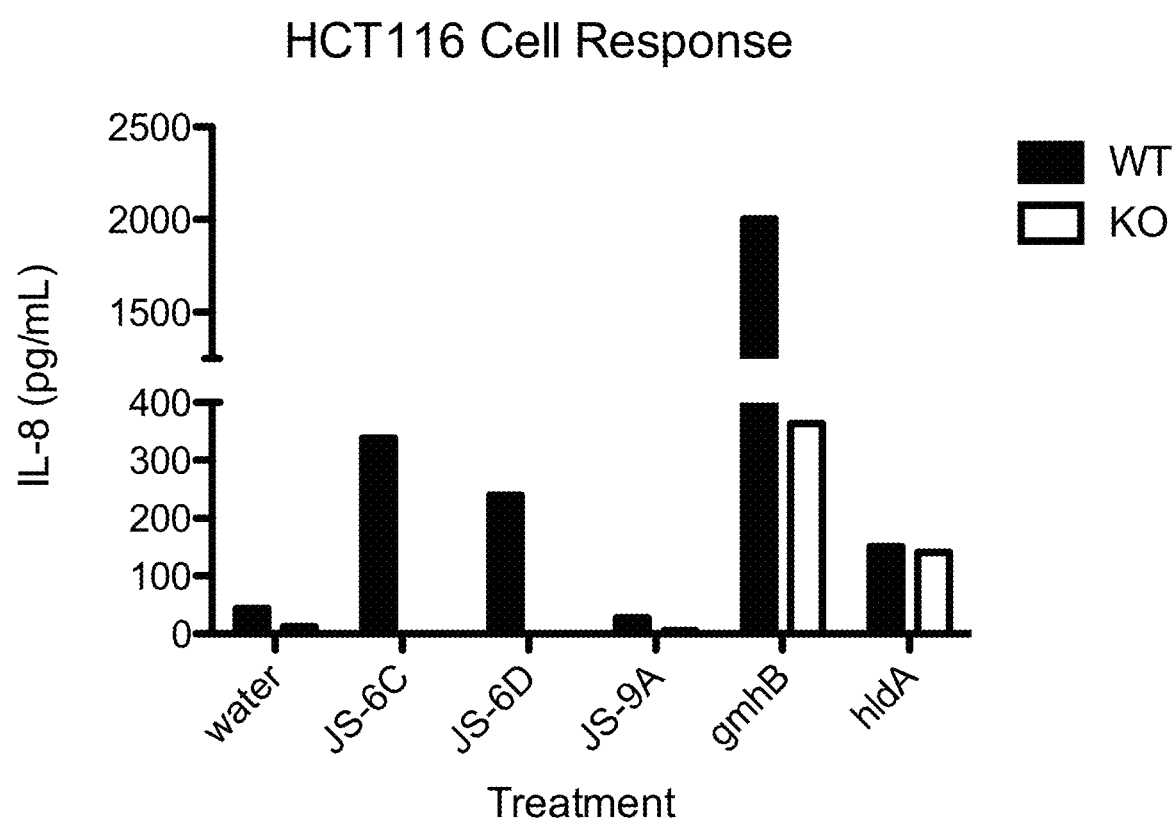
FIG. 36: Stimulation of human colonic epithelial cells by compounds/products according to the invention. Human colonic epithelial cells (HCT 116) that were either wild type (WT) or deficient in TIFA protein expression (knockout, KO) were stimulated for 20 minutes in permeabilization buffer (5 µg/mL digitonin) in the presence of culture supernatant from N. meningitidis mutants with (gmhB) or without (hldA) HBP or 10 µg/mL of synthetic compound according to the invention. Treatment was removed, cells were washed, and cells were incubated for 6 hours in complete media and IL-8 levels in culture supernatants were measured by ELISA. The results are mean of technical duplicates.

HBP can drive cytokine expression in vitro. Human colonic epithelial cells (HCT 116) that were either wild type (WT) or deficient in TIFA protein expression (knockout, KO) were stimulated for 20 minutes in permeabilization buffer (5 μg/mL digitonin) in the presence of culture supernatant from *N. meningitidis* mutants with (gmhB) or without (hldA) HBP or 10 μg/mL of synthetic compound according to the invention. Treatment was removed, cells were washed, and cells were incubated for 6 hours in complete media and IL-8 levels in culture supernatants were measured by ELISA. The results obtained are illustrated in FIG. 36. They are mean of technical duplicates.

Example 3c

Figure 37:
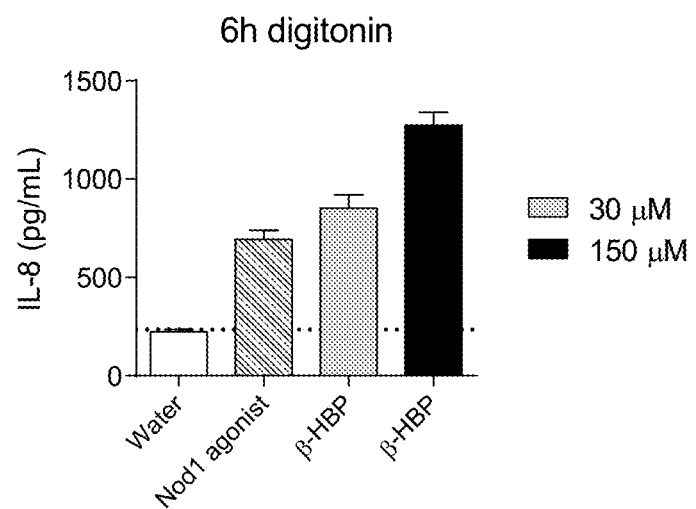
FIG. 37: Stimulation of human macrophages by compounds/products according to the invention. Human macrophage cells (THP-1) were stimulated for 20 minutes in permeabilization buffer (5 µg/mL digitonin) in the presence of water, 39.8 µM of the Nod1 agonist C12-iE-DAP (which stimulates in a TIFA-independent manner), or either 30 µM or 150 µM of synthetic compound according to the invention. Treatment was removed, cells were washed, and cells were incubated for 6 hours in complete media before the IL-8 levels in culture supernatants were measured by ELISA. The results are the mean and standard error of the mean of three technical replicates. Nod1 agonist: C12-iE-DAP (20 µg/mL, 39.8 µM); HBP: D-glycero-1-D-manno-heptose-1β,7-bi-phosphate.

HBP can drive cytokine expression in vitro. Stimulation of human macrophages by compounds/products according to the invention. Human macrophage cells (THP-1) were stimulated for 20 minutes in permeabilization buffer (5 μg/mL digitonin) in the presence of water, 39.8 μM of the Nod1 agonist C12-iE-DAP (which stimulates in a TIFA-independent manner), or either 30 μM or 150 μM of synthetic compound according to the invention. Treatment was removed, cells were washed, and cells were incubated for 6 hours in complete media before the IL-8 levels in culture supernatants were measured by ELISA (FIG. 37). The results are the mean and standard error of the mean of three technical replicates. Nod1 agonist: C12-iE-DAP (20 μg/mL, 39.8 μM); JS-7: JS-7:D-glycero-3-D-manno-heptose-phosphate.

Example 3d

Figure 38:
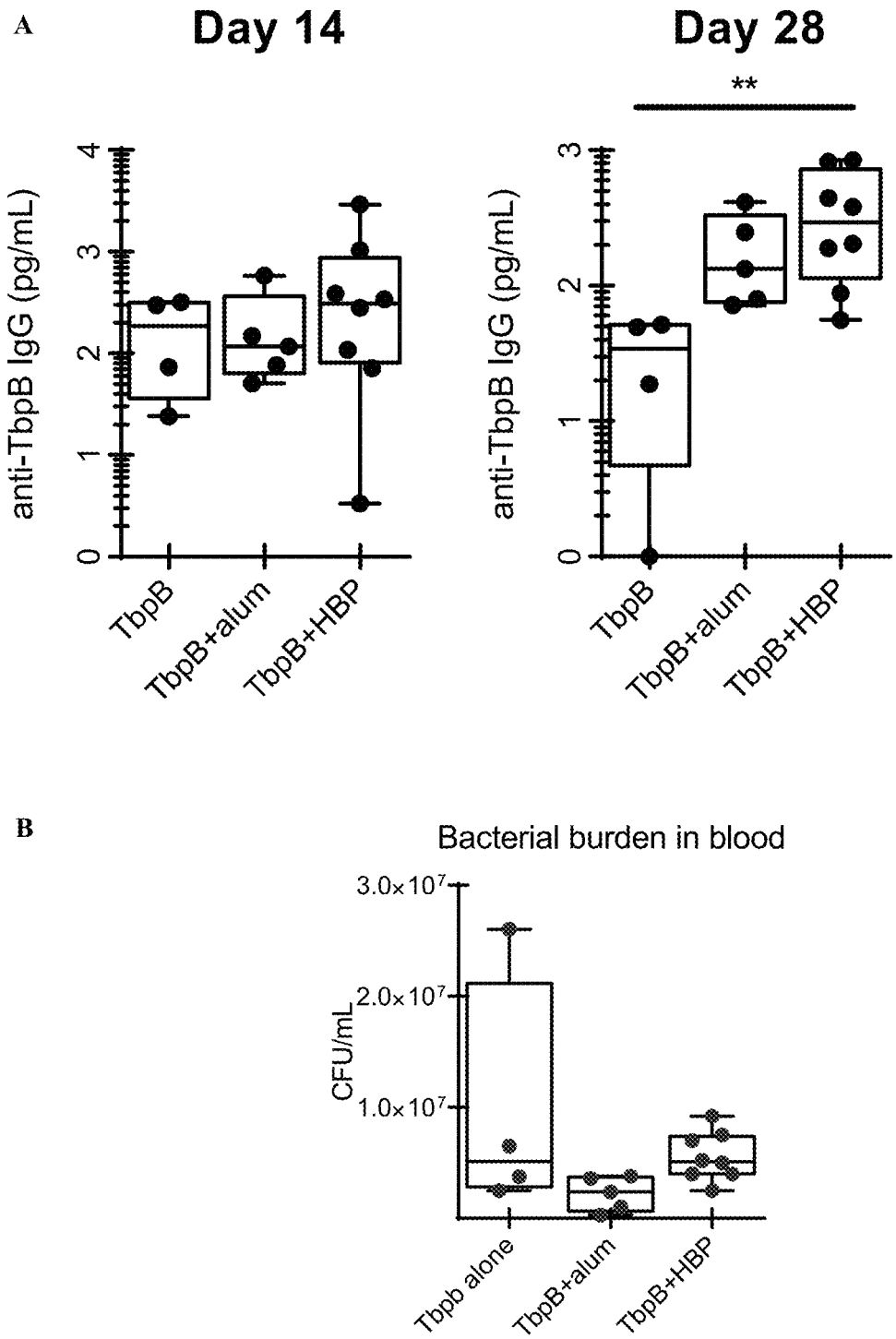
FIG. 38: 6-week-old male C57BL/6NCrl mice were immunized with TbpB originating from group B N. meningitidis, purified from recombinant E. coli. All groups were immunized with 25 µg of TbpB with or without adjuvant, in a total volume of 30 µL intramuscularly: TbpB alone, TbpB+alum, and TbpB+HBP (200 µg). Three doses were given: D0, D21, and D28. Serum was collected at D0 prior to immunization, D14, D28, and D35 and then examined by ELISA for IgG titers to TbpB (FIG. 38A). Mice were challenged on D36 with $5 \times 10^7$ of N. meningitidis strain expressing the homologous TbpB. Mice were injected with human transferrin (200 µL of 8 mg/mL) as this is critical for the development of sepsis in this model. Mice were monitored at the 1 h, 12 h, 18 h, 24 h, and 36 h time points. At 1 h, blood was collected to enumerate CFUs (FIG. 38B). Clinical scores were collected at 12 h post challenge (FIG. 38C).
Figure 38:
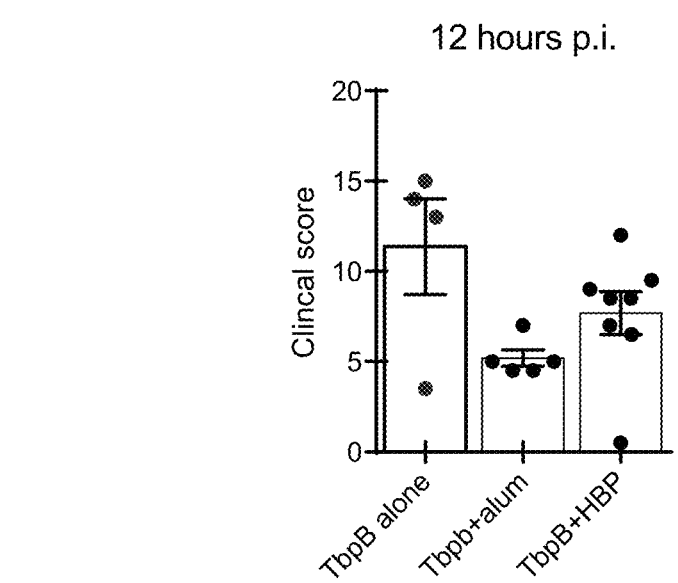

HBP can act as an adjuvant. 6-week-old male C57BL/6NCrl mice were immunized with TbpB originating from group B *N. meningitidis*, purified from recombinant *E. coli*. All groups were immunized with 25 μg of TbpB with or without adjuvant, in a total volume of 30 μL intramuscularly TbpB, TbpB+alum, and TbpB+HBP (equimolar to 200 μg). Three doses were given: D0, D21, D28. Serum was collected at D0 prior to immunization, D14, D28, and D35 and examined in ELISA for IgG titers to TbpB. HBP co-administration with the antigen resulted in titers that were significantly higher than administration of TbpB alone and greater than observed with alum as the adjuvant (FIG. 38A). Mice were challenged on D36 with 5×10$^7$ of *N. meningitidis* strain expressing matching TbpB. Mice were injected with human transferrin (200 μL of 8 mg/mL) as this is critical for the development of sepsis in this model. Mice were monitored at the 1 h, 12 h, 18 h, 24 h, and 36 h time points. At 1 h, blood was collected to enumerate CFUs. Clinical scores for mice were collected at all time points. Bacterial burden was reduced and clinical scores were lower for mice that received TbpB antigen along with alum or HBP, as opposed to TbpB alone, consistent with the elevated anti-TbpB titers. FIG. 38B bacterial burden CFU in blood and FIG. 38C clinical scores 12 h post challenge.

The scope of the claims should not be limited by the preferred embodiments set forth in the examples, but should be given the broadest interpretation consistent with the description as a whole.

The present description refers to a number of documents, the content of which is herein incorporated by reference in their entirety.

REFERENCES

1. Medzhitov R. *Immunity* (2009) 30, 766-775.
2. Medzhitov R. *Nature* (2007) 449, 819-826.
3. Brimacombe J. S. and Kabir A. K. M. S. *Carbohydr. Res.* (1986), 152, 329-334.
4. Okuda et al. *Tetrahedron Lett.* (1977) 5, 439-440.
5. Brimacombe et al. *Carbohydr. Res.* (1986) 150, 35-51.
6. Gizlek et al. *Carbohydr. Res.* (2005) 340, 2808-2811.
7. Zamyatina et al. *Carbohydr. Res.* (2003) 338, 2571-2589.
8. Wang L. et al. *Biochemistry* (2010) 49(6), 1072-1081.
9. Robinson J. A. and Moehle K. *Pure Appl. Chem.* (2014) 86(10), 1483-1538.
10. Gaudet R. G. et al. *Science* (2015) 348(6240), 1251-1255.
11. Malott R. *J. PNAS* (2013) 110(25), 10234-10239.

The invention claimed is:

1. A process for preparing D-glycero-D-manno-heptopyranose 1β,7-biphosphate, or a salt thereof, (HBP-β) comprising the steps of:
   (i) providing a D-glycero-D-manno-heptopyranose, 7-phosphate, wherein all the OH groups are protected with protecting groups;
   (ii) selectively deprotecting the OH group at position 1;
   (iii) phosphorylating the OH group at position 1, to obtain a β product, wherein the OH groups in the phosphate added at position 1 are protected; and
   (iv) deprotecting all the OH groups to obtain D-glycero-D-manno-heptopyranose 1β,7-bisphosphate.

2. The process of claim 1, comprising the reaction step as outlined below

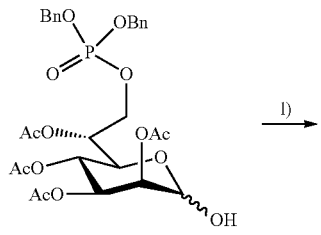

11

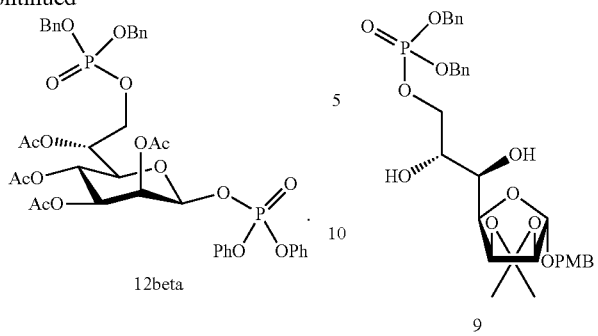
3. The process of claim 1, comprising the reaction step outlined below:
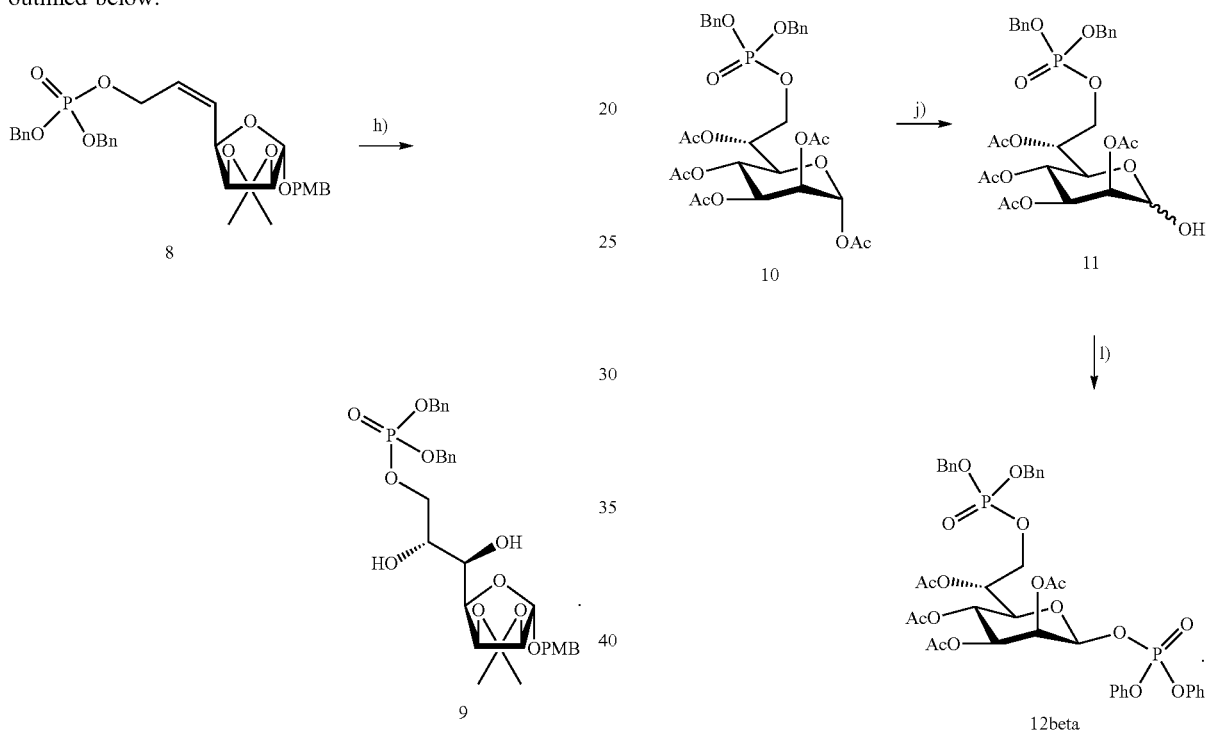
4. The process of claim 1, comprising the reaction sequence as outlined below
5. The process of claim 1, comprising the reaction sequence as outlined below:
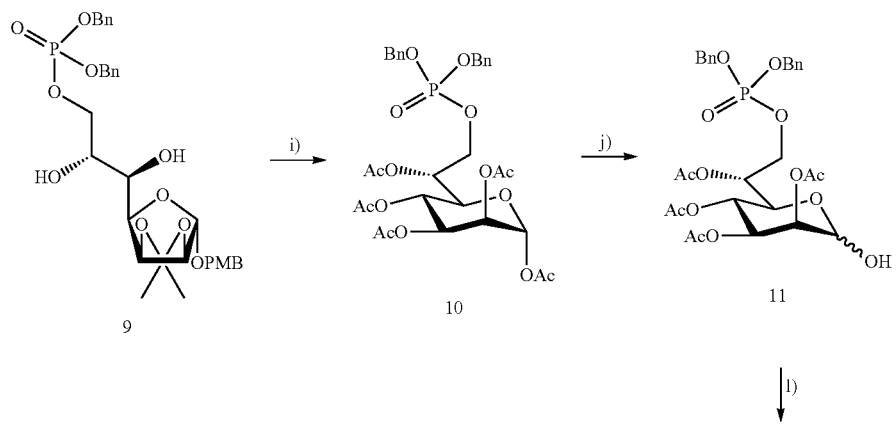

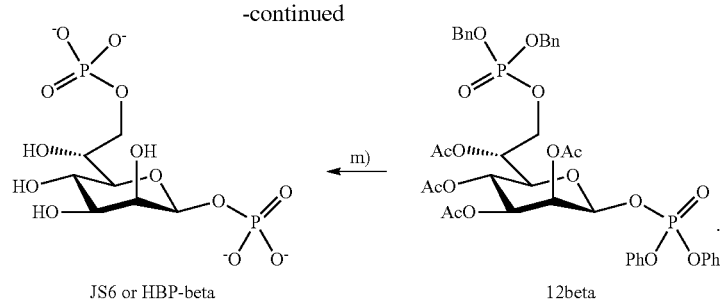
6. The process of claim 1, comprising the following reaction sequence:
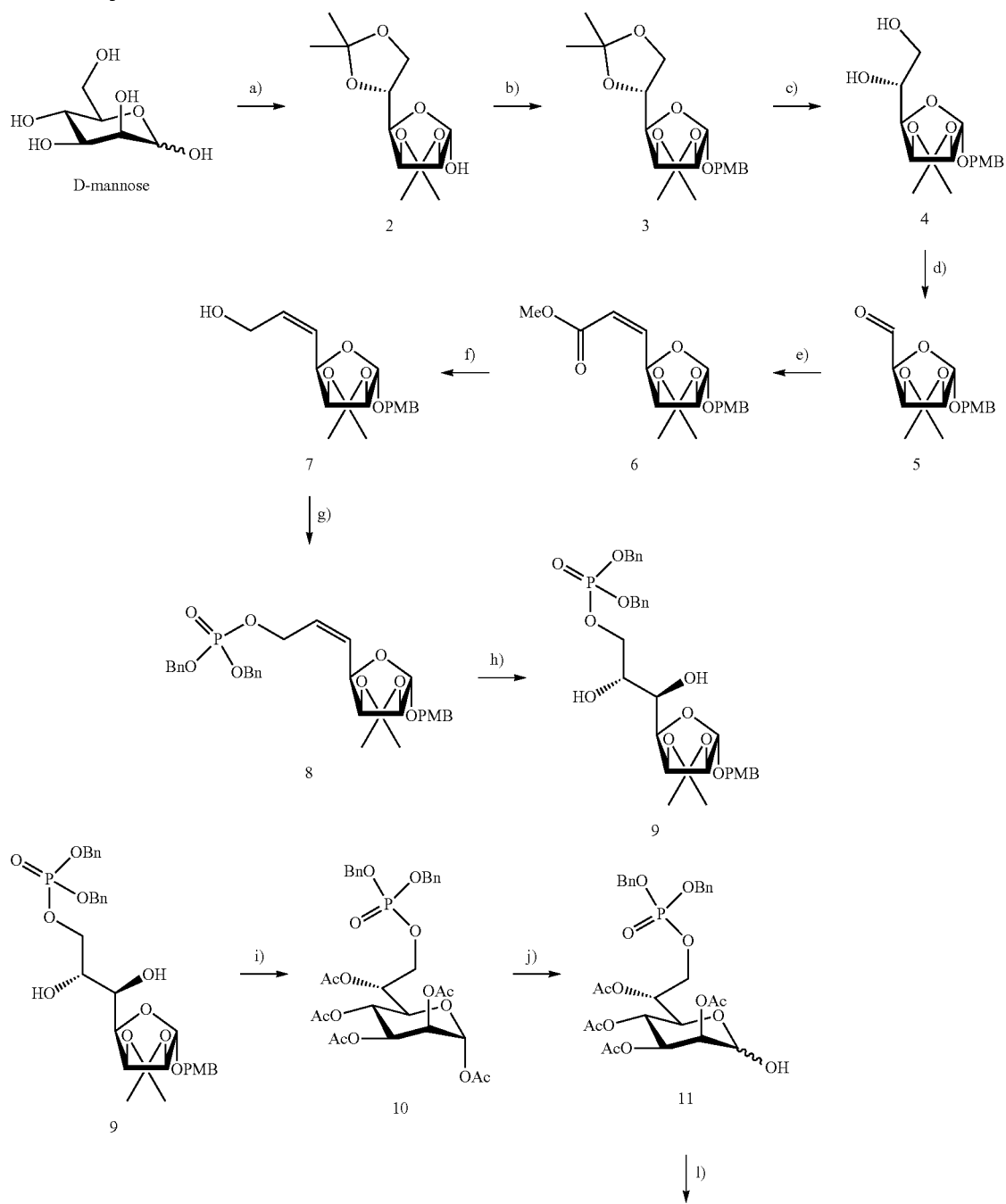

-continued

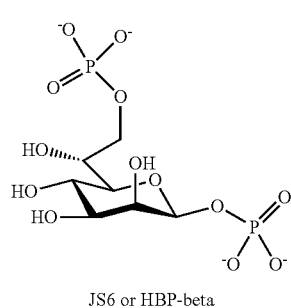

JS6 or HBP-beta m)

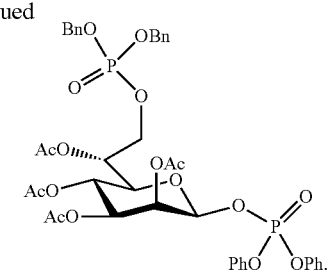

12beta

7. The process of claim 1, wherein the D-glycero-α-D-manno-heptopyranose, 7-phosphate of step (i) is a D-glycero-a-D-manno-heptopyranose, 7-phosphate.

8. The process of claim 1, comprising the steps of:
   (a) providing an α,β mixture of hydroxyl (OH)-protected D-glycero-D-manno-heptopyranose;
   (b-c) preparing, from the α,β mixture of OH-protected D-glycero-D-manno-heptopyranose, a compound wherein the hydroxy group at position 7 is protected with a first protecting group and the other five OH groups are protected with a second protecting group;
   (d) selectively deprotecting the OH at position 7 to obtain an α product;
   (e) phosphorylating the OH at position 7 of the α product;
   (f) selectively deprotecting the OH at position 1 to obtain an α,β mixture;
   (g) phosphorylating the OH at position 1 of the α,β mixture of step (d) to obtain a product;
   (h) deprotecting the other four OH groups of the β product of step (e) to obtain D-glycero-D-manno-heptopyranose 1β,7-bisphosphate or a salt thereof.

9. A The process according to claim 8, wherein:
   in the α,β mixture of OH-protected D-glycero-D-manno-heptopyranose of step (a), all the OH groups are protected with acetyl (Ac).

10. The process according to claim 8, wherein:
    step (d) comprises separating the α and β products, and step (e) is performed on the α product.

11. A The process according to claim 8, wherein the phosphorylation at steps (e) and (g) is performed independently using iPr$_2$NP(OBn)$_2$ or P(O)(OPh)$_2$Cl.

12. The process claim 8, comprising:
    a reaction sequence as outlined below:

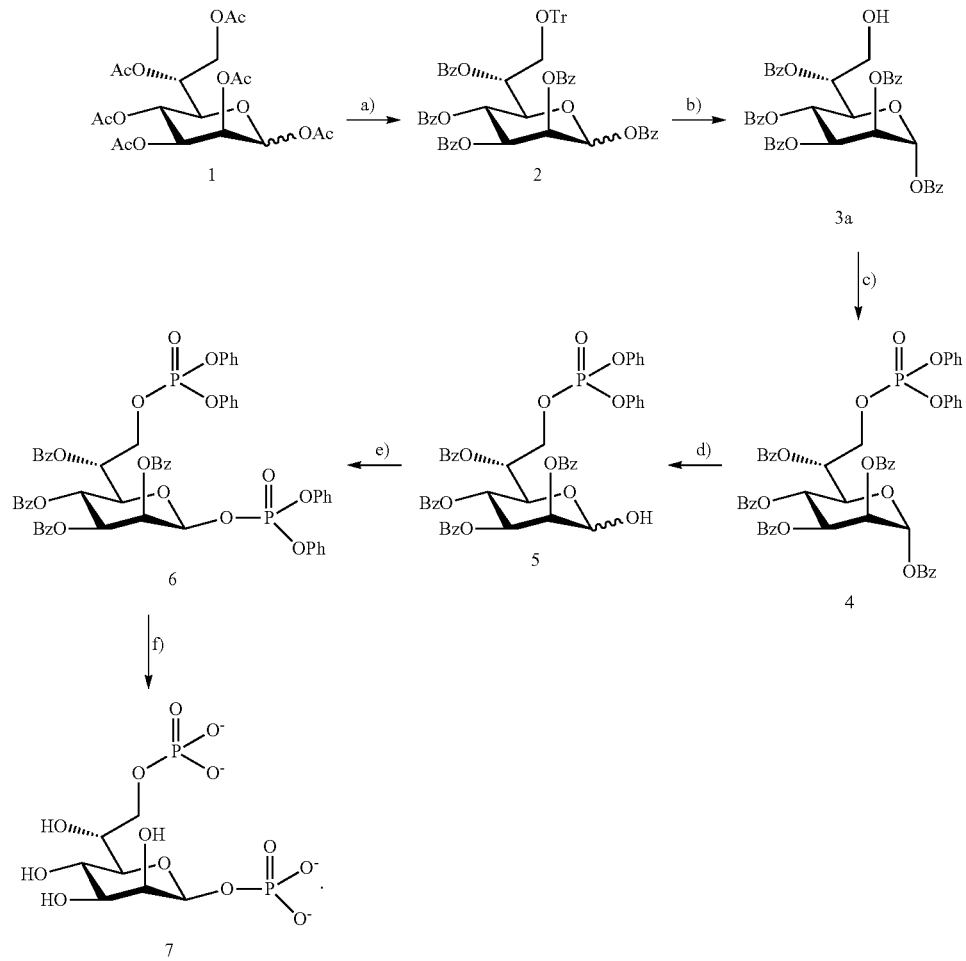

13. The process of claim 8, comprising:
a reaction step as outlined below

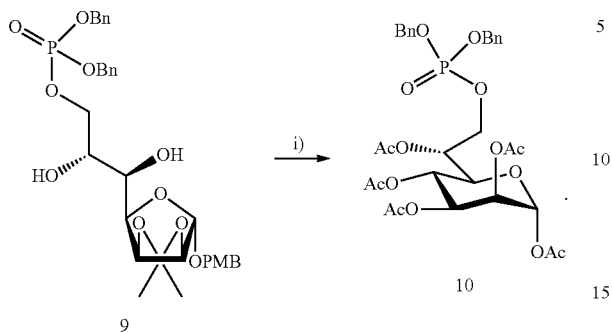

14. The process of claim 13, wherein compound 9 is obtained by the following reaction sequence:

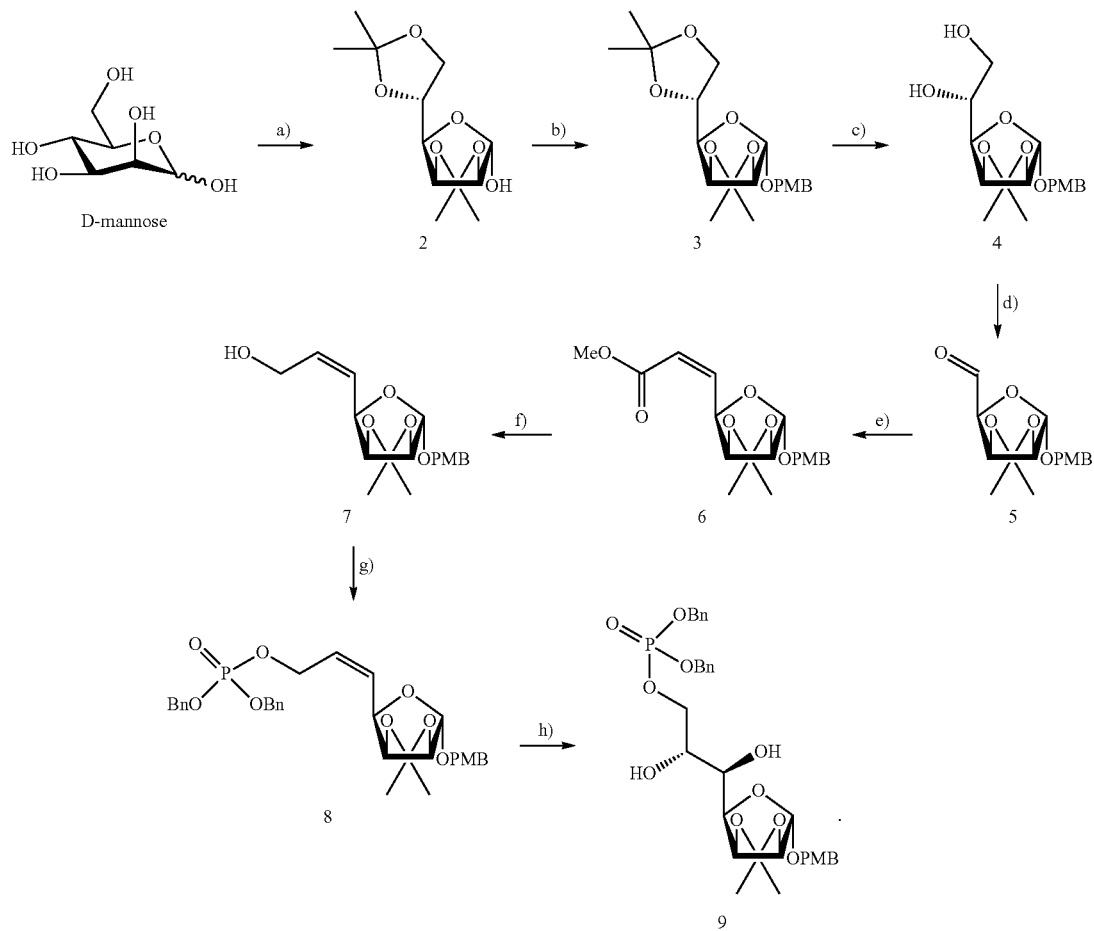

15. The process of claim 8, wherein:
in the α,β mixture of OH-protected D-glycero-D-manno-heptopyranose of step (a), all the OH groups are protected with benzoyl (Bz).

16. The process of claim 8, wherein the all the OH groups of the starting compound are each protected by acetyl (Ac), benzoyl (Bz), benzyl (Bn), p-methoxybenzyl (PMB), trimethyl silyl (TMS), tert-butyl dimethyl silyl (TBDMS), or tert-butyl diphenyl silyl (TBDPS).

17. The process of claim 8, wherein the first protecting group is triphenyl methyl (Tr or trityl), tert-butyl dimethyl silyl (TBDMS), or tert-butyl diphenyl silyl (TBDPS).

18. The process of claim 8, wherein the second protecting group is benzoyl (Bz) or acetyl (Ac).

19. The process of claim 8, wherein:
step (f) comprises separating the α and β products, and
   step (g) is performed on the β product.

* * * * *